US010076491B2

(12) United States Patent
Asari et al.

(10) Patent No.: US 10,076,491 B2
(45) Date of Patent: Sep. 18, 2018

(54) VACCINE COMPOSITION

(71) Applicant: NITTO DENKO CORPORATION, Osaka (JP)

(72) Inventors: Daisuke Asari, Osaka (JP); Katsuyuki Okubo, Osaka (JP); Takuya Shishido, Osaka (JP); Arimichi Okazaki, Osaka (JP); Yoshiki Maeda, Osaka (JP); Kyohei Matsushita, Osaka (JP); Wenjing Li, Osaka (JP); Mitsuhiko Hori, Osaka (JP); Haruo Sugiyama, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 14/166,965

(22) Filed: Jan. 29, 2014

(65) Prior Publication Data

US 2014/0220063 A1 Aug. 7, 2014

(30) Foreign Application Priority Data

Feb. 5, 2013 (JP) .................................. 2013-020734

(51) Int. Cl.

| | | |
|---|---|---|
| A61K 39/00 | (2006.01) | |
| A61K 39/02 | (2006.01) | |
| A61K 45/06 | (2006.01) | |
| A01N 63/00 | (2006.01) | |
| A61K 31/7004 | (2006.01) | |
| A61K 9/00 | (2006.01) | |
| A61K 31/407 | (2006.01) | |
| A61K 31/192 | (2006.01) | |
| A61K 31/405 | (2006.01) | |
| A61K 31/616 | (2006.01) | |
| A61K 31/196 | (2006.01) | |
| A61K 31/415 | (2006.01) | |
| A61K 31/42 | (2006.01) | |
| A61K 31/4035 | (2006.01) | |
| A61K 31/353 | (2006.01) | |
| A61K 31/5575 | (2006.01) | |
| A61K 31/216 | (2006.01) | |
| A61K 31/426 | (2006.01) | |
| A61K 38/10 | (2006.01) | |
| A61K 39/39 | (2006.01) | |

(52) U.S. Cl.

CPC .......... *A61K 9/0014* (2013.01); *A61K 31/192* (2013.01); *A61K 31/196* (2013.01); *A61K 31/216* (2013.01); *A61K 31/353* (2013.01); *A61K 31/405* (2013.01); *A61K 31/407* (2013.01); *A61K 31/4035* (2013.01); *A61K 31/415* (2013.01); *A61K 31/42* (2013.01); *A61K 31/426* (2013.01); *A61K 31/5575* (2013.01); *A61K 31/616* (2013.01); *A61K 38/10* (2013.01); *A61K 39/0011* (2013.01); *A61K 39/39* (2013.01); *A61K 2039/54* (2013.01); *A61K 2039/572* (2013.01)

(58) Field of Classification Search
CPC ............ A61K 39/0011; A61K 2039/54; A61K 38/10; A61K 38/1709
See application file for complete search history.

(56) References Cited

U.S. PATENT DOCUMENTS

| | | |
|---|---|---|
| 5,482,706 A | 1/1996 | Igari et al. |
| 2008/0112974 A1 | 5/2008 | Czerkinsky et al. |
| 2008/0193487 A1 | 8/2008 | Schild et al. |
| 2009/0130127 A1 | 5/2009 | Tokumoto et al. |
| 2011/0159035 A1 | 6/2011 | Goto et al. |

FOREIGN PATENT DOCUMENTS

| | | |
|---|---|---|
| CN | 1561204 A | 1/2005 |
| JP | 6-9424 A | 1/1994 |
| JP | 7-505883 A | 6/1995 |
| JP | 2003-516344 A | 5/2003 |
| JP | 2005-532296 A | 10/2005 |
| JP | 2007-529531 A | 10/2007 |
| JP | 2002-531415 A | 9/2009 |
| WO | 93/20847 A1 | 10/1993 |
| WO | 00/32228 A2 | 6/2000 |
| WO | 01/41741 A1 | 6/2001 |
| WO | 02/07721 A2 | 1/2002 |
| WO | 03/089593 A2 | 10/2003 |
| WO | 2005/037995 A2 | 4/2005 |
| WO | 2005-087238 A2 | 9/2005 |
| WO | 2007/015441 A1 | 2/2007 |
| WO | WO2008004992 | * 1/2008 |
| WO | 2010/013350 A1 | 2/2010 |
| WO | WO2011151431 | * 12/2011 |

OTHER PUBLICATIONS

Kaufmann et al., "Challenges and responses in human vaccine development", 2014, Current Opinion in Immunology, 28:18-26.*
Inoue et al (Journal of Investigative Dermatology, 2007, 127:614-621).*
Chen et al (Journal of Controlled Release, 2012, 159:43-51).*
Karande et al (Annual Rev. Chem. Biomol. Eng., 2010, 1:175-201).*
Wang et al., Mechanism of the effect of LPSp on the production of anti-HBs in mice, [Article in Chinese] Xi Bao Yu Fen Zi Mian Yi Xue Za Zhi, 2007, 23(6):559-561.*
Kohchi et al., Applications of Lipopolysaccharide derived from pantoea agglomerans (IP-PA1) for Health Care based on macrophage network theory, Journal of Bioscience and bioengineering, 2006, 102(6):485-496.*
K Jolly et al., Drugs, vol. 62, No. 6, 12, 2002, pp. 945-956.
A Agrawal et al., Int J. Clin. Pract., 2008, pp. 444-449.
PM Rothwell et al., The Lancet, 2010, pp. 1741-1750.

(Continued)

*Primary Examiner* — Barry A Chestnut
(74) *Attorney, Agent, or Firm* — Greenblum & Bernstein, P.L.C.

(57) ABSTRACT

The invention provides a vaccine composition containing an antigen for inducing cellular immunity, comprising at least one first cellular immunity induction promoter.

15 Claims, 1 Drawing Sheet
Specification includes a Sequence Listing.

(56) References Cited

OTHER PUBLICATIONS

Zhengrong Cui et al., Pharmaceutical Research, 2002, pp. 947-953.
Hosoi Akihiro et al., Cancer Research, 68, 2008, pp. 3941-3949.
Partial European search report issued with respect to application No. 14000320.3, dated Jun. 16, 2015.
Tamara L. Wagner et al., "Modulation of TH1 and TH2 Cytokine Production with the Immune Response Modifiers, R-848 and Imiquimod", Cellular Immunology 191, pp. 10-19, 1999.
Gerd Rechtsteiner et al., "Cutting Edge: Priming of CTL by Transcutaneous Peptide Immunization with Imiquimod", The journal of immunology, 174: 2476-2480, 2005.
Pinku Mukherjee et al., "Progression of Pancreatic Adenocarcinoma Is Significantly Impeded with a Combination of Vaccine and COX-2 Inhibition", The journal of Immunology, 182: 216-224, 2009.
Sherven Sharma et al., "Cyclooxygenase 2 Inhibition Promotes IFN-y-Dependent Enhancement of Antitumor Responses", The journal of Immunology, 174: 813-819, 2005.
European Office Action issued with respect to application No. 14000320.3, dated Dec. 16, 2016.
Yen-Huong Chow et. al., "Development of Th1 and Th2 Populations and the Nature of Immune Responses to Hepatitis B Virus DNA Vaccines Can Be Modulated by Codelivery of Various Cytokine Genes"; Journal of Immunology, vol. 160;199; pp. 1320-1329.

Morecki et. al., "Effect of indomethacin on tumorigenicity and immunity induction in a murine model of mammary carcinoma"; Int. J. Cancer, vol. 75; Mar. 16, 1998; pp. 894-899.
Naohiro Seo et. al., "The possibility of antigenic peptide, protein and DNA delivery by percutaneous vaccination"; Drug Delivery System, vol. 27, No. 3; 2012; pp. 194-201 w/ English language Abstract thereof.
Weihua Lan et. al., "Impact of Cyclooxygenase 2 Inhibitor of Profiles of Th1/Th1 Cytokines Secreted by BCG-Infected Human Cord Blood Derived Dendtitic Cells"; Journal of Clinical Urology, vol. 26, No. 5; 2011; pp. 385-388 w/ English language Abstract thereof.
Office Action issued in the corresponding Japanese application No. 2014-014809 dated Sep. 26, 2017.
1st Office Action and Search Report issued in the corresponding Chinese application No. 201410043652.3 dated Jan. 23, 2017.
2nd Office Action issued in the corresponding Chinese application No. 201410043652.3 dated Nov. 16, 2017.
Liu, "Progress in Study of Cyclooxygenase-2 and Its Inhibitors for Immunoregulation of Head and Neck Tumors";J. Clin Otorhinolaryngology and Head and Neck Surgery(China), vol. 22, No. 3; Feb. 2008; p. 141-144.
Russian Office Action with English Translation in respect to Russian Application No. 2014102945, dated Jan. 11, 2018.
Office Action issued in the corresponding European patent application No. 14000320.3 dated Jan. 8, 2018.

* cited by examiner

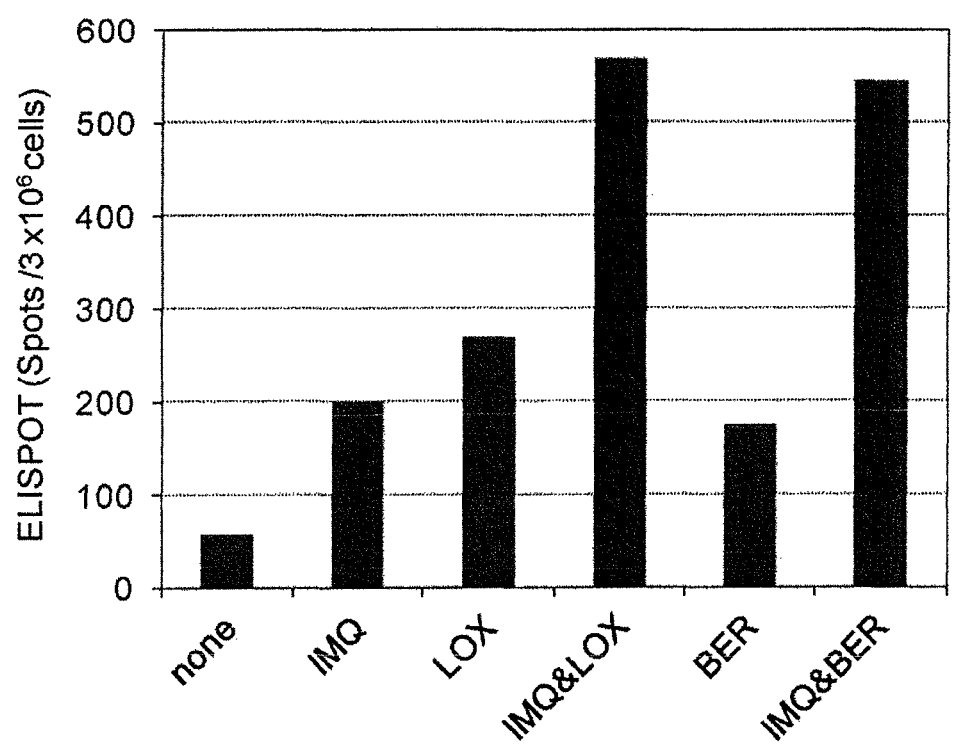

SEQUENCE LISTING

```
<160> NUMBER OF SEQ ID NOS: 18

<210> SEQ ID NO 1
<211> LENGTH: 9
<212> TYPE: PRT
<213> ORGANISM: Homo sapiens

<400> SEQUENCE: 1

Ala Tyr Ala Cys Asn Thr Ser Thr Leu
1               5

<210> SEQ ID NO 2
<211> LENGTH: 9
<212> TYPE: PRT
<213> ORGANISM: Homo sapiens

<400> SEQUENCE: 2

Glu Tyr Ile Leu Ser Leu Glu Glu Leu
1               5

<210> SEQ ID NO 3
<211> LENGTH: 9
<212> TYPE: PRT
<213> ORGANISM: Homo sapiens

<400> SEQUENCE: 3

Thr Tyr Leu Pro Thr Asn Ala Ser Leu
1               5

<210> SEQ ID NO 4
<211> LENGTH: 9
<212> TYPE: PRT
<213> ORGANISM: Homo sapiens

<400> SEQUENCE: 4

Ile Met Pro Lys Ala Gly Leu Leu Ile
1               5

<210> SEQ ID NO 5
<211> LENGTH: 9
<212> TYPE: PRT
<213> ORGANISM: Hepatitis C virus

<400> SEQUENCE: 5

Asp Leu Met Gly Tyr Ile Pro Ala Val
1               5
```

```
<210> SEQ ID NO 6
<211> LENGTH: 9
<212> TYPE: PRT
<213> ORGANISM: Homo sapiens

<400> SEQUENCE: 6

Val Leu Gln Glu Leu Asn Val Thr Val
1               5

<210> SEQ ID NO 7
<211> LENGTH: 9
<212> TYPE: PRT
<213> ORGANISM: Homo sapiens

<400> SEQUENCE: 7

Lys Val Phe Gly Ser Leu Ala Phe Val
1               5

<210> SEQ ID NO 8
<211> LENGTH: 9
<212> TYPE: PRT
<213> ORGANISM: Homo sapiens

<400> SEQUENCE: 8

Lys Val Ala Glu Ile Val His Phe Leu
1               5

<210> SEQ ID NO 9
<211> LENGTH: 9
<212> TYPE: PRT
<213> ORGANISM: Hepatitis B virus

<400> SEQUENCE: 9

Trp Leu Ser Leu Leu Val Pro Phe Val
1               5

<210> SEQ ID NO 10
<211> LENGTH: 9
<212> TYPE: PRT
<213> ORGANISM: Homo sapiens

<400> SEQUENCE: 10

Lys Ile Phe Gly Ser Leu Ala Phe Leu
1               5

<210> SEQ ID NO 11
<211> LENGTH: 9
<212> TYPE: PRT
<213> ORGANISM: Homo sapiens

<400> SEQUENCE: 11

Ser Thr Ala Pro Pro Val His Asn Val
1               5

<210> SEQ ID NO 12
<211> LENGTH: 20
<212> TYPE: DNA
<213> ORGANISM: Unknown
<220> FEATURE:
<223> OTHER INFORMATION: Description of Unknown: Bacterial DNA
      sequence

<400> SEQUENCE: 12
tccatgacgt tcctgacgtt                                              20
```

-continued

```
<210> SEQ ID NO 13
<211> LENGTH: 15
<212> TYPE: PRT
<213> ORGANISM: Mycobacterium tuberculosis

<400> SEQUENCE: 13

Phe Gln Asp Ala Tyr Asn Ala Ala Gly Gly His Asn Ala Val Phe
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Gln Asp Ala Tyr Asn Ala Val His Ala Ala His Ala Val Phe
1               5                   10                  15

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (3)..(3)
<223> OTHER INFORMATION: Cyclohexylalanine
<220> FEATURE:
<221> NAME/KEY: MOD_RES
<222> LOCATION: (13)..(13)
<223> OTHER INFORMATION: D-Ala

<400> SEQUENCE: 15

Ala Lys Ala Val Ala Ala Trp Thr Leu Lys Ala Ala Ala
1               5                   10

<210> SEQ ID NO 16
<211> LENGTH: 8
<212> TYPE: PRT
<213> ORGANISM: Gallus gallus

<400> SEQUENCE: 16

Ser Ile Ile Asn Phe Glu Lys Leu
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Lys Lys Lys Lys
1               5

<210> SEQ ID NO 18
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 18

Gly Asp Pro Lys His Pro Lys Ser Phe
1               5
```

VACCINE COMPOSITION

SEQUENCE LISTING

The instant application contains a Sequence Listing which has been submitted electronically in ASCII format and is hereby incorporated by reference in its entirety. Said ASCII copy, created on Mar. 20, 2014, is named P45220_SL.txt and is 3,668 bytes in size.

TECHNICAL FIELD

The present invention relates to vaccine compositions for cellular immunity induction.

BACKGROUND ART

Vaccines are widely used in order to induce immunity into the subject and include those for administering pathogens such as microorganisms or viruses, or a part thereof. There is a cancer vaccine for allowing a cellular immunity mechanism to recognize a cancer cell specific antigen and inducing a specific attack of the immune system to cancer cells, which is used as one measure for treating a cancer.

In usual, the invasion of microorganisms and viruses into the bio-body is prevented by skin due to the size thereof, and it is necessary to invasively administrate a vaccine into the bio-body. Accordingly, injections are usually used in order to provide immunity. Injections, however, have problems of pain, fear, an injection scar, and a needle mark and scarring thereof, and have further problems that only a medical worker is allowed to perform such administration; it is technically difficult to perform an intradermal injection having a high immune effect; there is a risk such as an infection accident caused by needlestick by a medical worker; patients are forced to go repeatedly to the hospital when repeated injection is required; and it causes medical wastes such as injection needle which is required to be disposed by a special method. Thus, injection is not necessarily an optimal route of administration.

Subcutaneous injection or intradermal injection is most generally used as the route of administration of a vaccine, but in addition to them, various routes of administration have been tried to induce immunity, for example, transdermal administration (Patent Document 1 and Non-Patent Document 1), buccal administration, transnasal administration, and sublingual administration (Non-Patent Document 2, Patent Document 2 and Patent Document 3).

In order to provide immunity by injection, it is usually used an adjuvant. For example, aluminum salts such as aluminum hydroxide, aluminum phosphate and aluminum chloride, and emulsions including squalene such as MF59 and AS03 are practically used as an adjuvant, and in addition to them, flagellum components, nucleic acids, cytokines, cationic polymers and polypeptides are widely studied as an adjuvant. With respect to an adjuvant to be used for other route than injection such as transdermal administration or transmucosal administration to provide immunity, it has also been studied to use a substance such as aluminum salts (e.g. aluminum hydroxide, aluminum phosphate and aluminum chloride), and toxins (e.g. cholera toxin and heat-labile *E. coli* toxin), but they have not yet been put into practical use. Most of them are used as an adjuvant for inducing humoral immunity by producing antibodies to prevent infection from viruses or bacteria. On the other hand, as for only cellular immunity induction, a Freund adjuvant, Montanide, GM-CSF, IL-2, IL-12 and IFN-γ have been studied as an adjuvant for injection, but they have still not yet been put into practical use. Besides, in the route of transdermal administration or mucosal administration, there are only a few reports about toxins such as cholera toxin and heat-labile *E. coli* toxin, and nucleic acids.

Further, large epidemiological surveys (Non-Patent Documents 3-5) have reported that patients which took an anti-inflammatory agent such as loxoprofen or aspirin have a low incidence of cancer. Although the mechanism is not known, one of the causes is considered to be the inhibition of the production of PGE2 released during the metastasis of cancer cells.

LIST OF DOCUMENTS

[Patent Document 1] US Patent Application Publication No. US2008/0193487
[Patent Document 2] Japanese Unexamined Patent Application Publication (Translation of PCT Application) No. 2002-531415
[Patent Document 3] US Patent Application Publication No. US2008/0112974
[Patent Document 4] Japanese Unexamined Patent Application Publication (Translation of PCT Application) No. H07-505883
[Patent Document 5] Japanese Unexamined Patent Application Publication (Translation of PCT Application) No. 2007-529531
[Non-Patent Document 1] Hosoi Akihiro et al., Cancer Research, 68, 3941-3949 (2008)
[Non-Patent Document 2] Zhengrong Cui et al., Pharmaceutical Research, Vol. 19, No. 7, 947-953 (2002)
[Non-Patent Document 3] P M Rothwell et al., The Lancet, Vol. 376, 9754, 1741-1750 (2010)
[Non-Patent Document 4] K Jolly et al., Drugs, Vol. 62, Number 6, 12, 945-956 (2002)
[Non-Patent Document 5] A Agrawal., Int J Clin Pract, 62(3), 444-449 (2008)

SUMMARY OF THE INVENTION

Cellular immunity induction promoters which have been used are limited to, for example, a Th1 adjuvant such as a Toll-like receptor ligand which facilitates the differentiation into Th1 cell; a Th1 cytokine such as IL-12; Freund's adjuvant, an oil-based adjuvant which releases an antigen in a sustained-release to improve its effect and there are some problems in the balance of their safety and effect. Further, in order to administer antigens, only invasive administration methods such as subcutaneous injection, intradermal injection, or intramuscular injection can be selected. In a therapeutic method such as cancer vaccine therapy, in which the antigen must be administered many times, there is a problem in view of patients' QOL. Since many Langerhans cells, which are antigen presenting cells, are present in skin, transdermal administration and transmucosal administration were attempted as a means for solving various problems associated with injection. However, cellular immunity induction promoters which can be used effectively in the cellular immunity induction by transdermal administration of an antigen have been rarely reported. In many cases, transdermal administration does not show sufficient cellular immunity induction effect compared to administration by injection.

An object of the invention is to provide a vaccine composition which shows high cellular immunity induction effect.

The inventors have found that cellular immunity can be induced effectively, not by directly promoting the differentiation into Th1 cells, but by inhibiting the differentiation into Th2 cells and thereby indirectly promoting the differentiation into Th1 cells. Further, the inventors have found a lot of substances which inhibit the differentiation into Th2 cells effectively and thus are useful for the cellular immunity induction. Further, the inventors have found that the Th2 cell differentiation inhibitors can be used to effectively induce cellular immunity not only in invasive administration methods such as subcutaneous injection, intradermal injection, intramuscular injection and an administration to an injured skin, but also in transdermal administration and mucosal administration of an antigen.

Immunity induction by subcutaneous, intracutaneous, or intramuscular injection, slightly causes inflammation at the site of injection by the invasion by the injection or additive comprised in the injectable solution. The inflammation is considered to promote the differentiation of Th2 cells, while inhibiting the differentiation of Th1 cells. Transmucosal administration such as nasal administration or sublingual administration requires addition of various permeation enhancers in order to increase the permeability of an antigen, and thus inflammation can be caused slightly at the site of administration. Further, in immunity induction by transdermal administration, skin is generally pre-treated in order to increase the permeability of an antigen, for example, by removing the horny layer of the skin via tape stripping. The pre-treatment also causes the inflammation at the skin. All of these administration methods cause some inflammation, which is considered to promote the differentiation of Th2 cells, and to inhibit the differentiation of Th1 cells. The inventors focused on the fact and have found that cellular immunity induction is increased by adding an agent which blocks signaling from the inflammation to the differentiation of Th2 cells. Further, the inventors have found that cellular immunity induction is further increased by further including a Th1 adjuvant which facilitates the differentiation of Th1 cells in the vaccine composition of the invention.

In one aspect of the invention, cellular immunity can be induced effectively by using a certain Th2 cell differentiation inhibitor together with an antigen. Specifically, high cellular immunity induction effect is obtained in a vaccine composition comprising least one Th2 cell differentiation inhibitor selected from the group consisting of a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenergic receptor antagonist, an adrenergic receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor.

Further, in one aspect of the invention, higher cellular immunity induction effect is obtained when the vaccine composition comprises the Th2 cell differentiation inhibitor, and also at least one cellular immunity induction promoter selected from the group consisting of a TLR ligand, a cyclic dinucleotide, a helper peptide, and an immunomodulatory small molecule drug.

Further, in one aspect of the invention, high cellular immunity induction effect is obtained by transdermal administration or transmucosal administration, as well as by subcutaneous injection, intradermal injection, and intramuscular injection. Further, in transdermal administration, cellular immunity is effectively induced by administration under mildly irritating condition.

Therefore, the invention provides aspects as listed below:
(1) A vaccine composition containing an antigen for cellular immunity induction, which comprises at least one Th2 cell differentiation inhibitor (hereinafter, also referred to as a first cellular immunity induction promoter) selected from the group consisting of a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenergic receptor antagonist, an adrenergic receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor;
(2) The vaccine composition according to (1), wherein the Th2 cell differentiation inhibitor is a cyclooxygenase inhibitor;
(3) The vaccine composition according to (1), wherein the Th2 cell differentiation inhibitor is a prostaglandin receptor antagonist, and wherein the prostaglandin receptor antagonist is an EP2 receptor antagonist, an EP4 receptor antagonist, a DP receptor antagonist, or an IP receptor antagonist;
(4) The vaccine composition according to (1), wherein the Th2 cell differentiation inhibitor is a prostaglandin receptor agonist, and wherein the prostaglandin receptor agonist is an EP3 receptor agonist;
(5) The vaccine composition according to (1), wherein the Th2 cell differentiation inhibitor is a TSLP production inhibitor;
(6) The vaccine composition according to (1), wherein the Th2 cell differentiation inhibitor is an adenylate cyclase inhibitor;
(7) The vaccine composition according to (1), wherein the Th2 cell differentiation inhibitor is an omega-3 fatty acid;
(8) The vaccine composition according to (1), wherein the Th2 cell differentiation inhibitor is a PPAR agonist, and wherein PPAR agonist is a PPAR-α agonist, a PPAR-δ agonist, or a PPAR-γ agonist;
(9) The vaccine composition according to (1), wherein the Th2 cell differentiation inhibitor is a dopamine receptor antagonist, and wherein the dopamine receptor antagonist is a D1 receptor antagonist, or a D5 receptor antagonist;
(10) The vaccine composition according to (1), wherein the Th2 cell differentiation inhibitor is a dopamine receptor agonist, and wherein the dopamine receptor agonist is a D2 receptor agonist, a D3 receptor agonist, or a D4 receptor agonist;

(11) The vaccine composition according to (1), wherein the Th2 cell differentiation inhibitor is a histamine receptor antagonist, and wherein the histamine receptor antagonist is an H1 receptor antagonist, or an H2 receptor antagonist;

(12) The vaccine composition according to (1), wherein the Th2 cell differentiation inhibitor is a histamine receptor agonist, and wherein the histamine receptor agonist is an H1 receptor agonist, an H3 receptor agonist, or an H4 receptor agonist;

(13) The vaccine composition according to (1), wherein the Th2 cell differentiation inhibitor is a serotonin receptor antagonist, and wherein the serotonin receptor antagonist is a 5-HT2 receptor antagonist, a 5-HT4 receptor antagonist, a 5-HT6 receptor antagonist, or a 5-HT7 receptor antagonist;

(14) The vaccine composition according to (1), wherein the Th2 cell differentiation inhibitor is a serotonin receptor agonist, and wherein the serotonin receptor agonist is a 5-HT1 receptor agonist, or a 5-HT2 receptor agonist;

(15) The vaccine composition according to (1), wherein the Th2 cell differentiation inhibitor is a vasopressin receptor antagonist, and wherein the vasopressin receptor antagonist is a V2 receptor antagonist;

(16) The vaccine composition according to (1), wherein the Th2 cell differentiation inhibitor is a vasopressin receptor agonist, and wherein the vasopressin receptor agonist is a V1 receptor agonist;

(17) The vaccine composition according to (1), wherein the Th2 cell differentiation inhibitor is a muscarine receptor antagonist, and wherein the muscarine receptor antagonist is an M1 receptor antagonist, an M3 receptor antagonist, or an M5 receptor antagonist;

(18) The vaccine composition according to (1), wherein the Th2 cell differentiation inhibitor is a muscarine receptor agonist, and wherein the muscarine receptor agonist is an M1 receptor agonist, an M2 receptor agonist, an M3 receptor agonist, an M4 receptor agonist, or an M5 receptor agonist;

(19) The vaccine composition according to (1), wherein the Th2 cell differentiation inhibitor is an adrenergic receptor antagonist, and wherein the adrenergic receptor antagonist is an α1 receptor antagonist, a β1 receptor antagonist, a β2 receptor antagonist, or a β3 receptor antagonist;

(20) The vaccine composition according to (1), wherein the Th2 cell differentiation inhibitor is an adrenergic receptor agonist, and wherein the adrenergic receptor agonist is an α1 receptor agonist, or an β2 receptor agonist;

(21) The vaccine composition according to (1), wherein the Th2 cell differentiation inhibitor is an angiotensin receptor agonist, and wherein the angiotensin receptor agonist is an AT2 receptor agonist;

(22) The vaccine composition according to (1), wherein the Th2 cell differentiation inhibitor is a GABA receptor agonist, and wherein the GABA receptor agonist is a $GABA_B$ receptor agonist;

(23) The vaccine composition according to (1), wherein the Th2 cell differentiation inhibitor is a thrombin receptor antagonist, and wherein the thrombin receptor antagonist is a PAR-1 receptor antagonist;

(24) The vaccine composition according to (1), wherein the Th2 cell differentiation inhibitor is a thrombin receptor agonist, and wherein the thrombin receptor agonist is a PAR-1 receptor agonist;

(25) The vaccine composition according to (1), wherein the Th2 cell differentiation inhibitor is an opioid receptor agonist;

(26) The vaccine composition according to (1), wherein the Th2 cell differentiation inhibitor is a leukotriene receptor antagonist, and wherein the leukotriene receptor antagonist is a CysLT1 receptor antagonist, or a CysLT2 receptor antagonist;

(27) The vaccine composition according to (1), wherein the Th2 cell differentiation inhibitor is a leukotriene receptor agonist, and wherein the leukotriene receptor agonist is a BLT receptor agonist;

(28) The vaccine composition according to (1), wherein the Th2 cell differentiation inhibitor is a melatonin receptor agonist;

(29) The vaccine composition according to (1), wherein the Th2 cell differentiation inhibitor is a somatostatin receptor agonist;

(30) The vaccine composition according to (1), wherein the Th2 cell differentiation inhibitor is a cannabinoid receptor agonist;

(31) The vaccine composition according to (1), wherein the Th2 cell differentiation inhibitor is a sphingosine-1 phosphate receptor agonist;

(32) The vaccine composition according to (1), wherein the Th2 cell differentiation inhibitor is a metabotropic glutamate receptor agonist, and wherein the metabotropic glutamate receptor agonist is an mGluR2 receptor agonist, an mGluR3 receptor agonist, an mGluR4 receptor agonist, an mGluR6 receptor agonist, an mGluR7 receptor agonist, or an mGluR8 receptor agonist;

(33) The vaccine composition according to (1), wherein the Th2 cell differentiation inhibitor is an ADP receptor agonist;

(34) The vaccine composition according to (1), wherein the Th2 cell differentiation inhibitor is a phospholipase A2 inhibitor;

(35) The vaccine composition according to (1), wherein the Th2 cell differentiation inhibitor is a TGF-β production inhibitor;

(36) The vaccine composition according to (1), wherein the Th2 cell differentiation inhibitor is a Th2 cytokine inhibitor;

(37) The vaccine composition according to (1), wherein the composition further comprises at least one second cellular immunity induction promoter selected from the group consisting of a TLR ligand, a cyclic dinucleotide, and an immunomodulatory small molecule drug and/or a helper peptideimmunomodulatory small molecule drug;

(38) The vaccine composition according to any one of (1)-(37), wherein the composition is administered on the skin and/or mucous membrane;

(39) The vaccine composition according to (38), wherein the composition is administered on the skin under mildly irritating condition;

(40) The vaccine composition according to (39) for transdermal administration, wherein the mildly irritating condition is a condition under which transepidermal water loss (TEWL) in a model animal for skin irritation evaluation before the administration of the composition is 50 g/h·m² or less;

(41) The vaccine composition according to (39) for transdermal administration, wherein the mildly irritating condition is a condition under which TSLP level in a model animal for skin irritation evaluation at completion of the administration of the composition is 10000 pg/mg protein or less;

(42) The vaccine composition according to anyone of (1)-(37), wherein the composition is administered by intradermal injection, subcutaneous injection, or intramuscular injection.

In another aspect, the vaccine composition of the invention can be used for treating or preventing a disease. Therefore, the invention also provides the following embodiments:

(43) A method for treating or preventing a cancer in a subject, comprising administrating to the subject a therapeutically effective amount of (i) an cancer antigen and (ii) at least one Th2 cell differentiation inhibitor selected from the group consisting of a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenergic receptor antagonist, an adrenergic receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor;

(44) A method for treating or preventing an infectious disease in a subject, comprising administrating to the subject a therapeutically effective amount of (i) an antigen derived from an infectious pathogen, and (ii) at least one Th2 cell differentiation inhibitor selected from the group consisting of a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenergic receptor antagonist, an adrenergic receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor.

In another aspect, the invention also provides a combination of (i) at least one agent selected from the group consisting of a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenergic receptor antagonist, an adrenergic receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor, and (ii) at least one agent selected from the group consisting of a TLR ligand, a cyclic dinucleotide and an immunomodulatory small molecule drug, and/or a helper peptide, for inducing cellular immunity to an antigen. Therefore, the invention also provides the following aspect:

(45) A combination of (i) at least one selected from the group consisting of a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenergic receptor antagonist, an adrenergic receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor, and (ii) at least one selected from the group consisting of a TLR ligand, a cyclic dinucleotide and an immunomodulatory small molecule drug, and/or a helper peptide, for inducing cellular immunity to an antigen.

The present invention also provides the following embodiments:

(46) A method for inducing cellular immunity, which comprises administering to a subject (i) an antigen and (ii) one or more Th2 cell differentiation inhibitors selected from the group consisting of cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor and Th2 cytokine inhibitor; (47) one or more Th2 cell differentiation inhibitors selected from the group consisting of cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor and Th2 cytokine inhibitor, for use in promoting the induction of cellular immunity against an antigen;

(48) a combination of (i) an antigen and (ii) one or more Th2 cell differentiation inhibitors selected from the group consisting of cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor and Th2 cytokine inhibitor, for use in inducing cellular immunity against the antigen;

(49) a combination of (i) an antigen, (ii) one or more Th2 cell differentiation inhibitors selected from the group consisting of cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor and Th2 cytokine inhibitor (a first cellular immunity induction promoter) and (iii) one or more second cellular immunity induction promoters selected from the group consisting of TLR ligand, cyclic dinucleotide and immunomodulatory small molecule drug, and/or helper peptide, for use in inducing cellular immunity against the antigen;

(50) a combination of (i) a cancer antigen and (ii) one or more Th2 cell differentiation inhibitors selected from the group consisting of cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor and Th2 cytokine inhibitor, for use in treating or preventing a cancer;

(51) a combination of (i) an antigen derived from infectious pathogen and (ii) one or more Th2 cell differentiation inhibitors selected from the group consisting of cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor and Th2 cytokine inhibitor, for use in treating or preventing an infectious disease;

(52) Use of (i) an antigen and (ii) one or more Th2 cell differentiation inhibitors selected from the group consisting of cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor and Th2 cytokine inhibitor, for the manufacture of vaccine composition for the induction of cellular immunity against the antigen;

(53) Use of (i) a cancer antigen and (ii) one or more Th2 cell differentiation inhibitors selected from the group consisting of cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor and Th2 cytokine inhibitor, for the manufacture of vaccine composition for the treatment or prevention of a cancer; and

(54) Use of (i) an antigen derived from infectious pathogen and (ii) one or more Th2 cell differentiation inhibitors selected from the group consisting of cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor and Th2 cytokine inhibitor, for the manufacture of vaccine composition for the treatment or prevention of an infectious disease.

The vaccine composition of the invention can induce cellular immunity effectively without using any Th1 adjuvant which directly acts onimmunocompetent cells. Further, the Th2 cell differentiation inhibitors found in the invention includes many agents which are commercially available in pharmacies and widely known to be safe, and thus advantageous in view of side effects.

Further, the vaccine composition of the invention can be administered transdermally and mucosally, in addition to by subcutaneous injection, intradermal injection, and intramuscular injection and thus have following advantages: excellent in compliance, for example, non-invasively administration, painless, no fear of injection; patients can administer the vaccine composition himself/herself since the administration is simple; health care professionals can avoid a risk of a needlestick injury, the burden of going to the hospital can be decreased if they are repeatedly administered and patients' quality of life can be improved, no medical wastes such as a needle which needs to discard in a special way. Further, in patches such as cataplasm preparations or tape preparations, the composition has advantages that a predetermined dosage can be administered surely, the release velocity of the agents can be suitably controlled, and agents doesn't attach other site when administered. Further, since patches can be easily attached and removed, if patients experience any side effect, patients can stop the administration immediately by removing the patch from the site of administration. Further, the vaccine composition of the invention has an advantage that the efficacy is remarkably improved compared to the administration of the antigen only. Further, the vaccine composition of the invention has an advantage that transdermal administration and mucosal administration of the composition can induce stronger immunity than administration by injection.

BRIEF DESCRIPTION OF THE DRAWINGS

FIG. 1 shows a synergistic effect when a combination of a Th2 cell differentiation inhibitor loxoprofen (LOX) or berberine (BER), and a Th1 adjuvant imiquimod (IMQ) is used.

DETAILED DESCRIPTION OF THE INVENTION

The definitions as used herein are defined as follows for the purpose of easier understanding of the invention. The terms having no definition herein have the meanings generally understood by person skilled in the art, in particular, in medical, pharmaceutical, immunology, cell biology, biochemistry, polymer chemistry, or the like, unless otherwise indicated by the context.

I. Definitions

As used herein, the term "an antigen" means all substances being capable of inducing an immune response, and includes, for example, a protein, or a peptide. Further, for transdermal administration wherein skin permeability of an antigen is required, a low molecular weight antigen is preferred and a peptide having about 8 to about 12 amino acids can be used. In the invention, for example, a survivin-2B peptide, a GPC3 peptide, an HER2/neu_A24 peptide, an MAGE3_A24 peptide, an IPEP87 peptide, a PR1 peptide, an HER2/neu_A02 peptide, an MAGE3_A02 peptide, an HBVenv peptide, an HER2/neu E75 peptide, and an MUC1 peptide as described below can be used as the antigen.

In one embodiment, at least one peptide selected from the group consisting of a HER2/neu E75 peptide for use in a cancer vaccine for transdermal or mucosal administration, a modified HER2/neu E75 peptide for use in a cancer vaccine for transdermal or mucosal administration, a WT1 peptide for use in a cancer vaccine for transdermal or mucosal administration, and a modified WT1 peptide for use in a cancer vaccine for transdermal or mucosal administration is excluded from the antigen to be used in the vaccine composition of the invention.

As used herein, the term "survivin-2B peptide" means a peptide derived from a cancer gene product survivin, the peptide consisting of a sequence Ala Tyr Ala Cys Asn Thr Ser Thr Leu (SEQ ID NO: 1).

As used herein, the term "GPC3 peptide" means a peptide derived from a cancer gene product GPC3, the peptide consisting of a sequence Glu Tyr Ile Leu Ser Leu Glu Glu Leu (SEQ ID NO: 2).

As used herein, the term "HER2/neu_A24 peptide" means a HLA-A24-binding peptide derived from a cancer gene product HER2/neu, the peptide consisting of a sequence Thr Tyr Leu Pro Thr Asn Ala Ser Leu (SEQ ID NO: 3).

As used herein, the term "MAGE3_A24 peptide" means a HLA-A24-binding peptide derived from a cancer gene product MAGE3, the peptide consisting of a sequence Ile Net Pro Lys Ala Gly Leu Leu Ile (SEQ ID NO: 4).

As used herein, the term "IPEP87 peptide" means a peptide derived from a hepatitis C virus (HCV) protein, the peptide consisting of a sequence Asp Leu Net Gly Tyr Ile Pro Ala Val (SEQ ID NO: 5).

As used herein, the term "PR1 peptide" means a peptide derived from a cancer gene product proteinase-3, the peptide consisting of a sequence Val Leu Gln Glu Leu Asn Val Thr Val (SEQ ID NO: 6).

As used herein, the term "HER2/neu_A02 peptide" means a HLA-A02 binding peptide derived from a cancer gene product HER2/neu, the peptide consisting of a sequence Lys Val Phe Gly Ser Leu Ala Phe Val (SEQ ID NO: 7).

As used herein, the term "MAGE3_A02 peptide" means a HLA-A02 binding peptide derived from a cancer gene product MAGE3, the peptide consisting of a sequence Lys Val Ala Glu Ile Val His Phe Leu (SEQ ID NO: 8).

As used herein, the term "HBVenv peptide" means a peptide derived from a Hepatitis B virus (HBV) protein, the peptide consisting of a sequence Trp Leu Ser Leu Leu Val Pro Phe Val (SEQ ID NO: 9).

As used herein, the term "HER2/neu E75 peptide" means a peptide derived from a cancer gene HER2/neu product (HER2 protein), the peptide consisting of a sequence Lys Ile Phe Gly Ser Leu Ala Phe Leu (SEQ ID NO: 10).

As used herein, the term "MUC1 peptide" means a peptide derived from a glycoprotein MUC1 protein highly expressing in many cancer cells, the peptide consisting of a sequence Ser Thr Ala Pro Pro Val His Asn Val (SEQ ID NO: 11).

As used herein, the term "WT1 peptide" means a partial peptide consisting of about 8 to about 15, preferably about 8 to about 12 amino acids and obtained by fragmenting the WT1 protein which is a product of cancer gene WT1 (Wilm's tumor), and includes a Db126 peptide or a Db235 peptide (both are described in U.S. Pat. No. 4,422,903). Further, the partial peptide of the WT1 product as disclosed in WO2000/06602, the WT1 derived HLA-A26-binding cancer antigen peptide as described in WO2005/095598, the HLA-A*3303-binding WT1 peptide as described in WO2007/097358, and the HLA-A*1101-binding WT1 peptide as described in WO2008/081701 are also included in the "WT1 peptide" as described herein.

As used herein, the term "modified XX peptide" (XX is a name of any peptide) means a peptide modified by substitution, modification, or the like of all or a part of the amino acids of the XX peptide.

Modified XX Peptide Includes, for Example, (a) a peptide consisting of an amino acid sequence in which one or more, for example, one, two, three, four, or five amino acids are substituted, deleted, or added in the amino acid sequence of the XX peptide; and (b) a peptide consisting of an amino acid sequence in which all or a part of the amino acids, for example, one or more, for example, one, two, three, four, five, six, seven, eight, nine, or ten amino acids are modified in the amino acid sequence of the XX peptide.

The "modification" of amino acids which the modified XX peptide can have includes, without limitation, for example, acetylation, alkylation such as methylation, glycosylation, hydroxylation, carboxylation, aldehyde formation, phosphorylation, sulfonylation, formylation, modification by aliphatic chain addition such as myristoylation, palmitoylation, or stearoylation, octanolyation, esterification, amidation, deamidation, modification by disulfide bond formation such as cystine modification, glutathione modification, or thioglycolic acid modification, glycosylation, ubiquitination, succinimide formation, glutamylation, and prenylation. The modified XX peptide may include a combination of a substitution, deletion, or addition of at least one amino acid, and a modification of at least one amino acid.

In a preferred aspect, an antigen included in the vaccine composition of the invention for transdermal administration is a peptide selected from the group consisting of a survivin-2B peptide and/or a modified survivin-2B peptide, a GPC3 peptide and/or a modified GPC3 peptide, an HER2/neu_A24 peptide and/or a modified HER2/neu_A24 peptide, an MAGE3_A24 peptide and/or a modified MAGE3_A24 peptide, an IPEP87 peptide and/or a modified IPEP87 peptide, a PR1 peptide and/or a modified PR1 peptide, an HER2/neu_A02 peptide and/or a modified HER2/neu_A02 peptide, an MAGE3_A02 peptide and/or a modified MAGE3_A02 peptide, an HBVenv peptide and/or a modified HBVenv peptide, and an MUC1 peptide and/or a modified MUC1 peptide. Alternatively, an HER2/neu E75 peptide and/or a modified HER2/neu E75 peptide can be used as the antigen.

The peptide as listed above may be a free form or any pharmacologically acceptable salts, for example, acid salts (such as, acetate, TFA salt, hydrochloride, sulfate, phosphate, lactate, tartrate, maleate, fumarate, oxalate, hydrobromate, succinate, nitrate, malate, citrate, oleate, palmitate, propionate, formate, benzoate, picrate, benzenesulfonate, dodecylsulfate, methanesulfonate, p-toluenesulfonate, glutarate, or various amino acid salts), metal salts (alkali metal salts (for example, sodium salts, or potassium salts), alkaline earth metal salts (for example, calcium salts, or magnesium salts), aluminum salt), amine salts (triethylamine salts, benzylamine salts, diethanol amine salts, t-butylamine salts, dicyclohexylamine salts, alginine salts, dimethyl ammonium salts, or ammonium salts). Preferred pharmacologically acceptable salts are acetate salts or TFA salts. The peptide which may be used as the antigen in the invention can be synthesized or produced, isolated and purified by any well known method.

As used herein, the term "Th1 cell" and "Th2 cell" mean a type-1 helper T cell and a type-2 helper T cell, respectively.

The cellular immunity induction effect can be measured by an immunity induction study using a model animal for immunological evaluation and ELISPOT method (IFN-γ). The sample for measuring cellular immunity may be spleen of the model animal for immunological evaluation.

As used herein, the term "cellular immunity induction promoter" means any substance which can enhance the cellular immune response induced by an antigen which is administered together with the substance, as compared with the immune response induced by the antigen without the substance. The cellular immunity induction promoter may include substances specified in the present specification, though it is not limited by the action mechanism by which induction of the cellular immunity is promoted.

In one preferred aspect, the invention is accomplished by administering a vaccine composition comprising an antigen, and at least one Th2 cell differentiation inhibitor selected from the group consisting of a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenergic receptor antagonist, an adrenergic receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor.

As used herein, the term "Th2 cell differentiation inhibitor" means a substance which inhibits differentiation from Th0 s to Th2 cells. In one aspect, the Th2 cell differentiation inhibitor is a first cellular immunity induction promoter of the invention.

As used herein, the term "cyclooxygenase inhibitor" means a substance which inhibits a function of a cyclooxygenase (COX). Hereinafter, the cyclooxygenase inhibitor is also called as a "COX inhibitor". The COX inhibitor includes ones which act selectively on a certain cyclooxygenase (for example, COX-1, COX-2), or ones which have no selectivity on it. The COX inhibitor which can be used in the invention includes etodolac, loxoprofen, celecoxib, valdecoxib, parecoxib, lumiracoxib, meloxicam, tenoxicam, diclofenac, mefenamic acid, tolfenamic acid, flufenamic acid, meclofenamic acid, niflumic acid, benzydamine, indobufen, triflusal, tolmetin, fenoprofen, tiaprofenic acid, felbinac, nepafenac, amfenac, pravadoline, zaltoprofen, sulindac, nabumetone, diflunisal, piroxicam, ibuprofen, naproxen, fenoprofen, aspirin, methyl salicylate, salicylamide, salsalate, aloxiprin, tolmetin, indomethacin, proglumetacine, acemetacin, flurbiprofen, pranoprofen, acetaminophen, floctafenine, lornoxicam, tenoxicam, tiaprofenic acid, oxaprozin, ketoprofen, dexketoprofen, dexibuprofen, alminoprofen, ketorolac, mofezolac, phenylbutazone, oxyphenylbutazone, ketophenylbutazone, feprazone, phenbutazone, ethenzamide, tiaramide, tinoridine, epirizole, emorfazone and derivatives thereof, and pharmacologically acceptable salts thereof. In a preferred aspect of the invention, COX inhibitor is etodolac and/or loxoprofen.

Loxoprofen is represented by the formula:

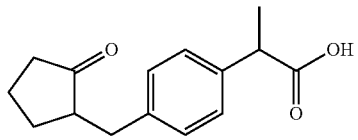 [SMILES: CC(C(=O)O)c1ccc(CC2CCCC2=O)cc1]

As used herein, the term "prostaglandin receptor antagonist" means a substance which has an inhibitory function on an action of prostaglandin to its receptor, for example, including an EP2 receptor antagonist, an EP4 receptor antagonist, a DP receptor antagonist, and an IP receptor antagonist.

As used herein, the term "EP2 receptor antagonist" means a substance which has an inhibitory function on an action of prostaglandin E2 to an EP2 receptor. The EP2 receptor antagonist includes an AH6809 and derivatives thereof, and pharmacologically acceptable salts thereof.

AH6809 is represented by the formula:

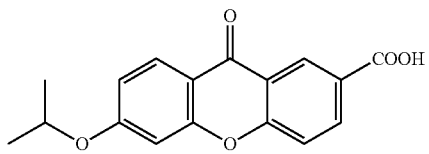 [SMILES: CC(C)Oc1ccc2c(=O)c3cc(C(=O)O)ccc3oc2c1]

As used herein, the term "EP4 receptor antagonist" means a substance which has an inhibitory function on an action of prostaglandin $E_2$ to an EP4 receptor. The EP4 receptor antagonist includes a GW627368X and derivatives thereof, and pharmacologically acceptable salts thereof.

GW627368X is represented by the formula:

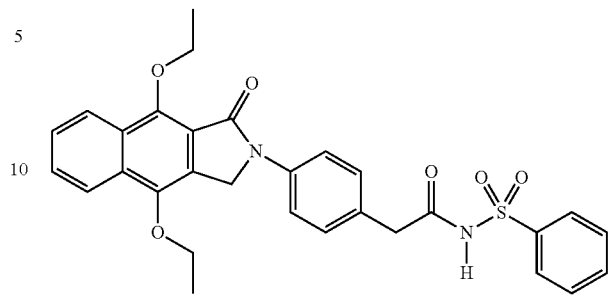

As used herein, the term "DP receptor antagonist" means a substance which has an inhibitory function on an action of prostaglandin $D_2$ to a DP receptor. The DP receptor antagonist includes S-5751, BWA868C and derivatives thereof, and pharmacologically acceptable salts thereof.

BWA868C is represented by the formula:

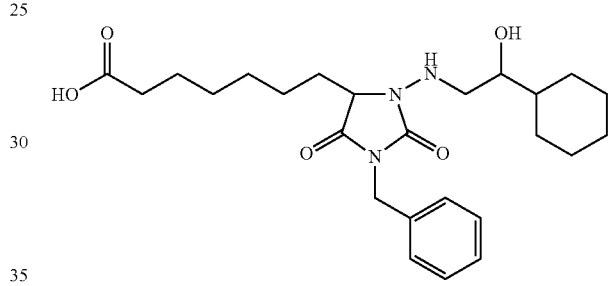

As used herein, the term "IP receptor antagonist" means a substance which has an inhibitory function on an action of prostaglandin $I_2$ to an IP receptor. The IP receptor antagonist includes RO1138452 and derivatives thereof, and pharmacologically acceptable salts thereof.

RO1138452 is represented by the formula:

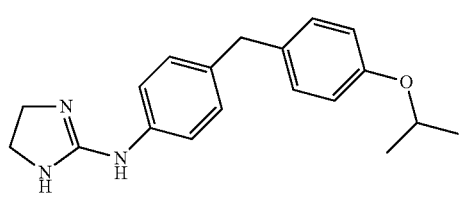 [SMILES: CC(C)Oc1ccc(Cc2ccc(NC3=NCCN3)cc2)cc1]

As used herein, the term "prostaglandin receptor agonist" means a substance which has itself a function of acting on a prostaglandin receptor, for example, including an EP3 receptor agonist.

As used herein, the term "EP3 receptor agonist" means a substance which has itself a function of acting on an EP3 receptor. The EP3 receptor agonist includes sulprostone, GR63799, cloprostenol, ONO-AE-248, carbacyclin, and derivatives thereof, and pharmacologically acceptable salts thereof.

Sulprostone is represented by the formula:

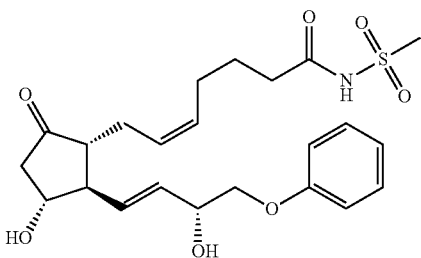 [SMILES: CS(=O)(=O)NC(=O)CCC/C=C\C[C@H]1C(=O)C[C@@H](O)[C@@H]1/C=C/[C@@H](O)COc1ccccc1]

As used herein, the term "TSLP production inhibitor" means a substance which has an inhibitory function on production of TSLP. Substances which inhibit NF-kB are also included in this category because these substances are thought to inhibit the production of TSLP indirectly. The TSLP production inhibitor includes naringenin, berberine, resveratrol, luteolin, apigenin, chrysoeriol, vertin, rutin, hesperidin, quercetin, daidzein, genistein, noscapine, diindolylmethane, xanthone, parthenolide and derivatives thereof, and pharmacologically acceptable salts thereof.

Berberine is represented by the formula:

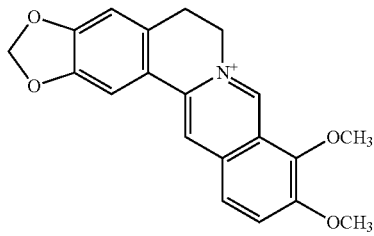 [SMILES: COc1ccc2cc3[n+](cc2c1OC)CCc1cc2c(cc1-3)OCO2]

As used herein, the term "adenylate cyclase inhibitor" means a substance which has an inhibitory function on an activity of adenylate cyclase. The adenylate cyclase inhibitor includes 2',5'-dideoxyadenosine, niacin, insulin, and derivatives thereof, and pharmacologically acceptable salts thereof.

2',5'-dideoxyadenosine is represented by the formula:

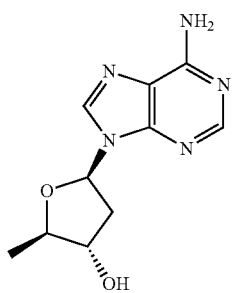 [SMILES: C[C@H]1O[C@@H](n2cnc3c(N)ncnc32)C[C@@H]1O]

As used herein, the term "omega-3 fatty acid" refers to a member of unsaturated fatty acids having a carbon-carbon double bond at ω-3 position. The omega-3 fatty acid includes eicosapentaenoic acid, α-linolenic acid, docosahexaenoic acid, and derivatives thereof, and pharmacologically acceptable salts thereof.

Eicosapentaenoic acid is represented by the formula:

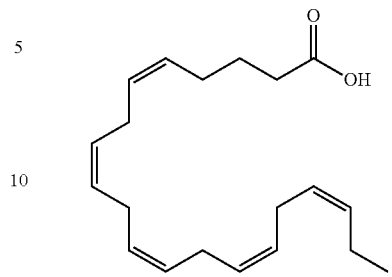

As used herein, the term "PPAR agonist" means a substance which has itself a function of acting on a peroxisome growth factor-activated receptor, for example, including a PPAR-α agonist, a PPAR-δ agonist, and a PPAR-γ agonist.

As used herein, the term "PPAR-α agonist" means a substance which has itself a function of acting on an α-type peroxisome growth factor-activated receptor. The term "PPAR-δ agonist" means a substance which has itself a function of acting on a δ-type peroxisome growth factor-activated receptor. The term "PPAR-γ agonist" means a substance which has itself a function of acting on a γ-type peroxisome growth factor-activated receptor. The PPAR-α agonist, and/or the PPAR-δ agonist, and/or the PPAR-γ agonist includes clofibrate, fenofibrate, bezafibrate, ciprofibrate, etofibrate, telmisartan, oleylethanolamide, tetradecylthioacetic acid, troglitazone, pioglitazone, rosiglitazone, balaglitazone, rivoglitazone, ciglitazone, darglitazone, edaglitazone, netoglitazone, Indeglitazar, tesaglitazar, muraglitazar, aleglitazar, and derivatives thereof, and pharmacologically acceptable salts thereof.

Clofibrate is represented by the formula:

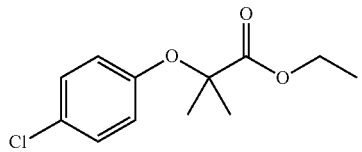 [SMILES: CCOC(=O)C(C)(C)Oc1ccc(Cl)cc1]

As used herein, the term "dopamine receptor antagonist" means a substance which has an inhibitory function on an action of dopamine to its receptor, for example, including a D1 receptor antagonist, and a D5 receptor antagonist.

As used herein, the term "D1 receptor antagonist" means a substance which has an inhibitory function on an action of dopamine to a D1 receptor. The D1 receptor antagonist includes benzazepine, fenoldopam, lorcaserin, SCH23390, SCH39166, LE300, and derivatives thereof, and pharmacologically acceptable salts thereof.

Benzazepine is represented by the formula:

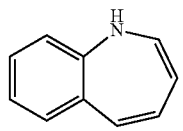 [SMILES: C1=CNc2ccccc2C=C1]

As used herein, the term "D5 receptor antagonist" means a substance which has an inhibitory function on an action of dopamine to a D5 receptor. The D5 receptor antagonist includes SCH39166 and derivatives thereof, and pharmacologically acceptable salts thereof.

SCH39166 is represented by the formula:

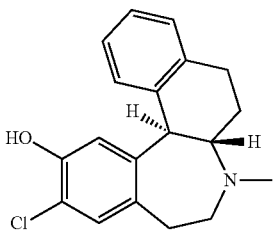 [SMILES: CN1CCc2cc(Cl)c(O)cc2[C@H]2c3ccccc3CC[C@@H]21]

As used herein, the term "dopamine receptor agonist" means a substance which has itself a function of acting on a dopamine receptor, for example, including a D2 receptor agonist, a D3 receptor agonist, and a D4 receptor agonist.

As used herein, the term "D2 receptor agonist" means a substance which has itself a function of acting on a D2 receptor. The D2 receptor agonist includes cabergoline, bromocriptine, pergolide, ropinirole, talipexole, aripiprazole, lurasidone, and derivatives thereof, and pharmacologically acceptable salts thereof.

Ropinirole is represented by the formula:

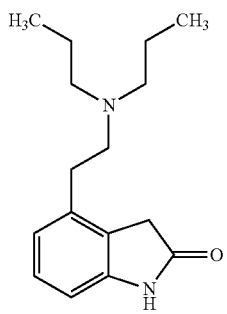

As used herein, the term "D3 receptor agonist" means a substance which has itself a function of acting on a D3 receptor. The D3 receptor agonist includes piribedil, rotigotine, PD1289077, OH-DPAT, and derivatives thereof, and pharmacologically acceptable salts thereof.

Rotigotine is represented by the formula:

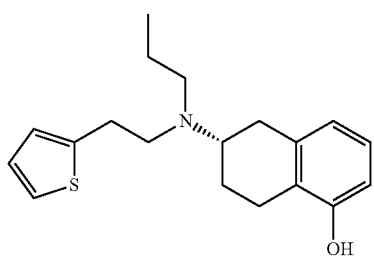 [SMILES: CCCN(CCc1cccs1)[C@H]1CCc2c(O)cccc2C1]

As used herein, the term "D4 receptor agonist" means a substance which has itself a function of acting on a D4 receptor. D4 receptor agonist includes flibanserin, ABT724, PD168077, CP226269, and derivatives thereof, and pharmacologically acceptable salts thereof.

Flibanserin is represented by the formula:

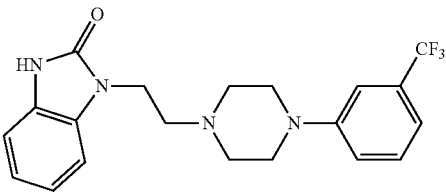 [SMILES: O=c1[nH]c2ccccc2n1CCN1CCN(c2cccc(C(F)(F)F)c2)CC1]

As used herein, the term "histamine receptor antagonist" means a substance which has an inhibitory function on an action of histamine to its receptor, for example, including an H1 receptor antagonist, and an H2 receptor antagonist.

As used herein, the term "H1 receptor antagonist" means a substance which has an inhibitory function on an action of histamine to an H1 receptor. The H1 receptor antagonist includes ketanserin, thonzylamine, mepyramine, tripelenamine, dimethindene, clemastine, bamipine, isothipendyl, chlorphenoxamine, dimetotiazine, chlorpromazine, hydroxyzine, opipramol, betahistine, cinnarizine, levocabastine, antazoline, diphenylpyraline, carbinoxamine, doxylamine, alimemazine, cyclizine, meclozine, levocetirizine, cyproheptadine, phenindamine, triprolidine, azatadine, astemizole, terfenadine, acrivastine, ebastine, desloratadine, rupatadine, bilastine, mizolastine, noberastine, rocastine, temelastine, bepotastine, diphenhydramine, chlorpheniramine, ketotifen, promethazine, cyproheptadine, epinastine, olopatadine, bepotastine, astemizole, emedastine, mequitazine, oxatomide, loratadine, fexofenadine, cetirizine, azelastine, and derivatives thereof, and pharmacologically acceptable salts thereof.

Diphenhydramine is represented by the formula:

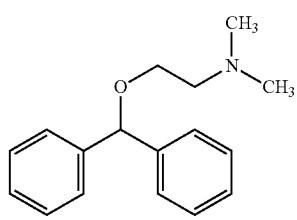 [SMILES: CN(C)CCOC(c1ccccc1)c1ccccc1]

As used herein, the term "H2 receptor antagonist" means a substance which has an inhibitory function on an action of histamine to an H2 receptor. The H2 receptor antagonist includes cimetidine, ranitidine, famotidine, nizatidine, roxatidine, lafutidine, and derivatives thereof, and pharmacologically acceptable salts thereof.

Famotidine is represented by the formula:

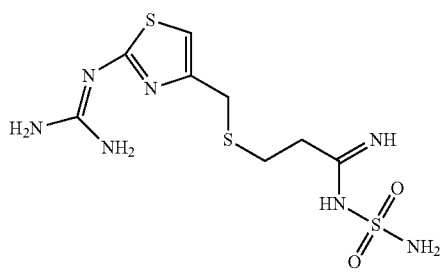 [SMILES: N=C(CCSCc1csc(N=C(N)N)n1)NS(N)(=O)=O]

As used herein, the term "histamine receptor agonist" means a substance which has itself a function of acting on a histamine receptor, for example, an H1 receptor agonist, an H3 receptor agonist, and an H4 receptor agonist.

As used herein, the term "H1 receptor agonist" means a substance which has itself a function of acting on an H1 receptor. The H1 receptor agonist includes 2-pyridylethylamine, 2-thiazolylethylamine, and derivatives thereof, and pharmacologically acceptable salts thereof.

2-pyridylethylamine is represented by the formula:

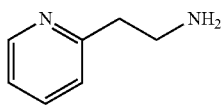

As used herein, the term "H3 receptor agonist" means a substance which has itself a function of acting on an H3 receptor. The H3 receptor agonist includes Immethridine, Imetit, Immepip, α-methylhistamine, proxifan, and derivatives thereof, and pharmacologically acceptable salts thereof.

Proxifan is represented by the formula:

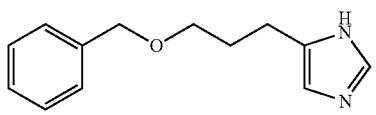 [SMILES: c1ccc(COCCCc2cnc[nH]2)cc1]

As used herein, the term "H4 receptor agonist" means a substance which has itself a function of acting on an H4 receptor. The H4 receptor agonist includes 4-methylhistamine, VUF8430, Immepip, and derivatives thereof, and pharmacologically acceptable salts thereof.

4-methylhistamine is represented by the formula:

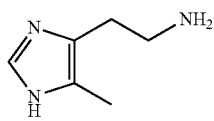

As used herein, the term "serotonin receptor antagonist" means a substance which has an inhibitory function on an action of serotonin to its receptor, for example, including a 5-HT2 receptor antagonist, a 5-HT4 receptor antagonist, a 5-HT6 receptor antagonist, and a 5-HT7 receptor antagonist.

As used herein, the term "5-HT2 receptor antagonist" means a substance which has an inhibitory function on an action of serotonin to a 5-HT2 receptor. The 5-HT2 receptor antagonist includes pizotifen, risperidone, olanzapine, quetiapine, aripiprazole, blonanserin, clozapine, paliperidone, ritanserin, yohimbine, mesulergine, agomelatine, cyclobenzaprine, sarpogrelate, methysergide, ketanserin and derivatives thereof, and pharmacologically acceptable salts thereof.

Olanzapine is represented by the formula:

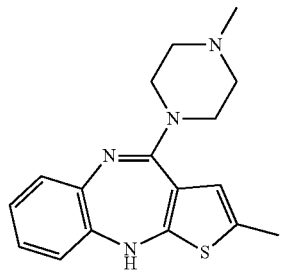 [SMILES: Cc1cc2c(s1)Nc1ccccc1N=C2N1CCN(C)CC1]

As used herein, the term "5-HT4 receptor antagonist" means a substance which has an inhibitory function on an action of serotonin to a 5-HT4 receptor. The 5-HT4 receptor antagonist includes piboserod, GR113808, GR125487, RS39604, SB204070, and derivatives thereof, and pharmacologically acceptable salts thereof.

Piboserod is represented by the formula:

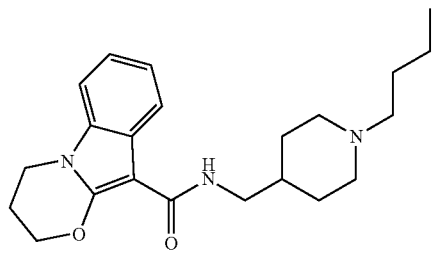 [SMILES: CCCCN1CCC(CNC(=O)c2c3n(c4ccccc24)CCCO3)CC1]

As used herein, the term "5-HT6 receptor antagonist" means a substance which has an inhibitory function on an action of serotonin to a 5-HT6 receptor. The 5-HT6 receptor antagonist includes cerlapirdine, clozapine, and derivatives thereof, and pharmacologically acceptable salts thereof.

Cerlapirdine is represented by the formula:

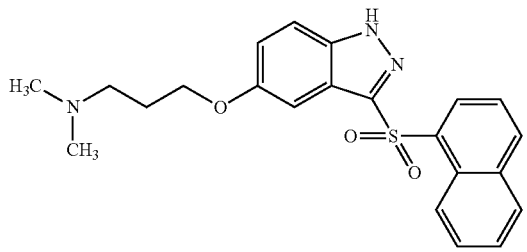 [SMILES: CN(C)CCCOc1ccc2[nH]nc(S(=O)(=O)c3cccc4ccccc34)c2c1]

As used herein, the term "5-HT7 receptor antagonist" means a substance which has an inhibitory function on an action of serotonin to a 5-HT7 receptor. The 5-HT7 receptor antagonist includes metergoline and derivatives thereof, and pharmacologically acceptable salts thereof.

Metergoline is represented by the formula:

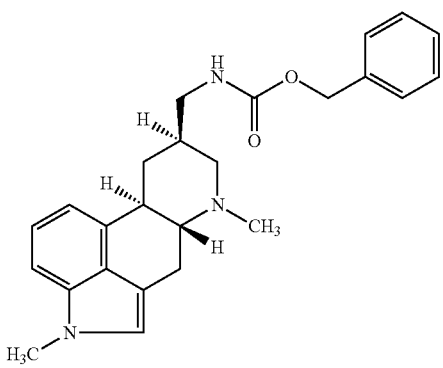 [SMILES: CN1C[C@H](CNC(=O)OCc2ccccc2)C[C@@H]2c3cccc4c3c(cn4C)C[C@H]21]

As used herein, the term "serotonin receptor agonist" means a substance which has itself a function of acting on a serotonin receptor, for example, including a 5-HT1 receptor agonist, and a 5-HT2 receptor agonist.

As used herein, the term "5-HT1 receptor agonist" means a substance which has itself a function of acting on a 5-HT1 receptor. The 5-HT1 receptor agonist includes piclozotan, tandospirone, sumatriptan, zolmitriptan, eletriptan, rizatriptan, naratriptan, almotriptan, frovatriptan, avitriptan, ergotamine, ergot alkaloid, and derivatives thereof, and pharmacologically acceptable salts thereof.

Zolmitriptan is represented by the formula:

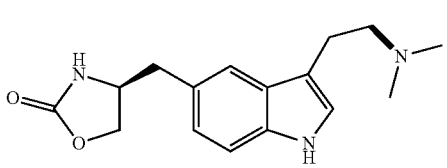

As used herein, the term "5-HT2 receptor agonist" means a substance which has itself a function of acting on a 5-HT2 receptor. The 5-HT2 receptor agonist includes α-methyl-5-HT, agomelatine, norfenfluramine, meta-chlorophenyl piperazine, and derivatives thereof, and pharmacologically acceptable salts thereof.

Agomelatine is represented by the formula:

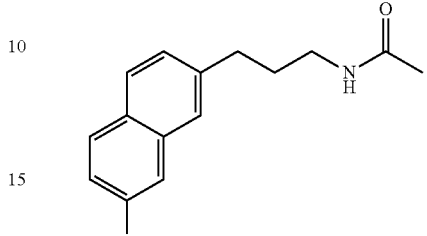

As used herein, the term "vasopressin receptor antagonist" means a substance which has an inhibitory function on an action of vasopressin to its receptor, for example, including a V2 receptor antagonist.

As used herein, the term "V2 receptor antagonist" means a substance which has an inhibitory function on an action of vasopressin to a V2 receptor. The V2 receptor antagonist includes tolvaptan, mozavaptan, conivaptan, lixivaptan, and derivatives thereof, and pharmacologically acceptable salts thereof.

Mozavaptan is represented by the formula:

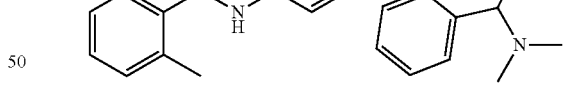

As used herein, the term "vasopressin receptor agonist" means a substance which has itself a function of acting on a vasopressin receptor, for example, including a V1 receptor agonist.

As used herein, the term "V1 receptor agonist" means a substance which has itself a function of acting on a V1 receptor. The V1 receptor agonist includes vasopressin, felypressin, desmopressin, lypressin, terlipressin, ornipressin, argipressin, and derivatives thereof, and pharmacologically acceptable salts thereof.

Desmopressin is represented by the formula:

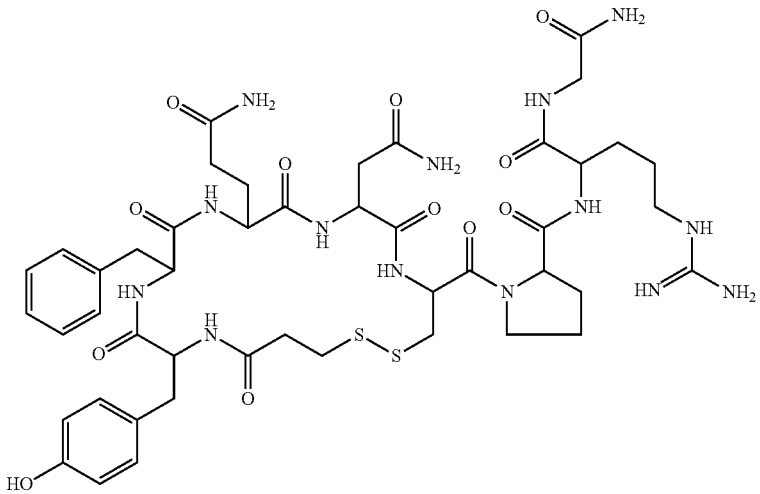 [SMILES: N=C(N)NCCCC(NC(=O)C1CCCN1C(=O)C1CSSCCC(=O)NC(Cc2ccc(O)cc2)C(=O)NC(Cc2ccccc2)C(=O)NC(CCC(N)=O)C(=O)NC(CC(N)=O)C(=O)N1)C(=O)NCC(N)=O]

As used herein, the term "muscarine receptor antagonist" means a substance which has an inhibitory function on an action of acetylcholine to a muscarine receptor, for example, an M1 receptor antagonist, an M3 receptor antagonist, and an M5 receptor antagonist.

As used herein, the term "M1 receptor antagonist" means a substance which has an inhibitory function on an action of acetylcholine to a M1 receptor. The term "M3 receptor antagonist" means a substance which has an inhibitory function on an action of acetylcholine to an M3 receptor. The term "M5 receptor antagonist" means a substance which has an inhibitory function on an action of acetylcholine to an M5 receptor. The M1 receptor antagonist, and/or the M3 receptor antagonist, and/or the M5 receptor antagonist includes pirenzepine, atropin, trimebutine, piperidolate, oxybutynin, tropicamide, propiverine, tolterodine, solifenacin, darifenacin, imidafenacin, oxyphencyclimine, tiotropium bromide, S-oxybutynin, tiquizium, and derivatives thereof, and pharmacologically acceptable salts thereof.

Oxybutynin is represented by the formula:

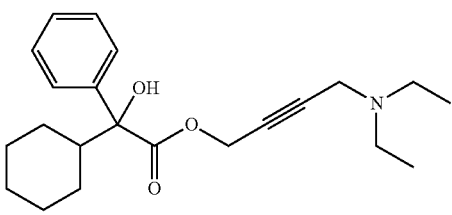 [SMILES: CCN(CC)CC#CCOC(=O)C(O)(c1ccccc1)C1CCCCC1]

As used herein, the term "muscarine receptor agonist" means a substance which has itself a function of acting on a muscarine receptor, for example, including an M1 receptor agonist, an M2 receptor agonist, an M3 receptor agonist, an M4 receptor agonist, and an M5 receptor agonist.

As used herein, the term "M1 receptor agonist" means a substance which has itself a function of acting on an M1 receptor. The term "M2 receptor agonist" means a substance which has itself a function of acting on an M2 receptor. The term "M3 receptor agonist" means a substance which has itself a function of acting on an M3 receptor. The term "M4 receptor agonist" means a substance which has itself a function of acting on an M4 receptor. The term "M5 receptor agonist" means a substance which has itself a function of acting on an M5 receptor. The M1 receptor agonist, and/or the M2 receptor agonist, and/or the M3 receptor agonist, and/or the M4 receptor agonist, and/or the M5 receptor agonist includes acetylcholine, aceclidine, albamelin, talsaclidine, xanomeline, pilocarpine, cevimeline, bethanechol, mazaticol, muscarine, and derivatives thereof, and pharmacologically acceptable salts thereof.

Bethanechol is represented by the formula:

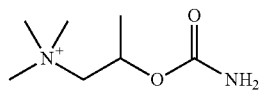

As used herein, the term "adrenergic receptor antagonist" means a substance which has an inhibitory function on an action of adrenaline to its receptor, for example, including an α1 receptor antagonist, a β1 receptor antagonist, a β2 receptor antagonist, and a β3 receptor antagonist.

As used herein, the term "α1 receptor antagonist" means a substance which has an inhibitory function on an action of adrenaline to an α1 receptor. The α1 receptor antagonist includes prazosin, doxazosin, bunazosin, trimazosin, alfuzosin, silodosin, terazosin, tamsulosin, and derivatives thereof, and pharmacologically acceptable salts thereof.

Tamsulosin is represented by the formula:

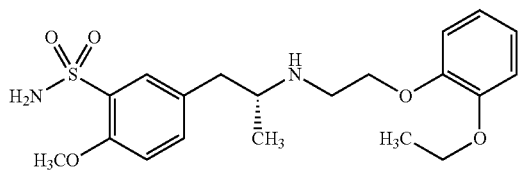 [SMILES: CCOc1ccccc1OCCN[C@H](C)Cc1ccc(OC)c(S(N)(=O)=O)c1]

As used herein, the term "β1 receptor antagonist" means a substance which has an inhibitory function on an action of adrenaline to a β1 receptor. The term "β2 receptor antagonist" means a substance which has an inhibitory function on an action of adrenaline to a β2 receptor. The term "β3 receptor antagonist" means a substance which has an inhibitory function on an action of adrenaline to a β3 receptor. The β1 receptor antagonist, and/or the β2 receptor antagonist, and/or the β3 receptor antagonist includes bopindolol, pindolol, timolol, dichloroisoprenaline, alprenolol, carteolol, indenolol, bunitrolol, penbutolol, propranolol, nadolol, nipradilol, tilisolol, acebutolol, celiprolol, metoprolol, atenolol, bisoprolol, betaxolol, practolol, bevantolol, butoxamine, carvedilol, amosulalol, arotinolol, labetalol, and derivatives thereof, and pharmacologically acceptable salts thereof.

Propranolol is represented by the formula:

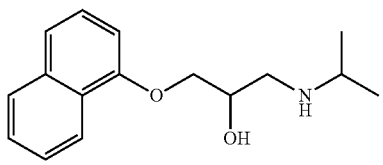 [SMILES: CC(C)NCC(O)COc1cccc2ccccc12]

As used herein, the term "angiotensin receptor agonist" means a substance which has itself a function of acting on an angiotensin receptor, for example, including an AT2 receptor agonist.

As used herein, the term "adrenergic receptor agonist" means a substance which has itself a function of acting on an adrenergic receptor, for example, including an α1 receptor agonist, and an α2 receptor agonist.

As used herein, the term "α1 receptor agonist" means a substance which has itself a function of acting on anal receptor. The term "α2 receptor agonist" means a substance which has itself a function of acting on an α2 receptor. The α1 receptor agonist, and/or the α2 receptor agonist includes norepinephrine, norfenefrine, etilefrine, naphazoline, phenylephrine, midodrine, methoxamine, oxedrine, metaraminol, arbutamine, ephedrine, oxymetazoline, tetryzoline, xylometazoline, tramazoline, pseudoephedrine, dipivefrin, aminophylline, methylephedrine, rilmenidine, brimonidine, medetomidine, xylazine, tizanidine, guanfacine, methyldopa, guanabenz, and derivatives thereof, and pharmacologically acceptable salts thereof.

Xylazine is represented by the formula:

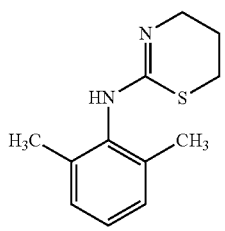

As used herein, the term "angiotensin receptor agonist" means a substance which has itself a function of acting on an angiotensin receptor, for example, including an AT2 receptor agonist.

As used herein, the term "AT2 receptor agonist" means a substance which has itself a function of acting on an AT2 receptor. The AT2 receptor agonist includes novokinin, angiotensin, and derivatives thereof, and pharmacologically acceptable salts thereof.

Angiotensin is represented by the formula:

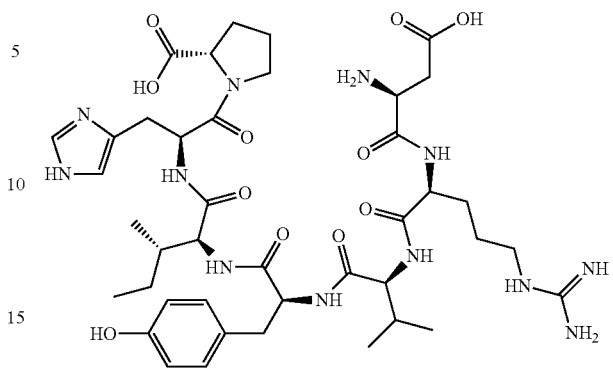

As used herein, the term "GABA receptor agonist" means a substance which has itself a function of acting on a GABA receptor, for example, including a $GABA_B$ receptor agonist.

As used herein, the term "$GABA_B$ receptor agonist" means a substance which has itself a function of acting on a $GABA_B$ receptor. The $GABA_B$ receptor agonist includes baclofen, γ-aminobutyric acid, albaclofen, and derivatives thereof, and pharmacologically acceptable salts thereof.

Baclofen is represented by the formula:

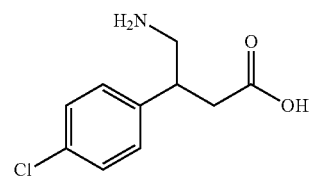 [SMILES: NCC(CC(=O)O)c1ccc(Cl)cc1]

As used herein, the term "thrombin receptor antagonist" means a substance which has an inhibitory function on an action of thrombin to its receptor, for example, including a PAR-1 receptor antagonist.

As used herein, the term "PAR-1 receptor antagonist" means a substance which has an inhibitory function on an action of thrombin to a PAR-1 receptor. The PAR-1 receptor antagonist includes vorapaxar, atopaxar, FR171113, RWJ56110, dabigatran, dabigatran etexilate, melagatran, ximelagatran, hirudin, hirolog, argatroban, and derivatives thereof, and pharmacologically acceptable salts thereof.

Vorapaxar is represented by the formula:

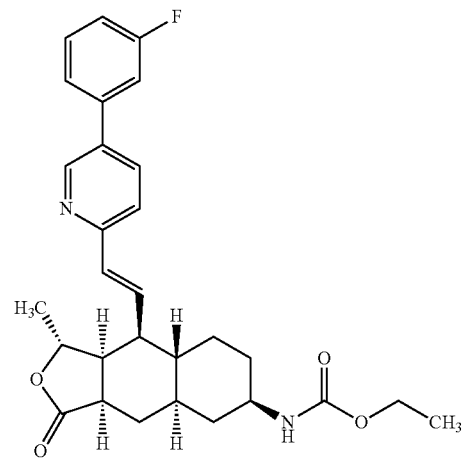 [SMILES: CCOC(=O)N[C@@H]1CC[C@@H]2[C@@H](C1)C[C@H]1C(=O)O[C@H](C)[C@H]1[C@H]2/C=C/c1ccc(-c2cccc(F)c2)cn1]

As used herein, the term "thrombin receptor agonist" means a substance which has itself a function of acting on a thrombin receptor, for example, including a PAR-1 receptor agonist.

As used herein, the term "PAR-1 receptor agonist" means a substance which has itself a function of acting on a PAR-1 receptor. The PAR-1 receptor agonist includes TRAP-6, TRAP-14, NAT6-NH$_2$, and derivatives thereof, and pharmacologically acceptable salts thereof.

TRAP-6 is represented by the formula:

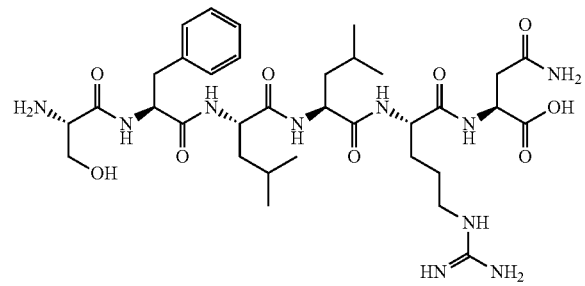 [SMILES: CC(C)C[C@H](NC(=O)[C@H](CC(C)C)NC(=O)[C@H](Cc1ccccc1)NC(=O)[C@@H](N)CO)C(=O)N[C@@H](CCCNC(=N)N)C(=O)N[C@@H](CC(N)=O)C(=O)O]

As used herein, the term "opioid receptor agonist" means a substance which has itself a function of acting on an opioid receptor. The opioid receptor agonist includes trimebutine, alvimopan, morphine, oxycodone, dihydrocodeine, diamorphine, pethidine, pentazocine, buprenorphine, butorphanol, nalbuphine, tilidine, dezocine, meptazinol, tapentadol, naltrexone, methadone, ethylmorphine, hydrocodone, acetyldihydrocodeine, nalorphine, loperamide, remoxipride, opipramol, and derivatives thereof, and pharmacologically acceptable salts thereof.

Buprenorphine is represented by the formula:

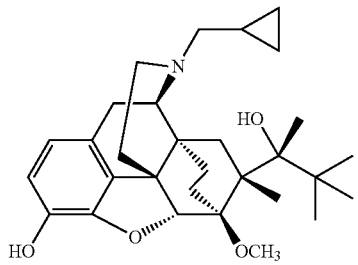 [SMILES: CO[C@]12CC[C@@]3(C[C@]1(C)[C@](C)(O)C(C)(C)C)[C@H]1Cc4ccc(O)c5c4[C@@]3(CCN1CC1CC1)[C@H]2O5]

As used herein, the term "leukotriene receptor antagonist" means a substance which has an inhibitory function on an action of leukotriene to its receptor, for example, including a CysLT1 receptor antagonist, and a CysLT2 receptor antagonist.

As used herein, the term "CysLT1 receptor antagonist" means a substance which has an inhibitory function on an action of leukotriene to a CysLT1 receptor. The term "CysLT2 receptor antagonist" means a substance which has an inhibitory function on an action of leukotriene to a CysLT2 receptor. The CysLT1 receptor antagonist, and/or the CysLT2 receptor antagonist includes montelukast, zafirlukast, pranlukast, and derivatives thereof, and pharmacologically acceptable salts thereof. For example, the pharmacologically acceptable salt of montelukast includes montelukast sodium.

Montelukast sodium is represented by the formula:

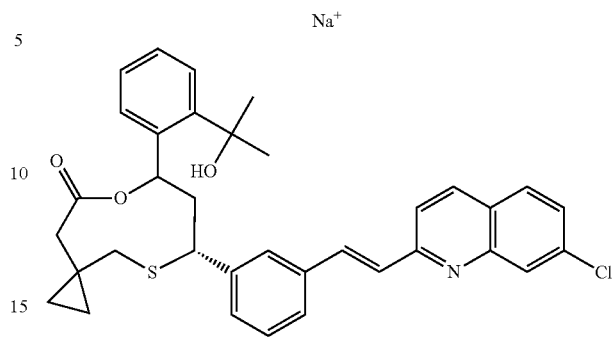

As used herein, the term "leukotriene receptor agonist" means a substance which has itself a function of acting on a leukotriene receptor, for example, including a BLT receptor agonist.

As used herein, the term "BLT receptor agonist" means a substance which has itself a function of acting on a BLT receptor. The BLT receptor agonist includes leukotriene B4, CAY10583, and derivatives thereof, and pharmacologically acceptable salts thereof.

Leukotriene B4 is represented by the formula:

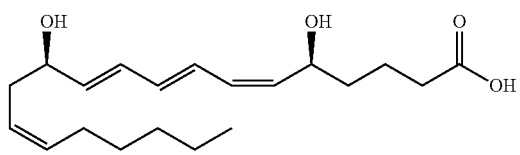 [SMILES: CCCCC/C=C\C[C@@H](O)/C=C/C=C/C=C\[C@@H](O)CCCC(=O)O]

As used herein, the term "ADP receptor agonist" means a substance which has itself a function of acting on an ADP receptor. The ADP receptor agonist includes adenosine diphosphate, and derivatives thereof, and pharmacologically acceptable salts thereof.

Adenosine diphosphate is represented by the formula:

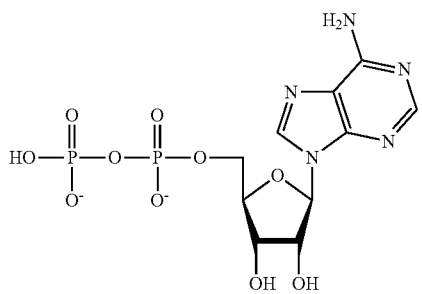

As used herein, the term "melatonin receptor agonist" means a substance which has itself a function of acting on a melatonin receptor. The melatonin receptor agonist includes melatonin, perlapine, tasimelteon, and derivatives thereof, and pharmacologically acceptable salts thereof.

Melatonin is represented by the formula:

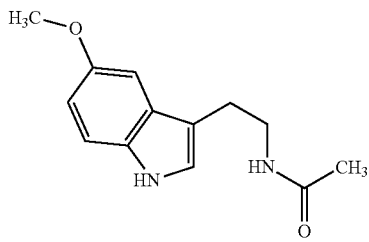 [SMILES: COc1ccc2[nH]cc(CCNC(C)=O)c2c1]

As used herein, the term "somatostatin receptor agonist" means a substance which has itself a function of acting on a somatostatin receptor. The somatostatin receptor agonist includes somatostatin, somatostatin-14, octreotide, and derivatives thereof, and pharmacologically acceptable salts thereof.

Octreotide is represented by the formula:

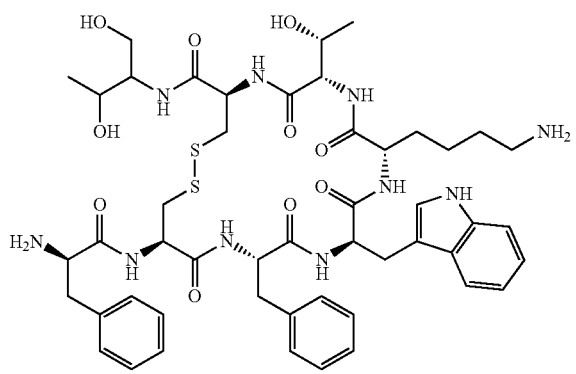 [SMILES: CC(O)C(CO)NC(=O)[C@@H]1CSSC[C@H](NC(=O)[C@H](N)Cc2ccccc2)C(=O)N[C@@H](Cc2ccccc2)C(=O)N[C@H](Cc2c[nH]c3ccccc23)C(=O)N[C@@H](CCCCN)C(=O)N[C@@H]([C@@H](C)O)C(=O)N1]

As used herein, the term "cannabinoid receptor agonist" means a substance which has itself a function of acting on a cannabinoid receptor. The cannabinoid receptor agonist includes dronabinol, nabilone, levonantradol, otenabant, GW833972A, GW405833, and derivatives thereof, and pharmacologically acceptable salts thereof.

Dronabinol is represented by the formula:

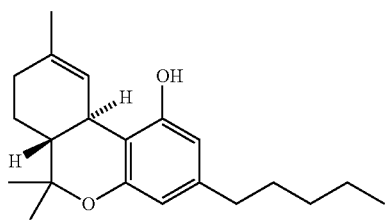 [SMILES: CCCCCc1cc(O)c2c(c1)OC(C)(C)[C@@H]1CCC(C)=C[C@@H]21]

As used herein, the term "sphingosine-1 phosphate receptor agonist" means a substance which has itself a function of acting on a sphingosine-1 phosphate receptor. The sphingosine-1 phosphate receptor agonist includes fingolimod, ponesimod, RPC-1063, ONO-4641, SEW2871, sphingosine-1 phosphate, and derivatives thereof, and pharmacologically acceptable salts thereof.

Fingolimod is represented by the formula:

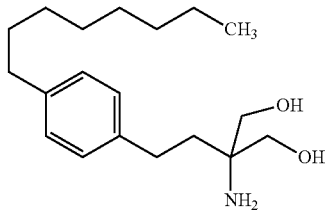 [SMILES: CCCCCCCCc1ccc(CCC(N)(CO)CO)cc1]

As used herein, the term "metabotropic glutamate receptor agonist" means a substance which has itself a function of acting on a metabotropic glutamate receptor, for example, including an mGluR2 receptor agonist, an mGluR3 receptor agonist, an mGluR4 receptor agonist, an mGluR6 receptor agonist, an mGluR7 receptor agonist, and an mGluR8 receptor agonist.

As used herein, the term "mGluR2 receptor agonist" means a substance which has itself a function of acting on an mGluR2 receptor. The term "mGluR3 receptor agonist" means a substance which has itself a function of acting on an mGluR3 receptor. The term "mGluR4 receptor agonist" means a substance which has itself a function of acting on an mGluR4 receptor. The term "mGluR6 receptor agonist" means a substance which has itself a function of acting on an mGluR6 receptor. The term "mGluR7 receptor agonist" means a substance which has itself a function of acting on an mGluR7 receptor. The term "mGluR8 receptor agonist" means a substance which has itself a function of acting on an mGluR8 receptor. The mGluR2 receptor agonist, and/or the mGluR3 receptor agonist, and/or the mGluR4 receptor agonist, and/or the mGluR6 receptor agonist, and/or the mGluR7 receptor agonist, and/or the mGluR8 receptor agonist includes VUO361737, VU0155041, biphenylindanone A, PBDA, L-AP4, and derivatives thereof, and pharmacologically acceptable salts thereof.

VUO361737 is represented by the formula:

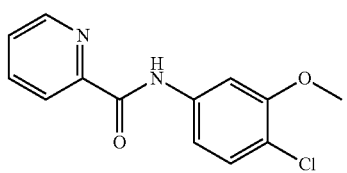 [SMILES: COc1cc(NC(=O)c2ccccn2)ccc1Cl]

As used herein, the term "phospholipase A2 inhibitor" means a substance which has an inhibitory function on an activity of phospholipase A2. The phospholipase A2 inhibitor includes glycyrrhizic acid, glycyrrhetic acid, and derivatives thereof, and pharmacologically acceptable salts thereof.

Glycyrrhetic acid is represented by the formula:

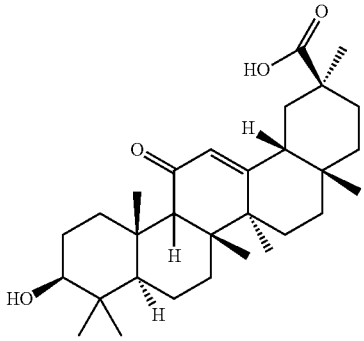

As used herein, the term "TGF-β production inhibitor" means a substance which has an inhibitory function on production of TGF-β. The TGF-β production inhibitor includes pirfenidone, tranilast, and derivatives thereof, and pharmacologically acceptable salts thereof.

Pirfenidone is represented by the formula:

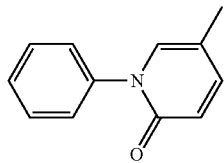

As used herein, the term "Th2 cytokine inhibitor" means a substance which has an inhibitory function on production of a Th2 cytokine such as IL-4 and IL-5. The Th2 cytokine inhibitor includes suplatast and derivatives thereof, and pharmacologically acceptable salts thereof. The pharmacologically acceptable salt of suplatast includes, for example, suplatast tosilate. In a preferred aspect of the invention, the Th2 cytokine inhibitor is suplatast tosilate.

Suplatast tosilate is represented by the formula:

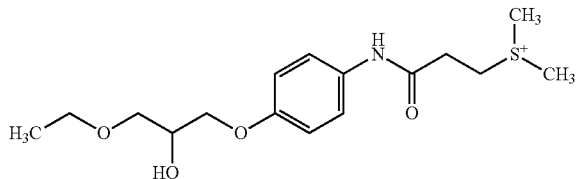

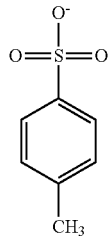

As used herein, the term "TLR ligand" means a ligand for a Toll-like receptor (TLR), for example, including a ligand for TLR1-9. The TLR ligand includes a TLR1/2 ligand, a TLR2/6 ligand, a TLR2 and Dectin1 ligand, a TLR3 ligand, a TLR4 ligand, a TLR5 ligand, a TLR7 ligand and/or a TLR8 ligand, and a TLR9 ligand. In a preferred aspect of the invention, the TLR ligand is a TLR1/2 ligand, a TLR2 and Dectin1 ligand, a TLR3 ligand, a TLR4 ligand, a TLR7 ligand and/or a TLR8 ligand, and/or a TLR9 ligand.

As used herein, the term "TLR1/2 ligand" means a ligand for a heterodimer of a Toll-like receptor (TLR) 1 and a Toll-like receptor (TLR)$_2$, for example, triacylated lipoprotein derived from bacteria cell walls and salts thereof, they may be an extract, a product, or a synthetic compound thereof, without limitation.

In a preferred aspect of the invention, the TLR1/2 ligand is Pam$_3$CSK$_4$. Pam$_3$CSK$_4$ has the formula ("Ser-Lys-Lys-Lys-Lys" disclosed as SEQ ID NO: 17):

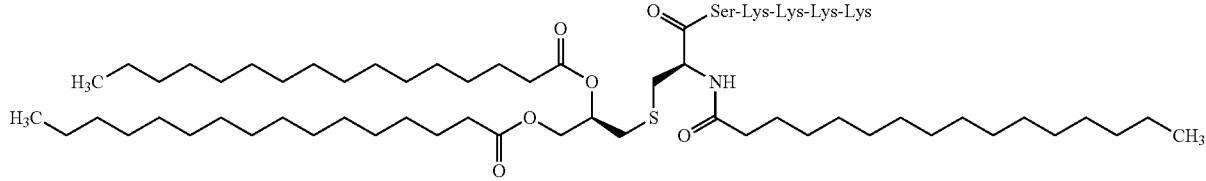

As used herein, the term "TLR2 and Dectin1 ligand" means a ligand for a Toll-like receptor (TLR) 2 and a β1,3-glucan receptor (Dectin1), for example, including a β1,3-glucan derived from cell walls of fungus and salts thereof. They may be an extract, a product, or a synthetic compound thereof, without limitation. In a preferred aspect of the invention, the TLR2 and Dectin 1 ligand is Zymosan derived from cell walls of yeast.

As used herein, the term "TLR3 ligand" means a ligand for a Toll-like receptor (TLR) 3, for example, including a double-stranded RNA (dsRNA) derived from virus and salts thereof. They may be an extract, a product, or a synthetic compound thereof, without limitation. In a preferred aspect of the invention, the TLR3 ligand is a synthetic compound polyinosinic-polycytidylic acid (Poly (I:C)) and/or salts thereof.

As used herein, the term "TLR4 ligand" means a ligand for a Toll-like receptor (TLR) 4, for example, a lipopolysaccharide (LPS) derived from bacteria or plants, in particular, lipid A derivatives, for example, monophosphoryl lipid A, 3 deacylated monophosphoryl lipid A (3D-MPL), OM174, OM 294 DP, or OM 197 MP-Ac DP, alkyl glucosaminide phosphate (AGP), for example, AGP as disclosed in WO 9850399 or U.S. Pat. No. 6,303,347 or AGP salt as disclosed in U.S. Pat. No. 6,764,840. Further, the ligand includes lipopolysaccharide derived from *Pantoea*, glucopyranosyl lipid, sodium hyaluronate, without limitation.

In a preferred aspect of the invention, the TLR4 ligand is preferably a lipopolysaccharide derived from *Acetobacter* genus (for example, *Acetobacter aceti, Acetobacter xylinum, Acetobacter orientalis*), *Zymomonas* genus (for example, *Zymomonas mobilis*), *Xanthomonas* genus (for example, *Xanthomonas campestris*), *Enterobacter* genus (for example, *Enterobacter cloacae*), *Pantoea* genus (for example, *Pantoea agglomerans*). An extract of the lipopolysaccharide or purified lipopolysaccharide can be used as such. Further, for example, the lipopolysaccharide derived from *Pantoea agglomerans* (IP-PA1) is commercially available from Funakoshi Co., Ltd. Further, in a preferred aspect of the invention, the TLR4 ligand is a lipopolysaccharide derived from *Pantoea*, a glucopyranosyl lipid, and/or a sodium hyaluronate.

As used herein, the term "TLR7 and/or TLR8 ligand" means a ligand for a Toll-like receptor (TLR)$_7$ and/or TLR8, for example, including a single-stranded RNA, imiquimod, resiquimod (R848), TLR7-II, and other compounds, for example, loxoribine and bropirimine, without limitation.

In a preferred aspect of the invention, the TLR7 ligand and/or the TLR8 ligand is imiquimod. Imiquimod is 1-(2-methylpropyl)-1H-imidazo[4,5-c]quinoline-4-amine having the formula:

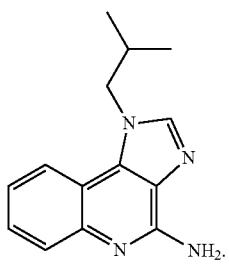 [SMILES: CC(C)Cn1cnc2c(N)nc3ccccc3c21]

For example, Japanese Unexamined Patent Application Publication (Translation of PCT Application) No. H07-505883 (Patent Document 4) describes the characteristics and a method for producing it.

In another preferred aspect, the TLR7 ligand and/or the TLR8 ligand is resiquimod. Resiquimod is 4-amino-2-(ethoxymethyl)-α,α-dimethyl-1H-imidazo[4,5-c]quinoline-1-ethanol having the formula:

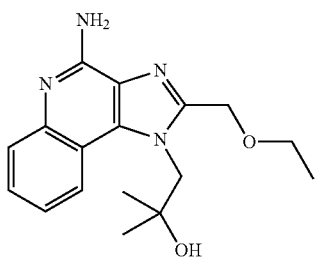 [SMILES: CCOCc1nc2c(N)nc3ccccc3c2n1CC(C)(C)O]

In another preferred aspect, the TLR7 ligand and/or the TLR8 ligand is TLR7-II. TLR7-II is represented by the formula:

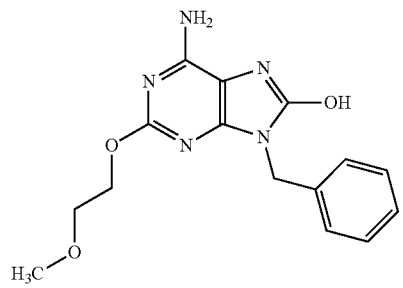 [SMILES: COCCOc1nc(N)c2nc(O)n(Cc3ccccc3)c2n1]

In another preferred aspect, the TLR7 ligand and/or the TLR8 ligand is bropirimine. Bropirimine is represented by the formula:

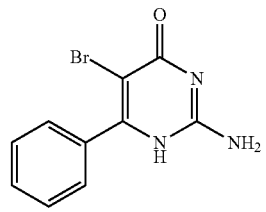 [SMILES: Nc1nc(=O)c(Br)c(-c2ccccc2)[nH]1]

As used herein, the term "TLR9 ligand" means a ligand for a Toll-like receptor (TLR) 9, for example, including ODN1826. The TLR9 ligand used in the invention may be an extract, a product, or a synthetic compound thereof, without limitation. In a preferred aspect of the invention, TLR9 ligand is ODN1826.

ODN1826 is an oligodeoxynucleotide having the following sequence (SEQ ID NO: 12):

```
5'-tccatgacgttcctgacgtt-3'
```

As used herein, the term "TLR2/6 ligand" means a ligand of a heterodimer for a Toll-like receptor (TLR) 2 and a Toll-like receptor (TLR) 6, for example, including a diacylated lipoprotein derived from cell walls of mycoplasma and salts thereof. They may be an extract, a product, or a synthetic compound thereof, without limitation. In a preferred aspect of the invention, the TLR2/6 ligand is Pam$_2$CSK$_4$, MALP-2 and/or FSL-1.

Pam$_2$CSK$_4$ is represented by the following formula ("Ser-Lys-Lys-Lys-Lys" disclosed as SEQ ID NO: 17):

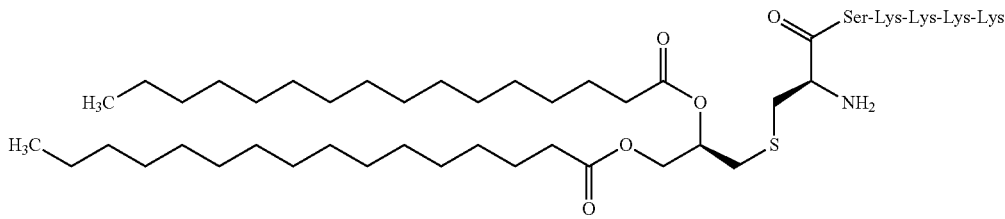

FSL-1 is represented by the following formula ("Gly-Asp-Pro-Lys-His-Pro-Lys-Ser-Phe" disclosed as SEQ ID NO: 18):

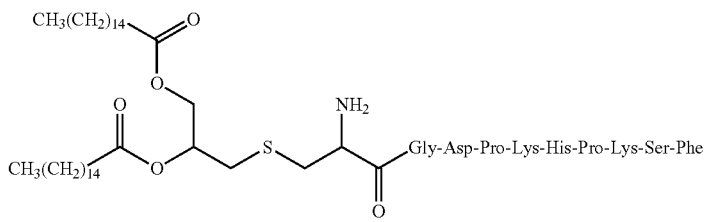

As used herein, the term "TLR5 ligand" means a ligand for a Toll-like receptor (TLR) 5, for example, including flagellin. The TLR5 ligand used in the invention may be an extract, a product, or a synthetic compound thereof, without limitation. In a preferred aspect of the invention, TLR5 ligand is flagellin.

The Toll-like receptor (TLR) is a family of type I transmembrane protein in which the in vivo activation initiates an innate immune response involving a specific cytokine, a chemokine and a growth factor. All TLR can activate a certain intracellular signaling molecule, for example, nuclear factor κB (NF-κB) and mitogen-activated protein kinase (MAP kinase), while the specific population of the released cytokine and chemokine is likely to be unique for each TLR. The TLR3, 7, 8, and 9 includes a subfamily of TLR presented in the endosome area or the lysosome area of immune cells (dendritic cells and monocytes). Specifically, the TLR3 is expressed by various cells including dendritic cells or fibroblasts. The TLR7 is expressed by plasmacytoid dendritic cells, and expressed by monocytes in relatively small level. The TLR8 is expressed by monocytes and monocyte derived dendritic cells and myeloid dendritic cells. The TLR9 is expressed by plasmacytoid dendritic cells. The subfamily mediates the recognition of a microorganism nucleic acid (such as a single-stranded RNA, a double-stranded RNA, or a single-stranded DNA). The TLR3, TLR7 and/or TLR8, TLR9 agonist stimulates the production of various inflammatory cytokines (for example, including interleukin-6, interleukin-12, TNF-α, and interferon-γ). The agonist further promotes to increase the expression of a co-stimulatory molecule (for example, CD40, CD80, and CD86), a major histocompatibility complex molecule, and a chemokine receptor. An type I interferon (IFNα and IFNβ) is further produced by cells during the activation of the TLR7 and/or TLR8 agonist.

As used herein, the term "cyclic dinucleotide" means a cyclized molecule in which each 2 OH groups in the saccharide moieties of two nucleotides forms esters with the same phosphate molecule, and derivatives thereof, for example, including a cyclic diAMP(c-di-AMP), a cyclic diGMP(c-di-GMP), a c-dGpGp, a c-dGpdGp, a c-GpAp, a c-GpCp, and a c-GpUp, without limitation. The cyclic dinucleotide activates dendritic cells or T cells. Further examples of the cyclic dinucleotide, the usability of the cyclic dinucleotide as an adjuvant, and a method for producing thereof are described in Japanese Unexamined Patent Application Publication (Translation of PCT Application) No. 2007-529531 (Patent Document 5). In a preferred aspect of the invention, the cyclic dinucleotide is a cyclic diGMP and/or a cyclic diAMP. The cyclic diGMP has the formula.

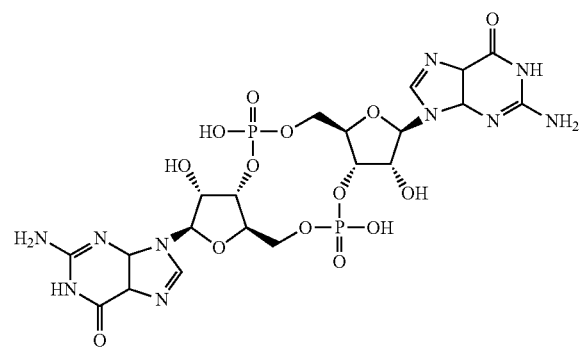 [SMILES: NC1=NC2C(N=CN2[C@@H]2O[C@@H]3COP(=O)(O)O[C@H]4[C@@H](O)[C@H](N5C=NC6C(=O)NC(N)=NC65)O[C@@H]4COP(=O)(O)O[C@H]3[C@H]2O)C(=O)N1]

The synthesis method is described in Kawai et al., Nucleic Acids Research Suppl. 3:103-4.

As used herein, the term "helper peptide" means any peptide which activates helper T cells, for example, including a helper peptide derived from tuberculosis, a helper peptide derived from measles virus, a helper peptide derived from Hepatitis B virus, a helper peptide derived from hepatitis C virus, a helper peptide derived from *Chlamydia trachomatis*, a helper peptide derived from *P. falciparum* sporozoite, a helper peptide derived from keyhole limpet haemocyanin, a helper peptide derived from tetanus toxin, a helper peptide derived from pertussis toxin, a helper peptide derived from diphtheria toxin, a helper peptide derived from cancer cell (for example, an IMA-MMP-001 helper peptide, a CEA-006 helper peptide, an MMP-001 helper peptide, a TGFBI-004 helper peptide, an HER-2/neu(aa776-790) helper peptide, an AE36 helper peptide, an AE37 helper peptide, an MET-005 helper peptide, a BIR-002 helper peptide), and universal helper analogs (for example, PADRE).

Further, in the invention, in place of the helper peptide, or in combination therewith, peptides in which all or a part of amino acids of the helper peptides are modified by substitution, modification, or the like (hereinafter, referred to as "modified helper peptide") can also be used.
The modified helper peptides include, for example,
(a) a peptide consisting of an amino acid sequence in which one to several, for example, 1, 2, 3, 4 or 5 amino acids are substituted, deleted or added, in an amino acid sequence of the original helper peptide; and
(b) a peptide consisting of an amino acid sequence in which all or apart of amino acids, for example, one or more, for example, 1, 2, 3, 4, 5, 6, 7, 8, 9, 10, 11, 12, 13, 14, or 15 amino acids are modified, in an amino acid sequence of the original helper peptide.

Examples of the "modification" of an amino acid which can be possessed by the modified helper peptide include, but are not limited to, acetylation, alkylation such as methylation, glycosylation, hydroxylation, carboxylation, aldehyde formation, phosphorylation, sulfonylation, formylation, modification by aliphatic chain addition such as myristoylation, palmitoylation, or stearoylation, octanolyation, esterification, amidation, deamidation, modification by disulfide bond formation such as cystine modification, glutathione modification, or thioglycolic acid modification, glycosylation, ubiquitination, succinimide formation, glutamylation, prenylation, and the like. The modified helper peptide may include a combination of a substitution, deletion, or addition of at least one amino acid, and a modification of at least one amino acid.

In a preferable aspect of the present invention, the helper peptide consists of 10 to 18 amino acids, preferably 12 to 16 amino acids, more preferably 13 to 15 amino acids. In a preferred aspect of the invention, the helper peptide is Peptide-25 or a modified Peptide-25, or PADRE. An example of the modified Peptide-25 is Peptide-25B. Peptide-25 is a peptide of 15 amino acids consisting of a sequence Phe Gln Asp Ala Tyr Asn Ala Ala Gly Gly His Asn Ala Val Phe (SEQ ID NO: 13), the sequence corresponds to the amino acid residue 240-254 of Ag85B, the major protein secreted by human-type tuberculosis (*Mycobacterium tuberculosis*). Peptide-25B is an example of the modified Peptide-25 in which a part of amino acids of the Peptide-25 was modified in order to increase immunostimulatory effect. Peptide-25B is a peptide of 15 amino acids consisting of a sequence Phe Gln Asp Ala Tyr Asn Ala Val His Ala Ala His Ala Val Phe (SEQ ID NO: 14). PADRE is a peptide of 13 amino acids consisting of a sequence D-Ala Lys cyclohexyl-Ala Val Ala Ala Trp Thr Leu Lys Ala Ala D-Ala (Herein referred as SEQ ID NO: 15).

As used herein, the term "immunomodulatory small molecule drug" means a substance which activates or inhibits immune cells, such as T cells, NK cells, or macrophages, and which does not correspond to any of the aforementioned TLR ligand, the cyclic dinucleotide, the helper peptide, the cyclooxygenase inhibitor, the prostaglandin receptor antagonist, the prostaglandin receptor agonist, the TSLP production inhibitor, the adenylate cyclase inhibitor, the omega-3 fatty acid, the PPAR agonist, the dopamine receptor antagonist, the dopamine receptor agonist, the histamine receptor agonist, the histamine receptor antagonist, the serotonin receptor agonist, the serotonin receptor antagonist, the vasopressin receptor antagonist, the vasopressin receptor agonist, the muscarine receptor antagonist, the muscarine receptor agonist, the adrenergic receptor antagonist, the adrenergic receptor agonist, the angiotensin receptor agonist, the GABA receptor agonist, the thrombin receptor antagonist, the thrombin receptor agonist, the opioid receptor agonist, the ADP receptor agonist, the leukotriene receptor antagonist, the leukotriene receptor agonist, the melatonin receptor agonist, the somatostatin receptor agonist, the cannabinoid receptor agonist, the sphingosine-1 phosphate receptor agonist, the metabotropic glutamate receptor agonist, the phospholipase A2 inhibitor, the TGF-β production inhibitor, and Th2 cytokine inhibitor. The immunomodulatory small molecule drug includes, for example, bestatin, pidotimod, levamisole, golotimod, forphenicinol, and derivatives thereof, and pharmacologically acceptable salts thereof. For example, the pharmacologically acceptable salt of levamisole includes levamisole hydrochloride.

Bestatin is represented by the formula:

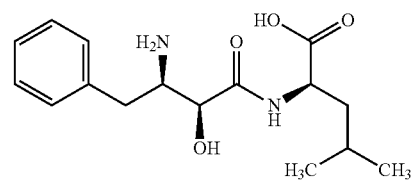 [SMILES: CC(C)C[C@@H](NC(=O)[C@@H](O)[C@H](N)Cc1ccccc1)C(=O)O]

Pidotimod is represented by the formula:

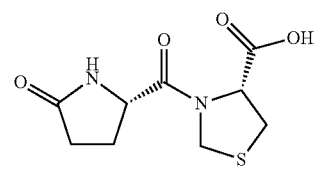 [SMILES: O=C1CC[C@@H](C(=O)N2CSC[C@H]2C(=O)O)N1]

Levamisole hydrochloride is represented by the formula:

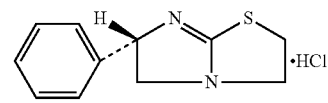

In the invention, the immunomodulatory small molecule drug is generally a compound having a molecular weight of less than 1000, preferably less than 500. In a preferred aspect of the invention, the immunomodulatory small molecule drug is at least one compound selected from the group consisting of bestatin, pidotimod, and levamisole hydrochloride.

The inventors have found that that when a desired antigen is administered, a Th2 cell differentiation inhibitor having a inhibitory action on a Th2 cell, such as a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenergic receptor antagonist, an adrenergic receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor is suitable for enhancing cellular immunity induction. Therefore, in one aspect, the cellular immunity induction accelerator of the invention is selected from the above inhibitors. Further, in further aspect, the inventors have found that at least one first cellular immunity induction promoter selected from the group consisting of the above Th2 cytokine inhibitors, at least one second cellular immunity promoter selected from the group consisting of a TLR ligand, a cyclic dinucleotide, and an immunomodulatory small molecule drug, and/or a third cellular immunity induction promoter which is a helper peptide is suitable for further increasing cellular immunity induction. Various methods for measuring cellular immunity induction quantitatively have been developed, and any one or more methods, for example, ELISPOT method as described in Example may be used.

In a preferred aspect, the cellular immunity induction promoter included in the vaccine composition of the invention is at least one first cellular immunity induction promoter selected from the group consisting of the Th2 cell differentiation inhibitors. More preferably, the vaccine composition of the invention further comprises at least one second cellular immunity promoter selected from the group consisting of a TLR ligand, a cyclic dinucleotide, and an immunomodulatory small molecule drug, and/or a third cellular immunity induction promoter which is a helper peptide.

As used herein, non-invasively administration means an administration without applying a physicalirritation, and/or a chemicalirritation, preferably without applying a physical irritation (for example, a physical irritation by tape stripping, microneedle, peeling process, damage process, perforation process) to a skin or a mucous membrane aggressively.

As used herein, the term "mildly irritating condition" means a condition under which irritation to be given to the skin lower than the irritation generally given in order to improve the skin permeability of the antigen contained in conventional vaccines, or a condition under which irritation is not given to the skin at all. In general, physical and/or chemical stimulation is given to the skin before or simultaneously with the transdermal administration of a conventional vaccine composition so that the antigen can penetrate through the skin. In a preferable aspect of this invention, examples of the mildly irritating condition include a condition of low physical irritation and a condition of low chemical irritation. The condition of low physical irritation is, for example, a condition under which transepidermal water loss (TEWL) (g/h·m$^2$) in the model animal for skin irritation evaluation is 50 or less, preferably 45 or less, more preferably 40 or less, even more preferably 35 or less, further preferably 30 or less. Since the TEWL level in non-treated skin is about 2 (g/h·m$^2$), the TEWL level before the administration of the vaccine composition may be 2 (g/h·m$^2$) or more. The condition of low chemical irritation is, for example, a condition under which the thymic stromal lymphopoietin (TSLP) level (pg/mg protein) in the skin of the model animal for skin irritation evaluation is 10000 or less, preferably 9000 or less, more preferably 8000 or less, further preferably 7000 or less. Since the TSLP level is about 1 (pg/mg protein) in non-treated skin, the TSLP level at completion of the administration of the vaccine composition exceeds 1 (pg/mg protein), preferably exceeds 2 (pg/mg protein), more preferably exceeds 3 (pg/mg protein). The "thymic stromal lymphopoietin (TSLP)" is a cytokine which participates in differentiation and recruitment of Th2 cells, and can be utilized as an index of the degree of skin irritation in the present invention. Greater TSLP value means stronger skin irritation. Examples of means for attaining the condition of low physical irritation include not-conducting the conventional pre-treatment of the skin before the administration such as not conducting tape stripping or microneedle puncture before the administration. Examples of means for attaining the condition of low chemical irritation include avoiding administration of an irritating chemical ingredient such as ethanol or a surfactant at a certain amount or more. The procedure for attaining the mildly irritating condition can be determined by using a model animal for skin irritation evaluation, and the determined procedure can be applied to the subject to be treated by the vaccine composition, for example, a human subject.

As used herein, the term "cancer" means a cancer accompanying an abnormal expression, such as overexpression, of cancer genes, and includes a hematopoietic organ tumor or a solid cancer. The cancer gene includes, for example, a survivin gene, a GPC3 gene, an HER2/neu gene, an MAGE3 gene, an MAGE A1 gene, an MAGE A3/A6 gene, an MAGE A4 gene, an MAGE12 gene, proteinase-3 gene, an AFP gene, a CA-125 gene, a CD44 gene, a CEA gene, a c-Kit gene, a c-met gene, a c-myc gene, an L-myc gene, a COX2 gene, a CyclinD1 gene, a Cytokeratin-7 gene, a Cytokeratin-19 gene, a Cytokeratin-20 gene, an E2F1 gene, an E2F3 gene, an EGFR gene, a Gli1 gene, a hCGβ gene, an HIF-1α gene, an HnRNP A2/B1 gene, an hTERT gene, an MDM gene, an MDR-1 gene, an MMP-2 gene, an MMP-9 gene, an Muc-1 gene, an Muc-4 gene, an Muc-7 gene, an NSE gene, a ProGRP gene, a PSA gene, a RCAS1 gene, a SCC gene, a thymoglobulin gene, a VEGF-A gene, and a VEGF-A gene. The cancer accompanying the overexpression of the survivin gene includes malignant lymphoma, bladder carcinoma, lung cancer, and colorectal cancer, without limitation. The cancer accompanying the overexpression of the GPC3 gene includes liver cancer, bile duct cancer, and gastric cancer, without limitation. The cancer accompanying the overexpression of the HER2/neu gene includes breast cancer, gastric cancer, ovarian cancer, uterine cancer, bladder carcinoma, non small cell lung cancer, and prostate cancer, without limitation. The cancer accompanying the overexpression of the MAGE3 gene includes melanoma, lung cancer, head and neck cancer, bladder carcinoma, gastric cancer, esophagus cancer, and liver cancer, without limitation. The cancer accompanying the overexpression of the proteinase-3 gene includes acute myeloid leukaemia, and pancreas cancer, without limitation.

As used herein, the term "abnormal expression of a gene" means that the expression level of the gene in a cell is increased or decreased dramatically, for example, two times or more, for example, 4 times or more than that of the other cell in the same tissue. The term "overexpression" means that the abnormal expression is an increase of the expression level. The expression level of the gene can easily be measured by any well known method in the art.

As used herein, the term "subject" means any animal whose immune response can be induced in practical use by administering the vaccine composition, and typically includes mammals including human, such as mouse, rat, dog, cat, rabbit, horse, cow, sheep, pig, goat, monkey, and chimpanzee. The particularly preferred subject is human.

As used herein, the term "model animal for immunological evaluation" means a model animal for evaluating immunity induction properties of the vaccine composition, and specifically means a model animal for evaluating cellular immunity induction level. The model animal for immunological evaluation should be selected in view of compatibility between the antigen in the vaccine composition to be evaluated and the MHC class 1 molecule of the animal. For example, in the case of a vaccine composition containing a HLA-A*24 type MHC restricted class 1 peptide, the property may be evaluated in a BALB/c mouse. In the case of a vaccine composition containing a HLA-A*02 type MHC restricted peptide, the property may be evaluated in a genetically modified mouse by which cellular immunity induction by the HLA-A*02 type MHC restricted peptide can be evaluated. In the case of a vaccine composition containing other HLA type MHC restricted peptide, the property is evaluated in an animal by which cellular immunity induction by the HLA type MHC restricted peptide can be evaluated. In the case of a vaccine composition containing a protein antigen, the property is evaluated in an animal having MHC compatible with a class 1 epitope to be used to induce the cellular immunity, among various class 1 epitopes included in the amino acid sequence of the protein antigen. When the hair of the animal is cut to ensure the place for transdermal administration, the animal should be used after it is recovered from the skin damage caused by the hair cut.

As used herein, the term "model animals for evaluating skin irritation" means a model animal for evaluating transepidermal water loss (TEWL) as an index of physical irritation of the skin and TSLP n index of the skin irritation property of the vaccine composition. Regardless of the type of the antigens contained in the vaccine composition, a C57BL/6 mouse may be used as the model animals for evaluating skin irritation. Then the hair of the animal is cut to ensure the place for transdermal administration, the animal should be used after it is recovered from the skin damage caused by the hair cut.

As used herein, the term "cancer antigen" means a substance which is specifically expressed in tumor cells or cancer cells and can induce immune response, for example, protein, or peptide.

As used herein, the term "cancer antigen peptide" a partial peptide derived from a cancer antigen protein being capable of inducing cellular immunity. Generally, the cancer antigen peptide is generated when the cancer antigen protein, which is a product of a cancer gene, is decomposed in cancer cells, and presented on the surface of the cancer cells by a MHC class 1 molecule. The cancer antigen peptide to be used for the cancer vaccine formulation may be an endogenous cancer antigen peptide isolated or purified from the cancer cell, or a synthetic peptide having the same amino acid sequence as the endogenous cancer antigen peptide. In a preferred aspect of the invention, an endogenous cancer antigen peptide or a synthetic cancer antigen peptide, for example, selected from the group consisting of a survivin-2B peptide and/or a modified survivin-2B peptide, a GPC3 peptide and/or a modified GPC3 peptide, an HER2/neu_A24 peptide and/or a modified HER2/neu_A24 peptide, an MAGE3_A24 peptide and/or a modified MAGE3_A24 peptide, a PR1 peptide and/or a modified PR1 peptide, an HER2/neu_A02 peptide and/or a modified HER2/neu_A02 peptide, an HER2/neu E75 peptide and/or a modified HER2/neu E75 peptide, an MAGE3_A02 peptide and/or a modified MAGE3_A02 peptide, and an MUC1 peptide and/or a modified MUC1 peptide can be used for cellular immunity induction As used herein, the term "antigen derived from an infectious pathogen" means an infectious pathogen or the component or a substance derived from thereof, which can induce cellular immunity. Therefore, an infectious disease can be treated or prevented by administering an antigen derived from an infectious pathogen, and preferably with a cellular immunity induction promoter, to a subject. In a preferred aspect of the invention, a peptide, for example, selected from the group consisting of an IPEP87 peptide and/or a modified IPEP87 peptide and an HBVenv peptide and/or a modified HBVenv peptide can be used as the antigen derived from an infectious pathogen.

As used herein, the term "infectious disease" means a disease caused by infection, proliferation, and the like of an infectious pathogen, for example, a viral disease affected by the infection of an adenovirus (for example, a human adenovirus), a herpes virus (for example, a herpes simplex virus, a varicella-zoster virus, a cytomegalovirus, a human herpes virus or a Kaposi's sarcoma-associated herpes virus), a picornavirus (for example, a poliovirus, a cold virus or a hepatitis A virus), a poxvirus (for example, a smallpox virus, a vaccinia virus or a molluscum contagiosum virus), a picornavirus (for example, a rhinovirus or an enterovirus), an Orthomyxoviridae virus (for example, an influenza virus), a paramyxovirus (for example, a parainfluenza virus, a mumps virus, a measles virus, a respiratory syncytial virus (RSV) or an Newcastle disease virus), a parvovirus (for example, an adeno-associated virus), a togavirus (for example, a rubella virus), a coronavirus (for example, SARS coronavirus), a Hepadnaviridae virus (for example, a Hepatitis B virus), a flavivirus (for example, a Japanese encephalitis virus, an yellow fever virus, a dengue fever virus, a West Nile fever virus, a Saint Louis encephalitis virus, an Murray Valley virus, a hepatitis C virus and a hepatitis G virus), an hepevirus (for example, a hepatitis E virus), a papillomavirus (for example, a human papillomavirus), a calicivirus (for example, a norovirus), a rhabdovirus (for example, a rabies virus or a vesicular stomatitis virus), a Filoviridae virus (for example, an Ebola hemorrhagic fever virus), an arenavirus (for example, an Lassa virus virus or a hepatitis D virus), a Bunyaviridae virus (for example, a California encephalitis virus or a Rift Valley fever virus), a Reoviridae virus (for example, a rotavirus), a retrovirus (for example, a human immunodeficiency virus (HIV) or adult T-cell leukemia virus), or the like; a bacteriaa disease including a disease affected by the infection of a bacteria, for example, *Escherichia, Enterobacter, salmonella, staphylococcus, Shigella, Listeria, Aerobacter, Helicobacter, Klebsiella, Proteus, Pseudomonas, streptococcus, chlamydia, mycoplasma, pneumococcus, neisseria, Clostridium, Bacillus, Coryne-*

*bacterium, Mycobacterium, Campylobacter, Vibrio, Serratia, Providencia, Chromobacterium, Brucella, Yersinia, Hemophilus*, or *Bordetella*; a fungusa disease including *chlamydia*, candidiasis, aspergillosis, histoplasmosis, and cryptococcal meningitis, without limitation; or malaria, *pneumocystis carinii* pneumonia, leishmaniasis, cryptosporidiosis, toxoplasmosis, and trypanosomal infection, without limitation.

<Vaccine Composition for Transdermal Administration>

As used herein, the composition "for transdermal administration" may be provided in any formulation or preparation generally used for the transdermal administration, and for example, may be a liquid formulation for external use such as a liniment formulation or a lotion formulation, a spray formulation for external use such as aerosol agent, an ointment, a plaster, a cream formulation, a gel formulation, or an adhesive skin patch, such as a tape preparation, or a cataplasm preparation. The category, definition, properties or production method of these formulations and preparations is well known in the art, for example, see Japanese Pharmacopoeia Version 16.

For example, the base for the liniment formulation includes water, ethanol, fatty oils, for example, hard paraffin, soft paraffin, liquid paraffin, glycerin, paraffin oils, beeswax, metal soaps; mucosal fluids (mucilage); natural oils [for example, almond oil, corn oil, peanut oil, castor oil, olive oil or derivatives thereof (for example, polyoxy castor oil)]; mutton suets or derivatives thereof, fatty acids and/or esters thereof (for example, stearic acid, oleic acid, isopropyl myristate). The lotion formulation is a formation obtained by dispersing active ingredients finely and homogeneously in water-based liquid, including a dispersed lotion formulation, and a lyophilic lotion formulation. The suspending agent includes, for example, gum arabic, sodium alginate, sodium carboxymethyl cellulose, methylcellulose, and bentonite. The emulsifying agent includes, for example, sodium lauryl sulfate, and sorbitan fatty acid.

For example, as an ointment base, oils and fats, waxes, hydrocarbon compounds or the like as a hydrophobic base can be generally used. Specifically, the ointment base includes mineral bases, such as yellow vaseline, white vaseline, paraffin, liquid paraffin, Plastibase, and silicone, animal or plant bases, such as beeswax and animal fats. For example, the base for cream formulation includes water/oil type bases, such as hydrophilic ointment, and vanishing cream; oil/water type bases, such as hydrophilic vaseline, purified lanolin, aquahole, eucerin, neocerin, hydrous lanolin, cold cream, and hydrophilic Plastibase. For example, as a gel base, carboxy vinyl polymer as a hydrogel base, gel base, fat-free ointment, polyvinylpyrrolidone, polyvinyl alcohol, sodium polyacrylate, carboxymethyl cellulose, starch, xanthan gum, karaya gum, sodium alginate, methylcellulose, hydroxypropylcellulose, hydroxypropylmethylcellulose phthalate (HPMCP), cellulose acetate phthalate (CAP), carboxymethylethylcellulose (CMEC), ethylcellulose, hydroxyethyl cellulose, hydroxypropylmethyl cellulose, carboxy vinyl polymer, tragacanth, gum arabic, Tara-Gummi, tamarind seed gum, psyllium seed gum, gelatin, gellan gum, glucomannan, locust bean gum, guar gum, carrageenan, dextrin, dextran, amylose, potassium carboxymethyl cellulose, sodium carboxymethyl cellulose, calcium carboxymethyl cellulose, pullulan, chitosan, sodium carboxymethyl starch, *Plantago* seed coat, galactomannan, aminoalkyl methacrylate copolymer E, aminoalkyl methacrylate copolymer RS, methacrylic acid copolymer L, methacrylic acid copolymer LD, methacrylic acid copolymer S, methyl acrylate-methacrylic acid-methyl methacrylate copolymer, ethyl acrylate-methyl methacrylate copolymer, polyvinyl acetal diethyl amino acetate, casein, alkyl alginate ester, gelatin, polyethylene glycol can be used.

For example, the base for the cataplasm preparation includes gelatin, sodium carboxymethyl cellulose, methylcellulose, sodium polyacrylate, kaolin, polyvinyl alcohol, polyvinylpyrrolidone, glycerin, propylene glycol, and water. For example, the tape preparation further includes an adhesive layer comprising acrylic adhesives, natural rubber adhesives, synthetic rubber adhesives (including rubber elastomer, such as synthetic isoprene rubber, polyisobutylene (PIB), styrene-butadiene rubber, styrene-isoprene-styrene (SIS) rubber), silicone adhesives, vinylester adhesives, and vinyl ether adhesives, and a support which supports the adhesive layer. If desired, the adhesive layer may further contain a release liner which covers the adhesive layer to avoid exposure thereof before use and can easily be peeled from the adhesive layer upon use.

The amount of the antigen and the cellular immunity induction promoter in the pharmaceutical composition of the invention is not particularly limited. In one aspect, the vaccine composition of the invention contains a desired antigen, preferably in an amount of 0.01-40% by weight, more preferably 0.1-30% by weight based on the total weight of the composition. In one aspect, the vaccine composition of the invention comprises the cellular immunity induction promoter preferably in an amount of 0.001-30% by weight, more preferably 0.01-20% by weight, based on the total weight of the composition.

When the vaccine composition of the invention for transdermal administration is provided in the form of a tape preparation, the adhesive layer of the tape preparation (hereinafter referred to as "tape preparation of the invention") contains an antigen and, if desired, further contains a cellular immunity induction promoter. In one aspect, the adhesive layer of the tape preparation in the invention contains the antigen preferably in an amount of 0.01-40% by weight, more preferably 0.1-30% by weight based on a total amount of the adhesive layer. When the adhesive layer of the tape preparation of the invention contains a cellular immunity induction promoter, the cellular immunity induction promoter is contained preferably in an amount of 0.001-30% by weight, more preferably 0.01-20% by weight based on a total amount of the adhesive layer.

The adhesive which is to form the adhesive layer of the tape preparation of the invention is not particularly limited, and examples thereof include acrylic adhesives having an acrylic polymer; rubber adhesives having rubber elastomer, such as styrene-diene-styrene blockcopolymer (for example, styrene-isoprene-styrene blockcopolymer, styrene-butadiene-styrene blockcopolymer), polyisoprene, polyisobutylene, butyl rubber, and polybutadiene; silicone adhesives, such as silicone rubber, dimethyl siloxane base, diphenyl siloxane base; vinylether adhesives, such as polyvinylmethylether, polyvinylethylether, and polyvinylisobutylether; vinyl ester adhesives, such as vinyl acetate-ethylene copolymer; and polyester adhesives composed of a carboxylate component, such as dimethyl terephthalate, dimethyl isophthalate, dimethylphthalate and a polyhydric alcohol such as ethylene glycol. The particularly preferred adhesives are acrylic adhesives, rubber adhesives, or silicone adhesives. The adhesive is comprised in the adhesive layer preferably in an amount of 10-90% by weight, more preferably 20-80% by weight as the solid basis based on a total amount of the adhesive layer.

Examples of the acrylic adhesive include an acrylic acid ester adhesive containing, as a main component, a polymer comprising (meth)acrylic acid C2-C18 alkyl ester as a first monomer. Example of the (meth)acrylic acid alkyl ester (first monomer) includes a (meth)acrylic acid alkyl ester having a linear, branched, or cyclic alkyl group having a carbon number of 1 to 18 (for example, methyl, ethyl, propyl, butyl, pentyl, hexyl, cyclohexyl, heptyl, octyl, 2-ethylhexyl, nonyl, decyl, undecyl, dodecyl, tridecyl). A (meth)acrylic acid alkyl ester having a linear, branched, or cyclic alkyl group having a carbon number of 4 to 18 (for example, butyl, pentyl, hexyl, cyclohexyl, heptyl, octyl, 2-ethylhexyl, nonyl, decyl, undecyl, dodecyl, tridecyl) is preferred. Since the use of the monomer component which decreases the glass transition temperature of the polymer is more suitable for providing adhesive properties at ambient temperature, a (meth)acrylic acid alkyl ester having a linear, branched, or cyclic alkyl group having a carbon number of 4 to (for example, butyl, pentyl, hexyl, cyclohexyl, heptyl, octyl, 2-ethylhexyl, preferably, butyl, 2-ethylhexyl, cyclohexyl, particularly preferably 2-ethylhexyl) is more preferred. Specifically, butyl acrylate, 2-ethylhexyl acrylate, methacrylic acid 2-ethylhexyl, cyclohexyl acrylate, cyclohexyl methacrylate is more preferred. Among them, 2-ethylhexyl acrylate is most preferred. The alkyl (meth)acrylate ester (first monomer component) can be used alone, or as a combination of two or more.

Further, the acrylic adhesive may comprise a second monomer being capable of copolymerizing with the alkyl (meth)acrylate ester as described above. The second monomer includes a monomer having a functional group which can form a linking point when a cross-linker is used. The functional group being capable of participating with a crosslink reaction includes a hydroxyl group, a carboxyl group, a vinyl group. A hydroxyl group and a carboxyl group are preferred. Specific example of the monomer (second monomer component) includes hydroxyethyl (meth)acrylate ester, hydroxypropyl (meth)acrylate ester, N-hydroxyalkyl (meth)acrylamide, (meth)acrylic acid, itaconic acid, maleic acid, maleic acid anhydride, mesaconic acid, citraconic acid, glutaconic acid. Among them, in view of ease of availability, acrylic acid, methacrylic acid, hydroxyethyl acrylate ester (in particular, 2-hydroxyethyl acrylate) is preferred, and acrylic acid is most preferred. The monomer (second monomer component) can be used alone, or as a combination of two or more.

Further, the acrylic adhesive may comprise a third monomer in addition to the second monomer, if desired. The third monomer (third monomer component) includes, for example, vinyl esters, such as vinyl acetate, vinyl propionate; vinyl ethers, such as methylvinylether, ethylvinylether; vinylamides, such as N-vinyl-2-pyrolidone, N-vinyl-caprolactam; alkoxy (meth)acrylate ester, such as methoxymethyl (meth)acrylate ester, ethoxyethyl (meth)acrylate ester, tetrahydrofurfuryl (meth)acrylate ester; hydroxyl group containing groups, such as hydroxypropyl (meth)acrylate, α-hydroxy methyl acrylate (it is not a linking point as it is used for a third monomer component); (meth)acrylic acid derivatives having an amide group, such as (meth)acrylamide, dimethyl (meth)acrylamide, N-butyl (meth)acrylamide, N-methylol (meth)acrylamide; aminoalkyl ester (meth)acrylate, such as aminoethyl (meth)acrylate ester, dimethylaminoethyl (meth)acrylate ester, t-butylaminoethyl (meth)acrylate ester; alkoxyalkyleneglycol (meth)acrylate ester, such as methoxy ethylene glycol (meth)acrylate ester, methoxy diethylene glycol (meth)acrylate ester, ethoxy polyethylene glycol (meth)acrylate ester, methoxy polypropylene glycol (meth)acrylate ester; (meth)acrylonitrile; sulfonic acid containing monomers, such as styrene sulfonic acid, allylsulfonic acid, sulfopropyl (meth)acrylate, (meth)acryloyl oxynaphthalene sulfonic acid, acrylamide methylsulfonic acid; vinyl group containing monomers, such as vinylpiperidone, vinylpyrimidine, vinylpiperazine, vinylpyrrol, vinylimidazol, vinyloxazole, vinylmorpholine. Among them, vinyl esters and vinylamides are preferred. The vinyl esters are preferably vinyl acetate, and the vinylamides are preferably N-vinyl-2-pyrolidone. The monomer (third monomer component) can be used alone, or as a combination of two or more.

When the acrylic adhesive is a copolymer of an alkyl (meth)acrylate ester (first monomer component) and a vinyl monomer having a functional group which is capable of participating in a crosslink reaction (second monomer component), the alkyl (meth)acrylate ester and the vinyl monomer having a functional group which is capable of participating in a crosslink reaction are preferably blended in a proportion of the alkyl (meth)acrylate ester to the vinyl monomer having a functional group which is capable of participating in a crosslink reaction of 99-85: 1-15 by weight, more preferably 99-90: 1-10 by weight for copolymerization.

Further, when the acrylic adhesive is a copolymer of an alkyl (meth)acrylate ester (first monomer component), a vinyl monomer having a functional group which is capable of participating in a crosslink reaction (second monomer component) and another monomer other than the first and second monomer components (third monomer component), the alkyl (meth)acrylate ester, the vinyl monomer having a functional group which is capable of participating in a crosslink reaction, and another monomer other than the first and second monomer components are preferably blended in a proportion of the alkyl (meth)acrylate ester to the vinyl monomer having a functional group which is capable of participating with a crosslink reaction to another monomer other than the first and second monomer components of 40-94:1-15:5-50 by weight, more preferably 50-89:1-10:10-40 by weight.

The components may be polymerized by a known method. For example, the monomers in a solvent such as ethyl acetate may be reacted in the presence of a polymerization initiator (e.g. benzoyl peroxide, azobisisobutyronitrile etc.) at 50 to 70° C. for 5 to 48 hours.

The particularly preferred acrylic adhesive in the invention includes, for example, 2-ethylhexyl acrylate ester/acrylic acid/N-vinyl-2-pyrolidone copolymer, 2-ethylhexyl acrylate ester/N-(2-hydroxyethyl)acrylamide/N-vinyl-2-pyrolidone copolymer, a copolymer of 2-ethylhexyl acrylate ester/2-hydroxyethyl acrylate ester/vinyl acetate, 2-ethylhexyl acrylate ester/acrylic acid copolymer, more preferably, 2-ethylhexyl acrylate ester/acrylic acid/N-vinyl-2-pyrolidone copolymer.

If desired, the acrylic adhesive may be subjected to physical crosslinking treatment by radiation irradiation including ultraviolet irradiation or electron beam irradiation, or chemical crosslinking treatment using a variety of the cross-linker, for example, isocyanate compounds such as three functional isocyanates or organic peroxides, organic metal salts, metal alcholates, metal chelating compounds, polyfunctional compounds (polyfunctional external cross-linkers, or polyfunctional inner cross-linkers such as diacrylates or dimethacrylate).

Examples of the rubber adhesive include rubber adhesives in which rubber elastomers, for example, polyisobutylene-polybutene elastomer, styrene-diene-styrene blockcopolymer, styrene-butadiene elastomer, nitrile elastomer, chloroprene elastomer, vinylpyridine elastomer, polyisobutylene elastomer, butyl elastomer, or isoprene-isobutylene elastomer is blended. Among them, polyisobutylene (PIB), styrene-diene-styrene blockcopolymer [for example, styrene-butadiene-styrene blockcopolymer (SBS), styrene-isoprene-styrene blockcopolymer (SIS)] are preferably used in view of solubility of the peptides and the cellular immunity induction promoters and the skin adhesiveness. A mixture of two or more of those adhesives may also be used.

Further, the rubber adhesive may be a mixture of two or more rubber elastomer having a different average molecular weight in order to obtain a suitable adhesiveness and solubility of the rubber adhesive, and the rubber elastomers may be same component or different component. For example, with respect to polyisobutylene, a mixture of a high molecular weight polyisobutylene having an average molecular weight of 150,000-5,500,000 and a medium molecular weight polyisobutylene having an average molecular weight of 10,000-150,000 and/or a low molecular weight polyisobutylene having an average molecular weight of 500-4,000 is preferred. In this case, the high molecular weight polyisobutylene, the medium molecular weight polyisobutylene, and the low molecular weight polyisobutylene are suitably blended in a weight ratio of high molecular weight: medium molecular weight:low molecular weight=10-80, preferably 20-70:0-90, preferably 10-80:0-80, preferably 10-60.

As used herein, the average molecular weight means a viscosity average molecular weight calculated from Flory viscosity equation. The average molecular weight is calculated by calculating Staudinger index ($J_0$) by Schulz-Blaschke equation from a flow time resulted from a capillary 1 on an Ubbelohde type viscometer at 20° C., and then using the $J_0$ value in the following formula.
(Formula)

$$J_0 = \eta_{sp}/c(1+0.31\eta_{sp}) \text{(Schulz-Blaschke equation)}$$

$$\eta_{sp} = t/t_0 - 1$$

t: Flow time of solution (according to Hagenbach-couette correction formula)
$t_0$: Flow time of solvent (according to Hagenbach-couette correction formula)
c: Concentration of solution (g/cm³)

$$J_0 = 3.06 \times 10^{-2} \overline{Mv}^{0.65}$$

$\overline{Mv}$: Viscosity average molecular weight

The rubber adhesive may contain tackifiers, for example, rosin resins, polyterpene resins, coumarone-indene resins, petroleum based resins, terpene-phenol resins, xylene resins, and alicyclic saturated hydrocarbon resins in order to obtain a suitable adhesiveness. One, two or more tackifiers can be blended in a proportion of 50% by weight or less, preferably 5-40% by weight based on a total weight of the rubber adhesive.

Examples of the silicone adhesive include silicone adhesives selected from polyorganosiloxane adhesives, polydimethylsiloxane adhesives, and polydimethyl diphenyl-siloxane adhesives. Among them, a commercially available silicone adhesive, for example, BIO PSA from Dow Corning Corporation is preferably used.

Although the support which supports the adhesive layer is not particularly limited, preferred is a support that is substantially impervious to the peptide and the cellular immunity induction promoter so that the peptide, the cellular immunity induction promoter, additives or the like contained in the adhesive layer will not pass through the support and leaked from the rear surface.

As the support, for example, a single film of polyester, polyamide, polychlorovinylidene, polyethylene, polypropylene, polyvinylchloride, ethylene-ethyl acrylate copolymer, polytetrafluoroethylene, ionomer resin, metal foil, or their laminated film can be used. Among them, in order to make adhesiveness (anchorability) between the support and the adhesive layer good, it is preferable that the support is a laminate film of a nonporous plastic film and a porous film made of the aforementioned material. In this case, the adhesive layer is preferably formed at the side of the porous film. As the porous film, the film which improves the anchoring property to the adhesive layer is selected. Specifically, the film includes paper, woven fabric, non-woven fabric, knitted fabric, and a sheet treated mechanically by the perforation process. Among them, particularly preferred are paper, woven fabric, and non-woven fabric in view of handling property. The porous film having a thickness of 1-200 μm is selected in view of flexibility of the tape preparation and handling property of application. Further, when woven fabric or non-woven fabric is used as the porous film, the weight per unit area is preferably 5-30 g/m², more preferably 6-15 g/m².

Examples of most suitable supports include a laminate film of a polyester film (preferably, polyethylene terephthalate film) having a thickness of 1.5-6 μm and a non-woven fabric made of a polyester (preferably, polyethylene terephthalate) having a weight per unit area of 6-15 g/m².

In the tape preparation of the invention, a release liner is preferably laminated to the adhesive face of the adhesive layer in order to protect the adhesive face until use. The release liner is not particularly limited, as long as it is treated so that it has the releasing property and it can be released with a sufficiently small peeling force. For example, films of polyester, polyvinylchloride, polyvinylidene chloride, polyethylene terephthalate; papers such as high quality paper or glassine paper; or laminated films of a quality paper or glassine paper and polyolefin may be treated by coating a silicone resin, a fluorine resin or the like on the surface to be contacted with the adhesive layer and is used as the release liner. The release liner preferably has a thickness of 10-200 μm, more preferably 25-100 μm. Polyester layer, particularly, polyethylene terephthalate layer, is preferable in view of the barrier property and the cost. Further, in this case, the liner preferably has a thickness 25-100 μm in view of handling property.

Further, the pharmaceutical composition of the invention may optionally contain an additive. The additive may be selected from, for example, isotonizing agent, preservative and bactericidal agent, antioxidant, solubilizer, solubilization aid, suspending agent, filler, pH modifying agent, stabilizing agent, absorption promoter, sustained release preparation, coloring agent, plasticizer, cross-linker, adhesive, or a combination of these two or more additives depending on the major component of the base, the compatibility of the antigen and the cellular immunity induction promoter, administration regimen to be intended. Further, when the vaccine of the invention is a tape preparation, the tape preparation can contain a skin permeability enhancer as an additive.

As used herein, the term "skin permeability enhancer" means any substance which improves the efficiency of permeation of a transdermally administered antigen through the skin compared to the efficiency obtained without the substance. The skin permeability enhancer is not particularly limited, as long as the enhancer is liquid at room temperature (25° C.), that is, has fluidity at that temperature and has an absorption promoting effect. When the skin permeability enhancer is a mixture of two or more substances, the mixture is liquid at room temperature (25° C.) and has an absorption promoting effect. The skin permeability enhancer may be an organic liquid and preferably, a hydrophobic liquid in view of their compatibility with the adhesive layer. Examples of skin permeability enhancers include for example, higher alcohols, such as oleyl alcohol, octyldodecanol; polyhydric alcohol, such as glycerin, ethylene glycol, polypropylene glycol; higher fatty acids, such as oleic acid, caprylic acid; fatty acid esters, such as isopropyl myristate, isopropyl palminate, ethyl oleate; polybasic acid esters, such as diethyl sebacate, diisopropyl adipate; polyhydric alcohol fatty acid esters, such as triisostearic acid diglyceryl, monooleic acid sorbitan, dicaprylic acid propylene glycol, monolauric acid polyethylene glycol, tetraoleic acid polyoxyethylene sorbit; polyoxyethylenealkylethers, such as polyoxyethylenelaurylether; hydrocarbons, such as squalane, liquid paraffin; plant oils, such as olive oil, castor oil; silicone oil; pyrolidones, such as N-methylpyrolidone, N-dodecylpyrolidone; sulfoxides, such as decylmethylsulfoxide. They can be used alone, or as a combination of two or more.

When rubber adhesives or acrylic adhesives are used, a second skin permeability enhancer can be used. Specific s of the second skin permeability enhancer include polyvinylpyrrolidone, crospovidone, polypropylene glycol, polyvinyl alcohol, carboxy vinyl polymer, hydroxypropylcellulose, or mixture thereof, without limitation. In a preferred aspect, the second skin permeability enhancer of the invention is polyvinylpyrrolidone, crospovidone and/or polypropylene glycol.

In view of the improvement of skin permeability of the antigen peptide, the skin permeability enhancer which is preferably used includes higher alcohols, more specifically, higher alcohols having a carbon number of 8-18 (preferably 8-14), fatty acid esters, more specifically, fatty acid esters of a fatty acid having a carbon number of 8-18 (preferably 12-16) and a monovalent alcohol having a carbon number of 1-18, polyhydric alcohol fatty acid esters, in particular, fatty acid esters, in particular, isopropyl myristate, isopropyl palmitate, or diethyl sebacate. The amount of the skin permeability enhancer is preferably 0.1% by weight to 70% by weight, more preferably 1% by weight to 65% by weight, more preferably 5% by weight to 60% by weight based on a total amount of the adhesive layer. When the proportion of the skin permeability enhancer is 0.1% by weight or more, high transdermal proabsorptive effect is obtained. When the proportion is 70% by weight or less, high transdermal proabsorptive effect is advantageously obtained while preventing the decrease of total adhesiveness and cohesion force.

The composition of the invention is preferably administered to a subject under mildly irritating condition. The administration under mildly irritating condition is accomplished by, for example, (i) administering the composition of the invention to a subject in a condition in which transepidermal water loss (TEWL) (g/h·m$^2$) is 50 or less as evaluated by model animals for evaluating skin irritation, (ii) administering the composition of the invention to a subject under the condition in which cutaneous TSLP level (pg/mg protein) is 10000 or less as evaluated by model animals for evaluating skin irritation.

As used herein, "pharmacologically acceptable salt" which can be comprised in the composition of the invention means salts which has no harmful effect on a subject to which the composition is administered, and does not impair the pharmacological activity of the ingredients in the composition. The pharmacologically acceptable salt includes inorganic acid salts (for example, hydrochloride or phosphate), organic acid salts (for example, acetate or phthalate, TFA salt), metal salts (alkali metal salts (for example, sodium salts, or potassium salts), alkaline earth metal salts (for example, calcium salts, or magnesium salts), aluminum salts), amine salts (triethylamine salts, benzylamine salts, diethanol amine salts, t-butylamine salts, dicyclohexylamine salts, alginine salts, dimethyl ammonium salts, or ammonium salts), without limitation.

In the invention, physical irritation means any physical irritation which gives damage to corneum, including scratch and scraping. For example, operation of tape stripping which removes corneum with an adhesive tape or the like, operation of giving damage to the skin with a cutter, and operation using a microneedle such as perforation in corneum are also included in the physical irritation.

The transepidermal water loss means an amount of water (g) which is transpired from 1 m$^2$ of keratin per one hour. The transepidermal water loss can be easily measured in a short time on a machine for measuring the water loss, and is widely used as an index for evaluating the damage degree of the skin. In the invention, transepidermal water loss can be used as an index of the physical irritation level.

The TSLP (Thymic stromal lymphopoietin) is one of IL-7 like cytokines produced in keratinocytes of the skin or thymus glands, mucosal epithelial cells. The TSLP is known to be involved in the maturation of dendritic cells or the differentiation of T cells. In the invention, TSLP level can be used as an index of the chemical irritation level which is irritation derived from a drug.

<Vaccine Composition for Mucosal Administration>

The vaccine composition for mucosal administration of the invention provides high cellular immunity induction effect in mucosal administration of various antigens to a subject.

As used herein, the composition for "mucosal administration" may be, for example, any formulations generally used for mucosal administration, for example, sublingual, nasal, buccal, rectal or vaginal administration, and includes half-solid formulations, such as a gel formulation (a jerry formulation), a cream formulation, an ointment, a plaster, liquid formulation, solid formulations, such as powder, fine granules, granules, film formulation or tablet, orally-disintegrating tablet, spray formulations for mucous membrane, such as aerosol formulation, and an aspirator. The category, definition, properties, production method or the like of these formulations and preparations is well known in the art, for example, see Japanese Pharmacopoeia Version 16.

For example, as a solvent for liquid formulation, a suitable amount of water or a solvent such as ethanol, glycerin, and propylene glycol can be used. The ingredients of the composition can be dispersed or dissolved in the solvent to prepare the liquid formulation.

For example, as a base for the gel formulation (the jerry formulation), carboxy vinyl polymer as a hydrogel base, gel base, fat-free ointment, polyvinyl pyrrolidone, polyvinyl alcohol, sodium polyacrylate, carboxymethyl cellulose, starch, xanthan gum, karaya gum, sodium alginate, methylcellulose, hydroxypropylcellulose, hydroxypropylmethylcellulose phthalate (HPMCP), cellulose acetate phthalate (CAP), carboxymethylethylcellulose (CMEC), ethylcellulose, hydroxyethyl cellulose, hydroxypropylmethyl cellulose, carboxy vinyl polymer, tragacanth, gum arabic, Tara-Gummi, tamarind seed gum, psyllium seed gum, gelatin, gellan gum, glucomannan, locust bean gum, guar gum, carrageenan, dextrin, dextran, amylose, potassium carboxymethyl cellulose, sodium carboxymethyl cellulose, calcium carboxymethyl cellulose, pullulan, chitosan, sodium carboxymethyl starch, *Plantago* seed coat, galactomannan, Eudragit, casein, alkyl alginate ester, gelatin, polyethylene glycol can be used. The base can be dissolved in a solvent to prepare a gel formulation having a flowability or formability. As a solvent, water is preferred, but glycerin or propylene glycol can be used.

For example, the base for the cream formulation includes water/oil type bases, such as hydrophilic ointment, and vanishing cream; oil/water type bases, such as hydrophilic vaseline, purified lanolin, Aquahole, Eucerin, Neocerin, hydrous lanolin, cold cream, and hydrophilic Plastibase. The base may be added to oleaginous solvent or water and agitated with a homogenizer at high speed to prepare a cream formulation.

Examples of the base for the film formulation include polyvinylpyrrolidone, polyvinyl alcohol, sodium polyacrylate, carboxymethyl cellulose, starch, xanthan gum, karaya gum, sodium alginate, methylcellulose, carboxy vinyl polymer, agar, hydroxypropylcellulose, hydroxypropylmethylcellulose phthalate (HPMCP), cellulose acetate phthalate (CAP), carboxymethylethylcellulose (CMEC), ethylcellulose, hydroxyethylcellulose, hydroxypropylmethylcellulose, carboxy vinyl polymer, tragacanth, gum arabic, locust bean gum, guar gum, carrageenan, dextrin, dextran, amylose, potassium carboxymethyl cellulose, sodium carboxymethyl cellulose, calcium carboxymethyl cellulose, pullulan, chitosan, sodium carboxymethyl starch, *Plantago* seed coat, galactomannan, aminoalkyl methacrylate copolymer E, aminoalkyl methacrylate copolymer RS, methacrylic acid copolymer L, methacrylic acid copolymer LD, methacrylic acid copolymer S, methyl acrylate-methacrylic acid-methyl methacrylate copolymer, ethyl acrylate-methyl methacrylate copolymer, polyvinyl acetal diethyl amino acetate, casein, and alkyl alginate ester. The film formulation may be prepared by dissolving the base in polar organic solvent such as water or ethanol, coating a film by the mixture, and then drying the coated film. In one preferred aspect, the vaccine composition for mucosal administration of the invention is a film formulation.

For example, the powder, fine granules, granules, or tablet can be prepared by mixing diluents such as lactose, cornstarch, microcrystalline cellulose; binders such as hydroxypropylcellulose, gum Arabicas an additive, and further a suitable amount of solvents such as water or ethanol, and then shaping the mixture through the steps of granulation, drying, compression and the like. If needed, lubricants such as magnesium stearate, or coating agents such as hydroxypropylcellulose or sucrose may be added to the mixture.

Examples of the base for the orally-disintegrating tablet (freeze dry type) include polysaccharides such as gelatin or pullulan. As a forming aid, mannitol, trehalose, sorbitol, glycine, or the like may be used. The orally-disintegrating tablet (freeze dry type) can be prepared by dissolving the additive in water to form a solution, dispensing the solution, and freeze-drying the solution. In one preferred aspect, the vaccine composition for mucosal administration of the invention is an orally-disintegrating tablet.

For example, the aerosol formulation contains a liquid formulation, a gel formulation having high flowability, a cream formulation, and fine powders such as a powder as a content. The aerosol formulation allows efficient administration to a site of administration, for example, oral mucosa or nasal mucosa because the solid or liquid fine particles of the content are dispersed into gas with an atomizing device.

<Vaccine Composition for Intracutaneous, Subcutaneous, and Intramuscular Administration>

The vaccine composition of the invention for intracutaneous, subcutaneous, and intramuscular administration provides high cellular immunity induction effect when an antigen is administered to a subject by the intracutaneous, subcutaneous, and intramuscular administration.

As used herein, the composition "for intracutaneous, subcutaneous, and intramuscular administration" may include an injectable formulation having suitable flowability, for example, liquid formulation, suspension, or cream formulation. The category, definition, properties, production method or the like of these formulations is well known in the art, for example, see Japanese Pharmacopoeia Version 16.

For example, the liquid formulation may be prepared by using a solvent for a liquid formulation such as a suitable amount of water or physiological saline solution, ethanol, glycerin, propylene glycol or the like, and dispersing or dissolving ingredients in the solvent.

Examples of the base which may be used for the water soluble suspension include carboxy vinyl polymer as a hydrogel base, gel base, fat-free ointment, polyvinylpyrrolidone, polyvinyl alcohol, sodium polyacrylate, carboxymethyl cellulose, starch, xanthan gum, karaya gum, sodium alginate, methylcellulose, hydroxypropylcellulose, hydroxypropylmethylcellulose phthalate (HPMCP), cellulose acetate phthalate (CAP), carboxymethylethylcellulose (CMEC), ethylcellulose, hydroxyethylcellulose, hydroxypropylmethylcellulose, carboxy vinyl polymer, tragacanth, gum arabic, Tara-Gummi, tamarind seed gum, psyllium seed gum, agar, gellan gum, glucomannan, locust bean gum, guar gum, carrageenan, dextrin, dextran, amylose, carboxymethyl cellulosepotassium, sodium carboxymethyl cellulose, calcium carboxymethyl cellulose, pullulan, chitosan, sodium carboxymethyl starch, *Plantago* seed coat, galactomannan, Eudragit, casein, alkyl alginate ester, gelatin, and polyethylene glycol. The suspension having flowability may be prepared by dissolving the base in a solvent. The solvent is preferably physiological saline solution, but glycerin or propylene glycol may be used.

Examples of the base for the hydrophobic suspension include water/oil type base, such as hydrophilic ointment, and vanishing cream; oil/water type base, such as hydrophilic vaseline, purified lanolin, aquahole, eucerin, neocerin, hydrous lanolin, cold cream, and hydrophilic Plastibase. The base may be added to oleaginous solvent or water and agitated with a homogenizer at high speed to prepare an oleaginous suspension.

The proportion of the antigen and the cellular immunity induction promoter in the composition of the invention is not particularly limited. In one aspect, the composition of the invention contains desired antigen, preferably in an amount of 0.001-40% by weight, more preferably 0.01-30% by weight based on the total weight of the composition. In one aspect, the pharmaceutical composition of the invention contains the cellular immunity induction promoter, preferably in an amount of 0.001-30% by weight, more preferably 0.01-20% by weight based on the total weight of the composition.

Further, the composition of the invention may optionally contain an additive. The additive can be selected from, for example, isotonizing agent, preservative and bactericidal agent, antioxidant, solubilizer, solubilization aid, suspending agent, filler, pH modifying agent, stabilizing agent, absorption promoter, sustained release preparation, coloring agent, plasticizer, adhesive, or a combination of these two or more additives, depending on the major component of the base, the compatibility of the antigen and the cellular immunity induction promoter, administration regimen to be intended.

As used herein, "pharmacologically acceptable salt" which can be comprised in the composition of the invention means saltshich has no harmful effect on a subject to which the composition is administered, and does not impair the pharmacological activity of the ingredients in the composition. The pharmacologically acceptable salt includes inorganic acid salts (for example, hydrochloride or phosphate), organic acid salts (for example, acetate or phthalate, TFA salt), metal salts (alkali metal salts (for example, sodium salts, or potassium salts), alkaline earth metal salts (for example, calcium salts, or magnesium salts), aluminum salt, or the like), amine salts (triethylamine salts, benzylamine salts, diethanol amine salts, t-butylamine salts, dicyclohexylamine salts, alginine salts, dimethyl ammonium salts, or ammonium salts), without limitation.

The therapeutically effective amount of the antigen can vary widely depending on a severity of the disease, an age or relative health of the subject, and other known facts. In general, satisfactory result may be obtained at a one day dose of about 0.1 µg to 1 g/kg body weight. The cellular immunity induction promoter can be administered with the antigen at the same time or sequentially, and preferably, it is administered simultaneously with the antigen. The effective amount of the cellular immunity induction promoter can vary widely depending on the kind of cellular immunity induction promoter to be used, the presence of other cellular immunity induction promoter, and the like. In general, satisfactory result is obtained at a one day dose of about 0.01 µg to 1 g/kg body weight. The one day dose may be administered in a single dose or in several divided portions at several times such as two times or more, for example, two, three, four or five times. The composition may be applied continuously for a period of between 1 minute and 7 days per one administration. The administration interval is suitably selected from daily to yearly (for example, daily, once per two days, once per three days, weekly, once per two weeks, monthly, once per three months, once per six months, yearly) or longer, depending on a condition of the patient, a severity of the disease, whether it is for treatment or prevention, and the like. Generally, for treating the patient having a severe disease, an antigen is administered with a higher frequency in a higher dose. For preventing the patient without the disease, an antigen is administered with a lower frequency in a lower dose.

The invention will be described in more detail and more specifically in the following Examples, but is not limited to the scope of the Examples.

EXAMPLES

The following substances were used:
Imiquimod: manufactured by Tokyo Chemical Industry Co., Ltd., clofibrate manufactured by LKT Laboratories, fenofibrate: manufactured by Wako Pure Chemical Industries, Ltd., quercetin: manufactured by Cayman Chemical, berberine (berberine chloride n hydrates): manufactured by Wako Pure Chemical Industries, Ltd., noscapine: manufactured by Wako Pure Chemical Industries, Ltd., 3,3'-diindolylmethane manufactured by Wako Pure Chemical Industries, Ltd., xanthone: manufactured by Wako Pure Chemical Industries, Ltd., parthenolide: manufactured by Wako Pure Chemical Industries, Ltd., etodolac: manufactured by Wako Pure Chemical Industries, Ltd., loxoprofen (loxoprofen Na): manufactured by Yoshindo Inc., indomethacin: manufactured by Wako Pure Chemical Industries, Ltd., aspirin: manufactured by Sigma-Aldrich, diclofenac (diclofenac sodium): manufactured by Wako Pure Chemical Industries, Ltd., ketoprofen: manufactured by Wako Pure Chemical Industries, Ltd., celecoxib: manufactured by TOCRIS bioscience, valdecoxib: manufactured by TOCRIS bioscience, docosahexaenoic acid: manufactured by Cayman Chemical, 2',5'-dideoxyadenosine: BIOMOL International, SCH23390: manufactured by Wako Pure Chemical Industries, Ltd., ropinirole (ropinirole hydrochloride): manufactured by Ragactives, rotigotine manufactured by STARNASCENS, GW627368X: manufactured by Cayman Chemical, sulprostone: manufactured by Cayman Chemical, cloprostenol: manufactured by Wako Pure Chemical Industries, Ltd., BWA868C: manufactured by Cayman Chemical, RO1138452: manufactured by Cayman Chemical, leukotriene B4: manufactured by Cayman Chemical, montelukast (montelukast sodium): LG Life Sciences, zileuton: Toronto Research Chemicals, nicotinic acid: manufactured by Wako Pure Chemical Industries, Ltd., glycyrrhizic acid (glycyrrhizic acid dipotassium): manufactured by Wako Pure Chemical Industries, Ltd., pirfenidone: manufactured by TOCRIS bioscience, tranilast: manufactured by Wako Pure Chemical Industries, Ltd., famotidine: manufactured by Wako Pure Chemical Industries, Ltd., Impip (Impip dihydrobromate): manufactured by TOCRIS bioscience, proxyfan: manufactured by TOCRIS bioscience, azelastine (azelastine hydrochloride): LKT Labs, cimetidine: manufactured by Wako Pure Chemical Industries, Ltd., 4-methylhistamine: manufactured by TOCRIS bioscience, olanzapine: manufactured by Wako Pure Chemical Industries, Ltd., yohimbine (yohimbine hydrochloride): manufactured by Wako Pure Chemical Industries, Ltd., acetylcholine (acetylcholine chloride): manufactured by Wako Pure Chemical Industries, Ltd., metergoline (metergoline phenylmethyl ester): manufactured by TOCRIS bioscience, clozapine: manufactured by Wako Pure Chemical Industries, Ltd., sumatriptan: manufactured by MYUNG IN PHARM, zolmitriptan: manufactured by Cipla, tolvaptan: manufactured by Sigma-Aldrich, desmopressin: manufactured by Sigma-Aldrich, pilocarpine (pilocarpine hydrochloride): manufactured by Wako Pure Chemical Industries, Ltd., midodrine (midodrine hydrochloride): manufactured by Wako Pure Chemical Industries, Ltd., propranolol (propranolol hydrochloride): manufactured by Wako Pure Chemical Industries, Ltd., xylazine: manufactured by Wako Pure Chemical Industries, Ltd., novokinin: manufactured by Sigma-Aldrich, baclofen: manufactured by Tokyo Chemical Industry Co., Ltd., TRAP-6: manufactured by Bachem, adenosine diphosphate: manufactured by MP Biomedicals, somatostatin-14: manufactured by Bachem, GW405833: manufactured by Sigma-Aldrich, SEW2871: manufactured by Cayman Chemical, trimebutine (maleic acidtrimebutine): manufactured by Tokyo Chemical Industry Co., Ltd., loperamide (loperamide hydrochloride): manufactured by Wako Pure Chemical Industries, Ltd., melatonin: LKT Labs, biphenylindanone A: manufactured by Sigma-Aldrich, L-AP4 (L-2-amino-4-phosphonobutyric acid): manufactured by Wako Pure Chemical Industries, Ltd., diphenhydramine (diphenhydramine hydrochloride): manufactured by Wako Pure Chemical Industries, Ltd., tamsulosin (tamsulosin hydrochloride): manufactured by Cipla, resveratrol (resveratrol (synthetic)): manufactured by Wako Pure Chemical Industries, Ltd., and oxybutynin (oxybutynin hydrochloride): manufactured by Sigma-Aldrich. GPC3 peptide, Survivine-2B peptide, HER2/neu_A24 peptide, MAGE3_A24 peptide, IPEP87 peptide, HER2/neu E75 peptide, PR1 peptide, HER2/neu_A02 peptide, MAGE3_A02 peptide, HBVenv peptide, MUC1 peptide, OVA peptide (a peptide of 8 amino acids having a sequence Ser-Ile-Ile-Asn-Phe-Glu-Lys-Leu (SEQ ID NO: 16)), Peptide-25, Peptide-25B were prepared by chemical synthesis, and purified by HPLC before use. OVA protein: manufactured by Sigma-Aldrich was used.

Evaluation Method

The level of immunity induction by the administration of the preparations of the invention was evaluated by ELISPOT method, In vivo CTL assay, and cancer-bearing mouse test.

ELISPOT Method

Spleen cells ($3 \times 10^6$ cells/well) and an antigen peptide (100 µM) or an antigen protein (100 µg/mL) together with the culturing medium were placed into a well of an ELISPOT plate on which an anti-mouse IFN-γ antibody had been immobilized. The plate was cultured for 20 hours under the condition of 37° C. and 5% $CO_2$. The number of the spots representing IFN-γ-producing cells (spot number/$3 \times 10^6$ cells) was evaluated by the ELISPOT method.

In Vivo CTL Assay

Seven days after final immunization, the spleen cells (target cell or control cell) were transplanted according to the following procedure, and then, the spleen was isolated after 18 hours. The % Specific Lysis was obtained by performing the FACS measurement.

Procedure 1. Collection of Spleen Cells of Naïve Mouse

Naive mouse (C57BL/6) was used. Spleen was isolated from the naive mouse and mashed using a glass slide in a petri dish containing RPMI1640 medium. The mashed spleen was put into a 50 mL tube and centrifuged at 10° C. and 1100 rpm for 5 minutes. The supernatant was discarded. 20 mL of Lysis Buffer was added to the tube, followed by incubation at room temperature for 5 minutes. 20 mL of the medium was added to the tube and the tube was then centrifuged. The medium was added to the tube and the resultant was passed through a cell strainer to give spleen cell suspension.

Procedure 2. Labeling of the Spleen Cells with the Antigen

The spleen cells prepared in Procedure 1 were centrifuged at 10° C. and 1100 rpm for 5 minutes, the supernatant was discarded, and HBSS buffer was added to give cell suspension of $2 \times 10^7$ cells/mL. The cell suspension was dispensed into two 50 mL tubes, 100 µM of the antigen solution (the antigen was the same antigen used in the immunization test) was added to one of the tubes containing the cell solution so that the final concentration became 10 µM, to obtain a target cell. The cell in another tube was adopted as control. The cells in both tubes were incubated at 37° C. for 1 hour, centrifuged, the supernatant was discarded, and a medium was added.

Procedure 3. Labeling of the Spleen Cells with CFSE

The cell labelled with the antigen according to Procedure 2 was centrifuged, and 0.1% BSA-PBS was added to $1 \times 10^7$ cells/mL. To the target cell suspension was added 5 mM CFSE solution to give the final concentration of 10 µM, and to the control cell suspension was added 5 mM CFSE solution to give the final concentration of 1 µM, and the mixture was vortexed, followed by incubation at 37° C. for 10 minutes. Thereafter, centrifugation was performed, the supernatant was discarded, and the medium was added.

Procedure 4. Transplantation of Spleen Cell

The cell labelled with CFSE according to Procedure 3 was centrifuged, the supernatant was discarded, and HBSS buffer was added to the cells to give cell suspension of $5 \times 10^7$ cells/mL. Equal amounts of the target cell suspension and the control cell suspension were mixed, and 200 µL, aliquot of the mixture was introduced into each immunized mouse via orbital veins (transplanted cell number: $1 \times 10^7$ cells/animal).

Procedure 5. Preparation of Spleen Cell of the Immunized Mouse and Measurement of FACS Eighteen hours after the transplantation of the spleen cells, spleen of the mouse was isolated, and spleen cell suspension was prepared in the same manner as in Procedure 1. Thereafter, CFSE-positive cells were detected by FACS, and the ratio between CFSE high cells (target cells) and CFSE low cells (control cells) was obtained. The cytotoxic activity was calculated by the formula shown below. The obtained value can be used as an index showing the ability of the antigen specific killer cells induced by the immunization with the vaccine composition to attack specifically the cells that present the antigen in the living body. It was confirmed that the composition of the present invention can induce strong antigen-specific cellular immunity.

$$r = (\% \text{ CFSE low cells})/(\% \text{ CFSE high cells})$$

$$\% \text{ Specific Lysis} = (1-(r_{\text{non immunized}}/r_{\text{immunized}})) \times 100$$

Cancer-Bearing Mouse Test

C57BL/6 mice were inoculated with OVA-expressing E.G7 cancer cells (E.G7) (purchased from ATCC) through subcutaneous injection ($2 \times 10^6$ cells/mouse). After that, immunization was performed 5 times every 3 to 4 days, and a size of a tumor was evaluated at the 25th day from the inoculation of the cancer cells. The effect of the immunity induced was evaluated by the inhibition of the tumor growth, and it was confirmed that the administered formulation of the present invention had a high effect.

Preparation and results of evaluation for the respective formulations administered are shown below.

Preparation of Cream Formulation for Transdermal Administration

The cream formulations having the ingredients as shown in Tables 1-23 were prepared. Specifically, an antigen (a peptide or a protein), a Th2 cell differentiation inhibitor, a Th1 adjuvant, a helper peptide, and 15 parts by weight of dimethyl sulfoxide were mixed in an amount as shown in Tables 1-23 to form a mixture, and added a base (a base cream) to the total of 100 parts by weight, and then blended to form a cream formulation. The base cream was prepared by mixing and blending its components according to the composition as shown in Table 24.

A composite substrate in which a PET film/PET non-woven fabric laminate (area 0.7 $cm^2$) was stuck to the central portion of an adhesive tape for fixation so that the PET film side faces the tape was prepared. The cream formulation (4 mg) was coated on the non-woven fabric portion of this composite substrate, and this was used in the immunization test.

Mouse Immunization Test with Cream Formulation for Transdermal Administration

Mouse immunization test was performed with the cream formulations prepared as described above using a model animal for immunological evaluation. The immunity induction level was evaluated by ELISPOT method. Specifically, the hair of the back of the mouse was cut, and the mouse was kept until it recovered from the skin damage due to the hair cutting. After that, 4 mg of each cream formulation was applied to the skin of the back of the mouse for 24 hours, and then removed. After 6 days, the level of the cellular immunity induction specific for the antigen was evaluated. Six days after the administration, the spleen of the mouse was removed to prepare a suspension of spleen cells. Spleen cells ($3 \times 10^6$ cells/well) and an antigen peptide (100 μM) or an antigen protein (100 μg/mL) were added with a culture solution to a well of ELISPOT plate containing a fixed anti-mouse IFN-γ antigen, and co-cultured at 37° C. in 5% $CO_2$ for 20 hours. The number of the spot representing IFN-γ producing cells (spot number/$3 \times 10^6$ cells) was evaluated by ELISPOT method.

The effects of Th2 cell differentiation inhibitors were studied using a variety of cream formulations containing different antigens and helper peptides. The results of the immunization test and the mouse used in the test are shown in Tables 1-23. In the formulations shown as Examples, the level of immunity induction is enhanced by Th2 cell differentiation inhibitor. For each of the formulations in which the results of evaluation are shown, the level of immunity induction is enhanced by Th2 cell differentiation inhibitor. Further, the results in Table 2 are shown in FIG. 1. As shown in FIG. 1, a synergistic effect was obtained by a combination of a Th2 cell differentiation inhibitor and a Th1 adjuvant.

In Table 23, a difference in property was evaluated between a first cellular immunity induction promoter (cyclooxygenase inhibitor) and a second cellular immunity induction promoter (imiquimod or c-di-GMP). Cream formulations of Examples containing the first cellular immunity induction promoter (loxoprofen) exhibited characteristics different from those of cream formulations of Comparative examples containing the second cellular immunity induction promoter (imiquimod or c-di-GMP). That is, while the extent of induced immunity (results of ELISPOT and in vivo CTL assay) was not very strong, increase in tumor size was effectively inhibited.

TABLE 1

| No. | administration route | dosage form | antigen name | amount [%] | Th2 cell differentiation inhibitor name | amount [%] | helper peptide name | amount [%] | Mouse for immunological evaluation | Results of immunization (ELISPOT) |
|---|---|---|---|---|---|---|---|---|---|---|
| Comparative example 1 | transdermal | cream | OVAp | 5 | — | — | PEP | 1 | C57BL/6 | 121 |
| Comparative example 2 | transdermal | cream | OVAp | 5 | — | — | PADRE | 1 | C57BL/6 | 129 |
| Example 1 | transdermal | cream | OVAp | 5 | etodolac(COX inhibitor) | 3 | PEP | 1 | C57BL/6 | 404 |
| Example 2 | transdermal | cream | OVAp | 5 | loxoprofen(COX inhibitor) | 3 | PEP | 1 | C57BL/6 | 305 |
| Example 3 | transdermal | cream | OVAp | 5 | loxoprofen(COX inhibitor) | 3 | PADRE | 1 | C57BL/6 | 318 |
| Example 4 | transdermal | cream | OVAp | 5 | indomethacin(COX inhibitor) | 3 | PEP | 1 | C57BL/6 | 265 |
| Example 5 | transdermal | cream | OVAp | 5 | aspirin(COX inhibitor) | 3 | PEP | 1 | C57BL/6 | 275 |
| Example 6 | transdermal | cream | OVAp | 5 | diclofenac(COX inhibitor) | 3 | PEP | 1 | C57BL/6 | 295 |
| Example 7 | transdermal | cream | OVAp | 5 | ketoprofen(COX inhibitor) | 3 | PEP | 1 | C57BL/6 | 258 |
| Example 8 | transdermal | cream | OVAp | 5 | celecoxib(COX inhibitor) | 3 | PEP | 1 | C57BL/6 | 346 |
| Example 9 | transdermal | cream | OVAp | 5 | valdecoxib(COX inhibitor) | 3 | PEP | 1 | C57BL/6 | 327 |
| Example 10 | transdermal | cream | OVAp | 5 | GW627368X(prostaglandin receptor antagonist) | 3 | PEP | 1 | C57BL/6 | 304 |
| Example 11 | transdermal | cream | OVAp | 5 | RO1138452(prostaglandin receptor antagonist) | 3 | PEP | 1 | C57BL/6 | 284 |
| Example 12 | transdermal | cream | OVAp | 5 | BWA868C(prostaglandin receptor antagonist) | 3 | PEP | 1 | C57BL/6 | 275 |
| Example 13 | transdermal | cream | OVAp | 5 | sulprostone(prostaglandin receptor agonist) | 3 | PEP | 1 | C57BL/6 | 301 |
| Example 14 | transdermal | cream | OVAp | 5 | cloprostenol(prostaglandin receptor agonist) | 3 | PEP | 1 | C57BL/6 | 283 |
| Example 15 | transdermal | cream | OVAp | 5 | quercetin(TSLP production inhibitor) | 3 | PEP | 1 | C57BL/6 | 281 |
| Example 16 | transdermal | cream | OVAp | 5 | quercetin(TSLP production inhibitor) | 3 | PADRE | 1 | C57BL/6 | 301 |
| Example 17 | transdermal | cream | OVAp | 5 | berberine(TSLP production inhibitor) | 3 | PEP | 1 | C57BL/6 | 263 |
| Example 18 | transdermal | cream | OVAp | 5 | noscapine(TSLP production inhibitor) | 3 | PEP | 1 | C57BL/6 | 352 |
| Example 19 | transdermal | cream | OVAp | 5 | 3,3'-diindolylmethane(TSLP production inhibitor) | 3 | PEP | 1 | C57BL/6 | 322 |
| Example 20 | transdermal | cream | OVAp | 5 | xanthone(TSLP production inhibitor) | 3 | PEP | 1 | C57BL/6 | 385 |
| Example 21 | transdermal | cream | OVAp | 5 | parthenolide(TSLP production inhibitor) | 3 | PEP | 1 | C57BL/6 | 343 |
| Example 22 | transdermal | cream | OVAp | 5 | resveratrol(TSLP production inhibitor) | 3 | PEP | 1 | C57BL/6 | 305 |
| Example 23 | transdermal | cream | OVAp | 5 | nicotinic acid(niacin) (adenylate cyclase inhibitor) | 3 | PEP | 1 | C57BL/6 | 137 |
| Example 24 | transdermal | cream | OVAp | 5 | docosahexaenoic acid(omega-3 fatty acid) | 3 | PEP | 1 | C57BL/6 | 139 |
| Example 25 | transdermal | cream | OVAp | 5 | clofibrate(PPAR agonist) | 3 | PEP | 1 | C57BL/6 | 313 |
| Example 26 | transdermal | cream | OVAp | 5 | fenofibrate(PPAR agonist) | 3 | PEP | 1 | C57BL/6 | 262 |
| Example 27 | transdermal | cream | OVAp | 5 | SCH23390(dopamine receptor antagonist) | 3 | PEP | 1 | C57BL/6 | 137 |
| Example 28 | transdermal | cream | OVAp | 5 | ropinirole(dopamine receptor agonist) | 3 | PEP | 1 | C57BL/6 | 138 |
| Example 29 | transdermal | cream | OVAp | 5 | rotigotine(dopamine receptor agonist) | 3 | PEP | 1 | C57BL/6 | 143 |
| Example 30 | transdermal | cream | OVAp | 5 | Immepip(histamine receptor agonist) | 3 | PEP | 1 | C57BL/6 | 203 |

TABLE 1-continued

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Example 31 | transdermal | cream | OVAp | 5 | proxyfan(histamine receptor agonist) | 3 | PEP | 1 | C57BL/6 | 195 |
| Example 32 | transdermal | cream | OVAp | 5 | 4-methylhistamine(histamine receptor agonist) | 3 | PEP | 1 | C57BL/6 | 207 |
| Example 33 | transdermal | cream | OVAp | 5 | diphenhydramine(histamine receptor antagonist) | 3 | PEP | 1 | C57BL/6 | 283 |
| Example 34 | transdermal | cream | OVAp | 5 | azelastine(histamine receptor antagonist) | 3 | PEP | 1 | C57BL/6 | 310 |
| Example 35 | transdermal | cream | OVAp | 5 | cimetidine(histamine receptor antagonist) | 3 | PEP | 1 | C57BL/6 | 262 |
| Example 36 | transdermal | cream | OVAp | 5 | famotidine(histamine receptor antagonist) | 3 | PEP | 1 | C57BL/6 | 251 |
| Example 37 | transdermal | cream | OVAp | 5 | sumatriptan(serotonin receptor agonist) | 3 | PEP | 1 | C57BL/6 | 526 |
| Example 38 | transdermal | cream | OVAp | 5 | zolmitriptan(serotonin receptor agonist) | 3 | PEP | 1 | C57BL/6 | 295 |
| Example 39 | transdermal | cream | OVAp | 5 | metergoline(serotonin receptor antagonist) | 3 | PEP | 1 | C57BL/6 | 201 |
| Example 40 | transdermal | cream | OVAp | 5 | clozapine(serotonin receptor antagonist) | 3 | PEP | 1 | C57BL/6 | 228 |
| Example 41 | transdermal | cream | OVAp | 5 | olanzapine(serotonin receptor antagonist) | 3 | PEP | 1 | C57BL/6 | 218 |
| Example 42 | transdermal | cream | OVAp | 5 | yohimbine(serotonin receptor antagonist) | 3 | PEP | 1 | C57BL/6 | 221 |
| Example 43 | transdermal | cream | OVAp | 5 | tolvaptan(vasopressin receptor antagonist) | 3 | PEP | 1 | C57BL/6 | 143 |
| Example 44 | transdermal | cream | OVAp | 5 | desmopressin(vasopressin receptor agonist) | 3 | PEP | 1 | C57BL/6 | 177 |
| Example 45 | transdermal | cream | OVAp | 5 | oxybutynin(muscarine receptor antagonist) | 3 | PEP | 1 | C57BL/6 | 215 |
| Example 46 | transdermal | cream | OVAp | 5 | acetylcholine(muscarine receptor antagonist) | 3 | PEP | 1 | C57BL/6 | 218 |
| Example 47 | transdermal | cream | OVAp | 5 | trimebutine(muscarine receptor antagonist) | 3 | PEP | 1 | C57BL/6 | 203 |
| Example 48 | transdermal | cream | OVAp | 5 | pilocarpine(muscarine receptor agonist) | 3 | PEP | 1 | C57BL/6 | 139 |
| Example 49 | transdermal | cream | OVAp | 5 | tamsulosin(adrenalin receptor antagonist) | 3 | PEP | 1 | C57BL/6 | 215 |
| Example 50 | transdermal | cream | OVAp | 5 | propranolol(adrenalin receptor antagonist) | 3 | PEP | 1 | C57BL/6 | 218 |
| Example 51 | transdermal | cream | OVAp | 5 | xylazine(adrenalin receptor agonist) | 3 | PEP | 1 | C57BL/6 | 136 |
| Example 52 | transdermal | cream | OVAp | 5 | novokinin(angiotensin receptor agonist) | 3 | PEP | 1 | C57BL/6 | 134 |
| Example 53 | transdermal | cream | OVAp | 5 | baclofen(GABA receptor agonist) | 3 | PEP | 1 | C57BL/6 | 134 |
| Example 54 | transdermal | cream | OVAp | 5 | TRAP-6(thrombin receptor agonist) | 3 | PEP | 1 | C57BL/6 | 132 |
| Example 55 | transdermal | cream | OVAp | 5 | loperamide(opioid receptor agonist) | 3 | PEP | 1 | C57BL/6 | 304 |
| Example 56 | transdermal | cream | OVAp | 5 | adenosine diphosphate(ADP receptor agonist) | 3 | PEP | 1 | C57BL/6 | 137 |
| Example 57 | transdermal | cream | OVAp | 5 | montelukast(leukotriene receptor antagonist) | 3 | PEP | 1 | C57BL/6 | 143 |
| Example 58 | transdermal | cream | OVAp | 5 | zileuton(leukotriene receptor antagonist) | 3 | PEP | 1 | C57BL/6 | 138 |
| Example 59 | transdermal | cream | OVAp | 5 | leukotriene B4(leukotriene receptor agonist) | 3 | PEP | 1 | C57BL/6 | 138 |
| Example 60 | transdermal | cream | OVAp | 5 | melatonin(melatonin receptor agonist) | 3 | PEP | 1 | C57BL/6 | 308 |
| Example 61 | transdermal | cream | OVAp | 5 | somatostatin-14(somatostatin receptor agonist) | 3 | PEP | 1 | C57BL/6 | 143 |
| Example 62 | transdermal | cream | OVAp | 5 | GW405833(cannabinoid receptor agonist) | 3 | PEP | 1 | C57BL/6 | 148 |
| Example 63 | transdermal | cream | OVAp | 5 | SEW2871(sphingosine-1 phosphate receptor agonist) | 3 | PEP | 1 | C57BL/6 | 136 |
| Example 64 | transdermal | cream | OVAp | 5 | biphenylindanone A(metabotropic glutamate receptor agonist) | 3 | PEP | 1 | C57BL/6 | 220 |
| Example 65 | transdermal | cream | OVAp | 5 | L-AP4(metabotropic glutamate receptor agonist) | 3 | PEP | 1 | C57BL/6 | 213 |
| Example 66 | transdermal | cream | OVAp | 5 | glycyrrhizic acid(phospholipase A2 inhibitor) | 3 | PEP | 1 | C57BL/6 | 141 |

TABLE 1-continued

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Example 67 | transdermal | cream | OVAp | 5 | pirfenidone(TGF-beta production inhibitor) | 3 | PEP | 1 | C57BL/6 | 223 |
| Example 68 | transdermal | cream | OVAp | 5 | tranilast(TGF-beta production inhibitor) | 3 | PEP | 1 | C57BL/6 | 215 |
| Example 69 | transdermal | cream | OVAp | 5 | suplatast tosylate(Th2 cytokine inhibitor) | 3 | PEP | 1 | C57BL/6 | 143 |

OVAp: OVA peptide (SEQ ID NO: 16)
PEP: Peptide-25 (SEQ ID NO: 13) (helper peptide)
PADRE: PADRE(SEQ ID NO: 15) (helper peptide)

TABLE 2

| No. | administration route | dosage form | antigen name | antigen amount [%] | Th2 cell differentiation inhibitor name | Th2 cell differentiation inhibitor amount [%] | Th1 adjuvant name | Th1 adjuvant amount [%] | helper peptide name | helper peptide amount [%] | Mouse for immunological evaluation | Results of immunization (ELISPOT) |
|---|---|---|---|---|---|---|---|---|---|---|---|---|
| Comparative example 3 | transdermal | cream | OVAp | 2.5 | — | — | — | — | PEP | 0.3 | C57BL/6 | 57 |
| Comparative example 4 | transdermal | cream | OVAp | 2.5 | — | — | imiquimod | 3 | PEP | 0.3 | C57BL/6 | 200 |
| Example 70 | transdermal | cream | OVAp | 2.5 | loxoprofen (COX inhibitor) | 3 | — | — | PEP | 0.3 | C57BL/6 | 270 |
| Example 71 | transdermal | cream | OVAp | 2.5 | loxoprofen (COX inhibitor) | 1.5 | imiquimod | 1.5 | PEP | 0.3 | C57BL/6 | 481 |
| Example 72 | transdermal | cream | OVAp | 2.5 | loxoprofen | 3 | imiquimod | 3 | PEP | 0.3 | C57BL/6 | 570 |
| Example 73 | transdermal | cream | OVAp | 2.5 | berberine (TSLP production inhibitor) | 3 | — | — | PEP | 0.3 | C57BL/6 | 175 |
| Example 74 | transdermal | cream | OVAp | 2.5 | berberine | 3 | imiquimod | 3 | PEP | 0.3 | C57BL/6 | 545 |
| Example 75 | transdermal | cream | OVAp | 2.5 | berberine (TSLP production inhibitor) | 1.5 | imiquimod | 1.5 | PEP | 0.3 | C57BL/6 | 319 |

OVAp: OVA peptide (SEQ ID NO: 16)
PEP: Peptide-25 (SEQ ID NO: 13) (helper peptide)

TABLE 3

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Comparative example 5 | transdermal | cream | HER2/neu_A24 | 5 | — | — | PEPB | 0.3 | BALB/c | 138 |
| Comparative example 6 | transdermal | cream | HER2/neu_A24 | 5 | — | — | PADRE | 0.3 | BALB/c | 148 |
| Example 16 | transdermal | cream | HER2/neu_A24 | 5 | loxoprofen(COX inhibitor) | 3 | PEPB | 0.3 | BALB/c | 640 |
| Example 77 | transdermal | cream | HER2/neu_A24 | 5 | loxoprofen(COX inhibitor) | 3 | PADRE | 0.3 | BALB/c | 676 |
| Example 78 | transdermal | cream | HER2/neu_A24 | 5 | berberine(TSLP production inhibitor) | 3 | PEPB | 0.3 | BALB/c | 562 |
| Example 79 | transdermal | cream | HER2/neu_A24 | 5 | berberine(TSLP production inhibitor) | 3 | PADRE | 0.3 | BALB/c | 583 |

PEPB: Peptide-25B (SEQ ID NO: 14) (helper peptide)
PADRE: PADRE (SEQ ID NO: 15) (helper peptide)

TABLE 4

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Comparative example 7 | transdermal | cream | MAGE3_A24 | 5 | — | — | PEPB | 1 | BALB/c | 174 |
| Example 80 | transdermal | cream | MAGE3_A24 | 5 | loxoprofen (COX inhibitor) | 3 | PEPB | 1 | BALB/c | 338 |
| Example 81 | transdermal | cream | MAGE3_A24 | 5 | quercetin(TSLP production inhibitor) | 3 | PEPB | 1 | BALB/c | 280 |
| Example 82 | transdermal | cream | MAGE3_A24 | 5 | sumatriptan(serotonin receptor agonist) | 3 | PEPB | 1 | BALB/c | 445 |
| Example 83 | transdermal | cream | MAGE3_A24 | 5 | azelastine hydrochloride(histamine receptor antagonist) | 3 | PEPB | 1 | BALB/c | 481 |
| Example 84 | transdermal | cream | MAGE3_A24 | 5 | melatonin(melatonin receptor agonist) | 3 | PEPB | 1 | BALB/c | 456 |
| Comparative example 8 | transdermal (injured skin) | cream | MAGE3_A24 | 5 | — | 3 | PEPB | 1 | BALB/c | 35 |
| Example 85 | transdermal (injured skin) | cream | MAGE3_A24 | 5 | sumatriptan(serotonin receptor agonist) | 3 | PEPB | 1 | BALB/c | 147 | injured skin: administration to a skin treated by 10 times of tape stripping
PEPB: Peptide-25B (SEQ ID NO: 14)

TABLE 5

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Comparative example 9 | transdermal | cream | survivin 2B | 5 | — | — | PEPB | 1 | BALB/c | 356 |
| Example 86 | transdermal | cream | survivin 2B | 5 | loxoprofen(COX inhibitor) | 3 | PEPB | 1 | BALB/c | 439 |
| Example 87 | transdermal | cream | survivin 2B | 5 | quercetin(TSLP production inhibitor) | 3 | PEPB | 1 | BALB/c | 432 |
| Example 88 | transdermal | cream | survivin 2B | 5 | sumatriptan(serotonin receptor agonist) | 3 | PEPB | 1 | BALB/c | 549 |
| Example 89 | transdermal | cream | survivin 2B | 5 | azelastine hydrochloride(histamine receptor antagonist) | 3 | PEPB | 1 | BALB/c | 441 |
| Example 90 | transdermal | cream | survivin 2B | 5 | melatonin(melatonin receptor agonist) | 3 | PEPB | 1 | BALB/c | 562 |

PEPB: Peptide-25B (SEQ ID NO: 14)

TABLE 6

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Comparative example 10 | transdermal | cream | GPC3 | 5 | — | — | PEPB | 1 | BALB/c | 5 |
| Example 91 | transdermal | cream | GPC3 | 5 | loxoprofen(COX inhibitor) | 3 | PEPB | 1 | BALB/c | 30 |
| Example 92 | transdermal | cream | GPC3 | 5 | quercetin(TSLP production inhibitor) | 3 | PEPB | 1 | BALB/c | 35 |

PEPB: Peptide-25B (SEQ ID NO: 14)

TABLE 7

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Comparative example 11 | transdermal | cream | IPEP87 | 5 | — | — | PEP | 1 | genetically modified | 210 |
| Comparative example 12 | transdermal | cream | IPEP87 | 5 | — | — | PADRE | 1 | genetically modified | 232 |
| Example 93 | transdermal | cream | IPEP87 | 5 | loxoprofen(COX inhibitor) | 3 | PEP | 1 | genetically modified | 949 |
| Example 94 | transdermal | cream | IPEP87 | 5 | loxoprofen(COX inhibitor) | 3 | PADRE | 1 | genetically modified | 987 |
| Example 95 | transdermal | cream | IPEP87 | 5 | quercetin(TSLP production inhibitor) | 3 | PEP | 1 | genetically modified | 805 |
| Example 96 | transdermal | cream | IPEP87 | 5 | quercetin(TSLP production inhibitor) | 3 | PADRE | 1 | genetically modified | 823 |

PEP: Peptide-25 (SEQ ID NO: 13) (helper peptide)
PADRE: PADRE (SEQ ID NO: 15) (helper peptide)

TABLE 8

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Comparative example 13 | transdermal | cream | HER2/neu E75 | 10 | — | — | PEP | 1 | genetically modified | 20 |
| Comparative example 14 | transdermal | cream | HER2/neu E75 | 10 | — | — | PADRE | 1 | genetically modified | 28 |
| Example 97 | transdermal | cream | HER2/neu E75 | 10 | etodolac (COX inhibitor) | 3 | PEP | 1 | genetically modified | 98 |
| Example 98 | transdermal | cream | HER2/neu E75 | 10 | loxoprofen(COX inhibitor) | 3 | PEP | 1 | genetically modified | 114 |
| Example 99 | transdermal | cream | HER2/neu E75 | 10 | loxoprofen(COX inhibitor) | 3 | PADRE | 1 | genetically modified | 125 |
| Example 100 | transdermal | cream | HER2/neu E75 | 10 | indomethacin(COX inhibitor) | 3 | PEP | 1 | genetically modified | 123 |
| Example 101 | transdermal | cream | HER2/neu E75 | 10 | aspirin (COX inhibitor) | 3 | PEP | 1 | genetically modified | 131 |
| Example 102 | transdermal | cream | HER2/neu E75 | 10 | diclofenac(COX inhibitor) | 3 | PEP | 1 | genetically modified | 132 |
| Example 103 | transdermal | cream | HER2/neu E75 | 10 | ketoprofen(COX inhibitor) | 3 | PEP | 1 | genetically modified | 138 |
| Example 104 | transdermal | cream | HER2/neu E75 | 10 | celecoxib(COX inhibitor) | 3 | PEP | 1 | genetically modified | 121 |
| Example 105 | transdermal | cream | HER2/neu E75 | 10 | valdecoxib(COX inhibitor) | 3 | PEP | 1 | genetically modified | 115 |
| Example 106 | transdermal | cream | HER2/neu E75 | 10 | GW627368X (prostaglandin receptor antagonist) | 3 | PEP | 1 | genetically modified | 141 |
| Example 107 | transdermal | cream | HER2/neu E75 | 10 | RO1138452 (prostaglandin receptor antagonist) | 3 | PEP | 1 | genetically modified | 122 |
| Example 108 | transdermal | cream | HER2/neu E75 | 10 | BWA868C (prostaglandin receptor antagonist) | 3 | PEP | 1 | genetically modified | 134 |
| Example 109 | transdermal | cream | HER2/neu E75 | 10 | sulprostone(prostaglandin receptor agonist) | 3 | PEP | 1 | genetically modified | 118 |
| Example 110 | transdermal | cream | HER2/neu E75 | 10 | cloprostenol (prostaglandin receptor agonist) | 3 | PEP | 1 | genetically modified | 115 |
| Example 111 | transdermal | cream | HER2/neu E75 | 10 | quercetin(TSLP production inhibitor) | 3 | PEP | 1 | genetically modified | 108 |
| Example 112 | transdermal | cream | HER2/neu E75 | 10 | quercetin(TSLP production inhibitor) | 3 | PADRE | 1 | genetically modified | 121 |
| Example 113 | transdermal | cream | HER2/neu E75 | 10 | berberine(TSLP production inhibitor) | 3 | PEP | 1 | genetically modified | 112 |
| Example 114 | transdermal | cream | HER2/neu E75 | 10 | noscapine(TSLP production inhibitor) | 3 | PEP | 1 | genetically modified | 118 |
| Example 115 | transdermal | cream | HER2/neu E75 | 10 | 3,3'-diindolylmethane (TSLP production inhibitor) | 3 | PEP | 1 | genetically modified | 114 |

TABLE 8-continued

| No. | administration route | dosage form | antigen name | amount [%] | Th2 cell differentiation inhibitor name | amount [%] | helper peptide name | amount [%] | Mouse for immunological evaluation | Results of immunization (ELISPOT) |
|---|---|---|---|---|---|---|---|---|---|---|
| Example 116 | transdermal | cream | HER2/neu E75 | 10 | xanthone(TSLP production inhibitor) | 3 | PEP | 1 | genetically modified | 120 |
| Example 117 | transdermal | cream | HER2/neu E75 | 10 | parthenolide(TSLP production inhibitor) | 3 | PEP | 1 | genetically modified | |
| Example 118 | transdermal | cream | HER2/neu E75 | 10 | resveratrol(TSLP production inhibitor) | 3 | PEP | 1 | genetically modified | |
| Example 119 | transdermal | cream | HER2/neu E75 | 10 | 2',5'-dideoxyadenosine (adenylate cyclase inhibitor) | 3 | PEP | 1 | genetically modified | 54 |
| Example 120 | transdermal | cream | HER2/neu E75 | 10 | nicotinic acid (niacin) (adenylate cyclase inhibitor) | 3 | PEP | 1 | genetically modified | |
| Example 121 | transdermal | cream | HER2/neu E75 | 10 | docosahexaenoic acid(omega-3 fatty acid) | 3 | PEP | 1 | genetically modified | 43 |
| Example 122 | transdermal | cream | HER2/neu E75 | 10 | clofibrate(PPAR agonist) | 3 | PEP | 1 | genetically modified | 102 |
| Example 123 | transdermal | cream | HER2/neu E75 | 10 | fenofibrate(PPAR agonist) | 3 | PEP | 1 | genetically modified | 89 |
| Example 124 | transdermal | cream | HER2/neu E75 | 10 | SCH23390(dopamine receptor antagonist) | 3 | PEP | 1 | genetically modified | 61 |
| Example 125 | transdermal | cream | HER2/neu E75 | 10 | ropinirole(dopamine receptor agonist) | 3 | PEP | 1 | genetically modified | 54 |
| Example 126 | transdermal | cream | HER2/neu E75 | 10 | rotigotine(dopamine receptor agonist) | 3 | PEP | 1 | genetically modified | |
| Example 127 | transdermal | cream | HER2/neu E75 | 10 | Immepip(histamine receptor agonist) | 3 | PEP | 1 | genetically modified | |
| Example 128 | transdermal | cream | HER2/neu E75 | 10 | proxyfan(histamine receptor agonist) | 3 | PEP | 1 | genetically modified | 85 |
| Example 129 | transdermal | cream | HER2/neu E75 | 10 | 4-methylhistamine (histamine receptor agonist) | 3 | PEP | 1 | genetically modified | 83 |
| Example 130 | transdermal | cream | HER2/neu E75 | 10 | diphenhydramine (histamine receptor antagonist) | 3 | PEP | 1 | genetically modified | 112 |
| Example 131 | transdermal | cream | HER2/neu E75 | 10 | azelastine hydrochloride (histamine receptor antagonist) | 3 | PEP | 1 | genetically modified | 121 |
| Example 132 | transdermal | cream | HER2/neu E75 | 10 | cimetidine(histamine receptor antagonist) | 3 | PEP | 1 | genetically modified | 118 |
| Example 133 | transdermal | cream | HER2/neu E75 | 10 | famotidine(histamine receptor antagonist) | 3 | PEP | 1 | genetically modified | 131 |
| Example 134 | transdermal | cream | HER2/neu E75 | 10 | sumatriptan(serotonin receptor agonist) | 3 | PEP | 1 | genetically modified | 109 |
| Example 135 | transdermal | cream | HER2/neu E75 | 10 | zolmitriptan(serotonin receptor agonist) | 3 | PEP | 1 | genetically modified | 119 |
| Example 136 | transdermal | cream | HER2/neu E75 | 10 | metergoline(serotonin receptor agonist) | 3 | PEP | 1 | genetically modified | 75 |
| Example 137 | transdermal | cream | HER2/neu E75 | 10 | clozapine(serotonin receptor antagonist) | 3 | PEP | 1 | genetically modified | |
| Example 138 | transdermal | cream | HER2/neu E75 | 10 | olanzapine(serotonin receptor antagonist) | 3 | PEP | 1 | genetically modified | 82 |
| Example 139 | transdermal | cream | HER2/neu E75 | 10 | yohimbine(serotonin receptor antagonist) | 3 | PEP | 1 | genetically modified | |
| Example 140 | transdermal | cream | HER2/neu E75 | 10 | tolvaptan(vasopressin receptor antagonist) | 3 | PEP | 1 | genetically modified | 61 |
| Example 141 | transdermal | cream | HER2/neu E75 | 10 | desmopressin (vasopressin receptor agonist) | 3 | PEP | 1 | genetically modified | 53 |
| Example 142 | transdermal | cream | HER2/neu E75 | 10 | oxybutynin (muscarine receptor antagonist) | 3 | PEP | 1 | genetically modified | |
| Example 143 | transdermal | cream | HER2/neu E75 | 10 | acetylcholine (muscarine receptor antagonist) | 3 | PEP | 1 | genetically modified | 78 |
| Example 144 | transdermal | cream | HER2/neu E75 | 10 | trimebutine (muscarine receptor antagonist) | 3 | PEP | 1 | genetically modified | 72 |
| Example 145 | transdermal | cream | HER2/neu E75 | 10 | pilocarpine(muscarine receptor agonist) | 3 | PEP | 1 | genetically modified | 49 |
| Example 146 | transdermal | cream | HER2/neu E75 | 10 | tamsulosin(adrenalin receptor antagonist) | 3 | PEP | 1 | genetically modified | |

TABLE 8-continued

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Example 147 | transdermal | cream | HER2/neu E75 | 10 | propranolol(adrenalin receptor antagonist) | 3 | PEP | 1 | genetically modified | 83 |
| Example 148 | transdermal | cream | HER2/neu E75 | 10 | xylazine(adrenalin receptor agonist) | 3 | PEP | 1 | genetically modified | 51 |
| Example 149 | transdermal | cream | HER2/neu E75 | 10 | novokinin(angiotensin receptor agonist) | 3 | PEP | 1 | genetically modified | 61 |
| Example 150 | transdermal | cream | HER2/neu E75 | 10 | baclofen(GABA receptor agonist) | 3 | PEP | 1 | genetically modified | 58 |
| Example 151 | transdermal | cream | HER2/neu E75 | 10 | TRAP-6(thrombin receptor agonist) | 3 | PEP | 1 | genetically modified | 65 |
| Example 152 | transdermal | cream | HER2/neu E75 | 10 | loperamide(opioid receptor agonist) | 3 | PEP | 1 | genetically modified | 121 |
| Example 153 | transdermal | cream | HER2/neu E75 | 10 | adenosine diphosphate(ADP receptor agonist) | 3 | PEP | 1 | genetically modified | 43 |
| Example 154 | transdermal | cream | HER2/neu E75 | 10 | montelukast (leukotriene receptor antagonist) | 3 | PEP | 1 | genetically modified | 52 |
| Example 155 | transdermal | cream | HER2/neu E75 | 10 | leukotriene B4(leukotriene receptor agonist) | 3 | PEP | 1 | genetically modified | 60 |
| Example 156 | transdermal | cream | HER2/neu E75 | 10 | melatonin(melatonin receptor agonist) | 3 | PEP | 1 | genetically modified | 113 |
| Example 157 | transdermal | cream | HER2/neu E75 | 10 | somatostatin-14 (somatostatin receptor agonist) | 3 | PEP | 1 | genetically modified | 58 |
| Example 158 | transdermal | cream | HER2/neu E75 | 10 | GW405833 (cannabinoid receptor agonist) | 3 | PEP | 1 | genetically modified | 63 |
| Example 159 | transdermal | cream | HER2/neu E75 | 10 | SEW2871(sphingosine-1 phosphate receptor agonist) | 3 | PEP | 1 | genetically modified | 48 |
| Example 160 | transdermal | cream | HER2/neu E75 | 10 | biphenylindanone A(metabotropic glutamate receptor agonist) | 3 | PEP | 1 | genetically modified | 80 |
| Example 161 | transdermal | cream | HER2/neu E75 | 10 | L-AP4(metabotropic glutamate receptor agonist) | 3 | PEP | 1 | genetically modified | 85 |
| Example 162 | transdermal | cream | HER2/neu E75 | 10 | dipotassium glycyrrhizinate(phospholipase A2 inhibitor) | 3 | PEP | 1 | genetically modified | 41 |
| Example 163 | transdermal | cream | HER2/neu E75 | 10 | pirfenidone(TGF-beta production inhibitor) | 3 | PEP | 1 | genetically modified | 72 |
| Example 164 | transdermal | cream | HER2/neu E75 | 10 | tranilast(TGF-beta production inhibitor) | 3 | PEP | 1 | genetically modified | 82 |
| Example 165 | transdermal | cream | HER2/neu E75 | 10 | suplatast tosylate(Th2 cytokine inhibitor) | 3 | PEP | 1 | genetically modified | 51 |

PEP: Peptide-25 (SEQ ID NO: 13)(helper peptide)
PADRE: PADRE (SEQ ID NO: 15)(helper peptide)

TABLE 9

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Comparative example 15 | transdermal | cream | PR1 | 5 | — | — | PEP | 1 | genetically modified | 3 |
| Example 166 | transdermal | cream | PR1 | 5 | loxoprofen(COX inhibitor) | 3 | PEP | 1 | genetically modified | 38 |
| Example 167 | transdermal | cream | PR1 | 5 | quercetin(TSLP production inhibitor) | 3 | PEP | 1 | genetically modified | 35 |

PEP: Peptide-25 (SEQ ID NO: 13)(helper peptide)

TABLE 10

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Comparative example 16 | transdermal | cream | MUC1 | 10 | — | — | PEP | 1 | genetically modified | 0 |
| Example 168 | transdermal | cream | MUC1 | 10 | loxoprofen(COX inhibitor) | 3 | PEP | 1 | genetically modified | 10 |
| Example 169 | transdermal | cream | MUC1 | 10 | quercetin(TSLP production inhibitor) | 3 | PEP | 1 | genetically modified | 12 |

PEP: Peptide-25 (SEQ ID NO: 13)(helper peptide)

TABLE 11

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Comparative example 17 | transdermal | cream | HER2/neu_A02 | 5 | — | — | PEP | 1 | genetically modified | 55 |
| Comparative example 18 | transdermal | cream | HER2/neu_A02 | 5 | — | — | PADRE | 1 | genetically modified | 63 |
| Example 170 | transdermal | cream | HER2/neu_A02 | 5 | loxoprofen(COX inhibitor) | 3 | PEP | 1 | genetically modified | 297 |
| Example 171 | transdermal | cream | HER2/neu_A02 | 5 | loxoprofen(COX inhibitor) | 3 | PADRE | 1 | genetically modified | 308 |
| Example 172 | transdermal | cream | HER2/neu_A02 | 5 | quercetin(TSLP production inhibitor) | 3 | PEP | 1 | genetically modified | 320 |
| Example 173 | transdermal | cream | HER2/neu_A02 | 5 | quercetin(TSLP production inhibitor) | 3 | PADRE | 1 | genetically modified | 342 |

PEP: Peptide-25 (SEQ ID NO: 13)(helper peptide)
PADRE: PADRE (SEQ ID NO: 15)(helper peptide)

TABLE 12

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Comparative example 19 | transdermal | cream | MAGE3_A02 | 10 | — | — | PEP | 1 | genetically modified | 33 |
| Comparative example 20 | transdermal | cream | MAGE3_A02 | 10 | — | — | PADRE | 1 | genetically modified | 38 |
| Example 174 | transdermal | cream | MAGE3_A02 | 10 | loxoprofen(COX inhibitor) | 3 | PEP | 1 | genetically modified | 196 |
| Example 175 | transdermal | cream | MAGE3_A02 | 10 | loxoprofen(COX inhibitor) | 3 | PADRE | 1 | genetically modified | 221 |
| Example 176 | transdermal | cream | MAGE3_A02 | 10 | quercetin(TSLP production inhibitor) | 3 | PEP | 1 | genetically modified | 230 |
| Example 177 | transdermal | cream | MAGE3_A02 | 10 | quercetin(TSLP production inhibitor) | 3 | PADRE | 1 | genetically modified | 245 |

PEP: Peptide-25 (SEQ ID NO: 13) (helper peptide)
PADRE: PADRE (SEQ ID NO: 15) (helper peptide)

TABLE 13

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Comparative example 21 | transdermal | cream | HBVenv | 10 | — | — | PEP | 1 | genetically modified | 4 |
| Comparative example 22 | transdermal | cream | HBVenv | 10 | — | — | PADRE | 1 | genetically modified | 5 |

TABLE 13-continued

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Example 178 | transdermal | cream | HBVenv | 10 | loxoprofen(COX inhibitor) | 3 | PEP | 1 | genetically modified | 74 |
| Example 179 | transdermal | cream | HBVenv | 10 | loxoprofen(COX inhibitor) | 3 | PADRE | 1 | genetically modified | 79 |
| Example 180 | transdermal | cream | HBVenv | 10 | quercetin(TSLP production inhibitor) | 3 | PEP | 1 | genetically modified | 85 |
| Example 181 | transdermal | cream | HBVenv | 10 | quercetin(TSLP production inhibitor) | 3 | PADRE | 1 | genetically modified | 90 |

PEP: Peptide-25 (SEQ ID NO: 13)(helper peptide)
PADRE: PADRE (SEQ ID NO: 15)(helper peptide)

TABLE 14

| No. | administration route | dosage form | antigen name | antigen amount [%] | Th2 cell differentiation inhibitor name | Th2 cell differentiation inhibitor amount [%] | Mouse for immunological evaluation | Results of immunization (ELISPOT) |
|---|---|---|---|---|---|---|---|---|
| Comparative example 23 | transdermal | cream | OVAp | 5 | — | — | C57BL/6 | 63 |
| Example 182 | transdermal | cream | OVAp | 5 | etodolac(COX inhibitor) | 3 | C57BL/6 | 323 |
| Example 183 | transdermal | cream | OVAp | 5 | loxoprofen(COX inhibitor) | 3 | C57BL/6 | 225 |
| Example 184 | transdermal | cream | OVAp | 5 | indomethacin(COX inhibitor) | 3 | C57BL/6 | |
| Example 185 | transdermal | cream | OVAp | 5 | aspirin(COX inhibitor) | 3 | C57BL/6 | |
| Example 186 | transdermal | cream | OVAp | 5 | diclofenac(COX inhibitor) | 3 | C57BL/6 | 210 |
| Example 187 | transdermal | cream | OVAp | 5 | ketoprofen(COX inhibitor) | 3 | C57BL/6 | |
| Example 188 | transdermal | cream | OVAp | 5 | celecoxib(COX inhibitor) | 3 | C57BL/6 | |
| Example 189 | transdermal | cream | OVAp | 5 | valdecoxib(COX inhibitor) | 3 | C57BL/6 | |
| Example 190 | transdermal | cream | OVAp | 5 | GW627368X(prostaglandin receptor antagonist) | 3 | C57BL/6 | 234 |
| Example 191 | transdermal | cream | OVAp | 5 | RO1138452(prostaglandin receptor antagonist) | 3 | C57BL/6 | 212 |
| Example 192 | transdermal | cream | OVAp | 5 | BWA868C(prostaglandin receptor antagonist) | 3 | C57BL/6 | 203 |
| Example 193 | transdermal | cream | OVAp | 5 | sulprostone(prostaglandin receptor agonist) | 3 | C57BL/6 | 225 |
| Example 194 | transdermal | cream | OVAp | 5 | cloprostenol(prostaglandin receptor agonist) | 3 | C57BL/6 | 203 |
| Example 195 | transdermal | cream | OVAp | 5 | quercetin(TSLP production inhibitor) | 3 | C57BL/6 | 201 |
| Example 196 | transdermal | cream | OVAp | 5 | berberine(TSLP production inhibitor) | 3 | C57BL/6 | |
| Example 197 | transdermal | cream | OVAp | 5 | noscapine(TSLP production inhibitor) | 3 | C57BL/6 | 275 |
| Example 198 | transdermal | cream | OVAp | 5 | 3,3'-diindolylmethane (TSLP production inhibitor) | 3 | C57BL/6 | |
| Example 199 | transdermal | cream | OVAp | 5 | xanthone(TSLP production inhibitor) | 3 | C57BL/6 | 307 |
| Example 200 | transdermal | cream | OVAp | 5 | parthenolide(TSLP production inhibitor) | 3 | C57BL/6 | |
| Example 201 | transdermal | cream | OVAp | 5 | resveratrol(TSLP production inhibitor) | 3 | C57BL/6 | |
| Example 202 | transdermal | cream | OVAp | 5 | clofibrate(PPAR agonist) | 3 | C57BL/6 | 234 |
| Example 203 | transdermal | cream | OVAp | 5 | fenofibrate(PPAR agonist) | 3 | C57BL/6 | 203 |
| Example 204 | transdermal | cream | OVAp | 5 | Immepip(histamine receptor agonist) | 3 | C57BL/6 | 164 |
| Example 205 | transdermal | cream | OVAp | 5 | proxyfan(histamine receptor agonist) | 3 | C57BL/6 | 132 |
| Example 206 | transdermal | cream | OVAp | 5 | 4-methylhistamine(histamine receptor agonist) | 3 | C57BL/6 | 145 |
| Example 207 | transdermal | cream | OVAp | 5 | diphenhydramine(histamine receptor antagonist) | 3 | C57BL/6 | |
| Example 208 | transdermal | cream | OVAp | 5 | azelastine(histamine receptor antagonist) | 3 | C57BL/6 | 230 |
| Example 209 | transdermal | cream | OVAp | 5 | cimetidine(histamine receptor antagonist) | 3 | C57BL/6 | 204 |
| Example 210 | transdermal | cream | OVAp | 5 | famotidine(histamine receptor antagonist) | 3 | C57BL/6 | 202 |

TABLE 14-continued

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Example 211 | transdermal | cream | OVAp | 5 | sumatriptan(serotonin receptor agonist) | 3 | C57BL/6 | 390 |
| Example 212 | transdermal | cream | OVAp | 5 | zolmitriptan(serotonin receptor agonist) | 3 | C57BL/6 | 208 |
| Example 213 | transdermal | cream | OVAp | 5 | metergoline(serotonin receptor antagonist) | 3 | C57BL/6 | |
| Example 214 | transdermal | cream | OVAp | 5 | clozapine(serotonin receptor antagonist) | 3 | C57BL/6 | 163 |
| Example 215 | transdermal | cream | OVAp | 5 | olanzapine(serotonin receptor antagonist) | 3 | C57BL/6 | 153 |
| Example 216 | transdermal | cream | OVAp | 5 | yohimbine(serotonin receptor antagonist) | 3 | C57BL/6 | 156 |
| Example 217 | transdermal | cream | OVAp | 5 | oxybutynin(muscarine receptor antagonist) | 3 | C57BL/6 | 153 |
| Example 218 | transdermal | cream | OVAp | 5 | acetylcholine(muscarine receptor antagonist) | 3 | C57BL/6 | |
| Example 219 | transdermal | cream | OVAp | 5 | trimebutine(muscarine receptor antagonist) | 3 | C57BL/6 | 135 |
| Example 220 | transdermal | cream | OVAp | 5 | tamsulosin(adrenalin receptor antagonist) | 3 | C57BL/6 | 154 |
| Example 221 | transdermal | cream | OVAp | 5 | propranolol(adrenalin receptor antagonist) | 3 | C57BL/6 | 165 |
| Example 222 | transdermal | cream | OVAp | 5 | loperamide(opioid receptor agonist) | 3 | C57BL/6 | 250 |
| Example 223 | transdermal | cream | OVAp | 5 | melatonin(melatonin receptor agonist) | 3 | C57BL/6 | 215 |
| Example 224 | transdermal | cream | OVAp | 5 | biphenylindanone A (metabotropic glutamate receptor agonist) | 3 | C57BL/6 | 165 |
| Example 225 | transdermal | cream | OVAp | 5 | L-AP4(metabotropic glutamate receptor agonist) | 3 | C57BL/6 | 156 |
| Example 226 | transdermal | cream | OVAp | 5 | pirfenidone(TGF-beta production inhibitor) | 3 | C57BL/6 | 164 |
| Example 227 | transdermal | cream | OVAp | 5 | tranilast(TGF-beta production inhibitor) | 3 | C57BL/6 | 156 |

OVAp: OVA peptide(SEQ ID NO: 16)

TABLE 15

| No. | administration route | dosage form | antigen name | amount [%] | Th2 cell differentiation inhibitor name | amount [%] | Th1 adjuvant name | amount [%] | Mouse for immunological evaluation | Results of immunization (ELISPOT) |
|---|---|---|---|---|---|---|---|---|---|---|
| Comparative example 24 | transdermal | cream | OVAp | 2.5 | — | | — | — | C57BL/6 | 45 |
| Comparative example 25 | transdermal | cream | OVAp | 2.5 | — | | imiquimod | 3 | C57BL/6 | 147 |
| Example 228 | transdermal | cream | OVAp | 2.5 | loxoprofen(COX inhibitor) | 3 | — | — | C57BL/6 | 195 |
| Example 229 | transdermal | cream | OVAp | 2.5 | loxoprofen(COX inhibitor) | 1.5 | imiquimod | 1.5 | C57BL/6 | 215 |
| Example 230 | transdermal | cream | OVAp | 2.5 | berberine(TSLP production inhibitor) | 3 | — | — | C57BL/6 | 110 |
| Example 231 | transdermal | cream | OVAp | 2.5 | berberine(TSLP production inhibitor) | 1.5 | imiquimod | 1.5 | C57BL/6 | 193 |

OVAp: OVA peptide(SEQ ID NO: 16)

TABLE 16

| No. | administration route | dosage form | antigen name | antigen amount [%] | Th2 cell differentiation inhibitor name | Th2 cell differentiation inhibitor amount [%] | Mouse for immunological evaluation | Results of immunization (ELISPOT) |
|---|---|---|---|---|---|---|---|---|
| Comparative example 26 | transdermal | cream | HER2/neu_A24 | 5 | — | — | BALB/c | 65 |
| Example 232 | transdermal | cream | HER2/neu_A24 | 5 | loxoprofen(COX inhibitor) | 3 | BALB/c | 465 |
| Example 233 | transdermal | cream | HER2/neu_A24 | 5 | berberine(TSLP production inhibitor) | 3 | BALB/c | 401 |
| Example 234 | transdermal | cream | HER2/neu_A24 | 5 | quercetin(TSLP production inhibitor) | 3 | BALB/c | |
| Example 235 | transdermal | cream | HER2/neu_A24 | 5 | GW627368X(prostaglandin receptor antagonist) | 3 | BALB/c | |
| Example 236 | transdermal | cream | HER2/neu_A24 | 5 | sulprostone(prostaglandin receptor agonist) | 3 | BALB/c | |
| Example 237 | transdermal | cream | HER2/neu_A24 | 5 | clofibrate(PPAR agonist) | 3 | BALB/c | |
| Example 238 | transdermal | cream | HER2/neu_A24 | 5 | famotidine(histamine receptor antagonist) | 3 | BALB/c | |
| Example 239 | transdermal | cream | HER2/neu_A24 | 5 | sumatriptan(serotonin receptor agonist) | 3 | BALB/c | |
| Example 240 | transdermal | cream | HER2/neu_A24 | 5 | loperamide(opioid receptor agonist) | 3 | BALB/c | |
| Example 241 | transdermal | cream | HER2/neu_A24 | 5 | melatonin(melatonin receptor agonist) | 3 | BALB/c | |

TABLE 17

| No. | administration route | dosage form | antigen name | antigen amount [%] | Th2 cell differentiation inhibitor name | Th2 cell differentiation inhibitor amount [%] | Mouse for immunological evaluation | Results of immunization (ELISPOT) |
|---|---|---|---|---|---|---|---|---|
| Comparative example 21 | transdermal | cream | IPEP87 | 5 | — | — | genetically modified | 105 |
| Example 242 | transdermal | cream | IPEP87 | 5 | loxoprofen(COX inhibitor) | 3 | genetically modified | 712 |
| Example 243 | transdermal | cream | IPEP87 | 5 | guercetin(TSLP production inhibitor) | 3 | genetically modified | 652 |
| Example 244 | transdermal | cream | IPEP87 | 5 | GW627368X(prostaglandin receptor antagonist) | 3 | genetically modified | |
| Example 245 | transdermal | cream | IPEP87 | 5 | sulprostone(prostaglandin receptor agonist) | 3 | genetically modified | |
| Example 246 | transdermal | cream | IPEP87 | 5 | clofibrate(PPAR agonist) | 3 | genetically modified | |
| Example 247 | transdermal | cream | IPEP87 | 5 | famotidine(histamine receptor antagonist) | 3 | genetically modified | |
| Example 248 | transdermal | cream | IPEP87 | 5 | sumatriptan(serotonin receptor agonist) | 3 | genetically modified | |
| Example 249 | transdermal | cream | IPEP87 | 5 | loperamide(opioid receptor agonist) | 3 | genetically modified | |
| Example 250 | transdermal | cream | IPEP87 | 5 | melatonin(melatonin receptor agonist) | 3 | genetically modified | |

TABLE 18

| No. | administration route | dosage form | antigen name | antigen amount [%] | Th2 cell differentiation inhibitor name | Th2 cell differentiation inhibitor amount [%] | Mouse for immunological evaluation | Results of immunization (ELISPOT) |
|---|---|---|---|---|---|---|---|---|
| Comparative example 28 | transdermal | cream | HER2/neu E75 | 10 | — | — | genetically modified | 6 |
| Example 251 | transdermal | cream | HER2/neu E75 | 10 | loxoprofen(COX inhibitor) | 3 | genetically modified | 72 |
| Example 252 | transdermal | cream | HER2/neu E75 | 10 | quercetin(TSLP production inhibitor) | 3 | genetically modified | 75 |
| Example 253 | transdermal | cream | HER2/neu E75 | 10 | GW627368X(prostaglandin receptor antagonist) | 3 | genetically modified | |
| Example 254 | transdermal | cream | HER2/neu E75 | 10 | sulprostone(prostaglandin receptor agonist) | 3 | genetically modified | |

TABLE 18-continued

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Example 255 | transdermal | cream | HER2/neu E75 | 10 | clofibrate(PPAR agonist) | 3 | genetically modified | |
| Example 256 | transdermal | cream | HER2/neu E75 | 10 | famotidine(histamine receptor antagonist) | 3 | genetically modified | |
| Example 257 | transdermal | cream | HER2/neu E75 | 10 | sumatriptan(serotonin receptor agonist) | 3 | genetically modified | |
| Example 258 | transdermal | cream | HER2/neu E75 | 10 | loperamide(opioid receptor agonist) | 3 | genetically modified | |
| Example 259 | transdermal | cream | HER2/neu E75 | 10 | melatonin(melatonin receptor agonist) | 3 | genetically modified | |

TABLE 19

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 29 | transdermal | cream | HER2/neu_A02 | 5 | — | — | genetically modified | 21 |
| Example 260 | transdermal | cream | HER2/neu_A02 | 5 | loxoprofen(COX inhibitor) | 3 | genetically modified | 215 |
| Example 261 | transdermal | cream | HER2/neu_A02 | 5 | quercetin(TSLP production inhibitor) | 3 | genetically modified | 244 |
| Example 262 | transdermal | cream | HER2/neu_A02 | 5 | GW627368X(prostaglandin receptor antagonist) | 3 | genetically modified | |
| Example 263 | transdermal | cream | HER2/neu_A02 | 5 | sulprostone(prostaglandin receptor agonist) | 3 | genetically modified | |
| Example 264 | transdermal | cream | HER2/neu_A02 | 5 | clofibrate(PPAR agonist) | 3 | genetically modified | |
| Example 265 | transdermal | cream | HER2/neu_A02 | 5 | famotidine(histamine receptor antagonist) | 3 | genetically modified | |
| Example 266 | transdermal | cream | HER2/neu_A02 | 5 | sumatriptan(serotonin receptor agonist) | 3 | genetically modified | |
| Example 267 | transdermal | cream | HER2/neu_A02 | 5 | loperamide(opioid receptor agonist) | 3 | genetically modified | |
| Example 268 | transdermal | cream | HER2/neu_A02 | 5 | melatonin(melatonin receptor agonist) | 3 | genetically modified | |

TABLE 20

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 30 | transdermal | cream | MAGE3_A02 | 10 | — | — | genetically modified | 15 |
| Example 269 | transdermal | cream | MAGE3_A02 | 10 | loxoprofen(COX inhibitor) | 3 | genetically modified | 145 |
| Example 270 | transdermal | cream | MAGE3_A02 | 10 | quercetin(TSLP production inhibitor) | 3 | genetically modified | 176 |
| Example 271 | transdermal | cream | MAGE3_A02 | 10 | GW627368X(prostaglandin receptor antagonist) | 3 | genetically modified | |
| Example 272 | transdermal | cream | MAGE3_A02 | 10 | sulprostone(prostaglandin receptor agonist) | 3 | genetically modified | |
| Example 273 | transdermal | cream | MAGE3_A02 | 10 | clofibrate(PPAR agonist) | 3 | genetically modified | |
| Example 274 | transdermal | cream | MAGE3_A02 | 10 | famotidine(histamine receptor antagonist) | 3 | genetically modified | |
| Example 275 | transdermal | cream | MAGE3_A02 | 10 | sumatriptan(serotonin receptor agonist) | 3 | genetically modified | |
| Example 276 | transdermal | cream | MAGE3_A02 | 10 | loperamide(opioid receptor agonist) | 3 | genetically modified | |
| Example 277 | transdermal | cream | MAGE3_A02 | 10 | melatonin(melatonin receptor agonist) | 3 | genetically modified | |

TABLE 21

| No. | administration route | dosage form | antigen name | antigen amount [%] | Th2 cell differentiation inhibitor name | Th2 cell differentiation inhibitor amount [%] | Mouse for immunological evaluation | Results of immunization (ELISPOT) |
|---|---|---|---|---|---|---|---|---|
| Comparative example 31 | transdermal | cream | HBVenv | 10 | — | — | genetically modified | 0 |
| Example 278 | transdermal | cream | HBVenv | 10 | loxoprofen(COX inhibitor) | 3 | genetically modified | 54 |
| Example 279 | transdermal | cream | HBVenv | 10 | quercetin(TSLP production inhibitor) | 3 | genetically modified | 65 |
| Example 280 | transdermal | cream | HBVenv | 10 | GW627368X(prostaglandin receptor antagonist) | 3 | genetically modified | |
| Example 281 | transdermal | cream | HBVenv | 10 | sulprostone(prostaglandin receptor agonist) | 3 | genetically modified | |
| Example 282 | transdermal | cream | HBVenv | 10 | clofibrate(PPAR agonist) | 3 | genetically modified | |
| Example 283 | transdermal | cream | HBVenv | 10 | famotidine(histamine receptor antagonist) | 3 | genetically modified | |
| Example 284 | transdermal | cream | HBVenv | 10 | sumatriptan(serotonin receptor agonist) | 3 | genetically modified | |
| Example 285 | transdermal | cream | HBVenv | 10 | loperamide(opioid receptor agonist) | 3 | genetically modified | |
| Example 286 | transdermal | cream | HBVenv | 10 | melatonin(melatonin receptor agonist) | 3 | genetically modified | |

TABLE 22

| No. | administration route | dosage form | antigen name | antigen amount [%] | Th2 cell differentiation inhibitor name | Th2 cell differentiation inhibitor amount [%] | Mouse for immunological evaluation | Results of immunization (ELISPOT) |
|---|---|---|---|---|---|---|---|---|
| Comparative example 32 | transdermal | cream | OVA protein | 5 | — | — | C57BL/6 | 137 |
| Example 287 | transdermal | cream | OVA protein | 5 | loxoprofen(COX inhibitor) | 3 | C57BL/6 | 269 |
| Example 288 | transdermal | cream | OVA protein | 5 | quercetin(TSLP production inhibitor) | 3 | C57BL/6 | 259 |
| Example 289 | transdermal | cream | OVA protein | 5 | GW627368X(prostaglandin receptor antagonist) | 3 | C57BL/6 | |
| Example 290 | transdermal | cream | OVA protein | 5 | sulprostone(prostaglandin receptor agonist) | 3 | C57BL/6 | |
| Example 291 | transdermal | cream | OVA protein | 5 | clofibrate(PPAR agonist) | 3 | C57BL/6 | |
| Example 292 | transdermal | cream | OVA protein | 5 | famotidine(histamine receptor antagonist) | 3 | C57BL/6 | |
| Example 293 | transdermal | cream | OVA protein | 5 | sumatriptan(serotonin receptor agonist) | 3 | C57BL/6 | |
| Example 294 | transdermal | cream | OVA protein | 5 | loperamide(opioid receptor agonist) | 3 | C57BL/6 | |
| Example 295 | transdermal | cream | OVA protein | 5 | melatonin(melatonin receptor agonist) | 3 | C57BL/6 | |

TABLE 23

| No. | administration route | dosage form | antigen name | antigen amount [%] | Th2 cell differentiation inhibitor name | Th2 cell differentiation inhibitor amount [%] | Th1 adjuvant name | Th1 adjuvant amount [%] |
|---|---|---|---|---|---|---|---|---|
| Comparative example 33 | transdermal | cream | OVAp | 5 | — | — | — | — |
| Comparative example 34 | transdermal | cream | OVAp | 5 | — | — | imiquimod | 3 |
| Comparative example 35 | transdermal | cream | OVAp | 5 | — | — | c-di-GMP | 1 |
| Example 296 | | cream | OVAp | 5 | loxoprofen (COX inhibitor) | 3 | — | — |
| Comparative example 36 | intradermal injection | injection (Montanide ISA51VG/saline = 1/1) | OVAp | 0.4 | — | — | — | — |

TABLE 23-continued

| No. | helper peptide name | amount [%] | Mouse for immunological evaluation | Results of immunization (ELISPOT) | % Specific Lysis (In vivo CTL assay) | tumor cell size(mm³) (cancer-bearing mouse test) |
|---|---|---|---|---|---|---|
| Comparative example 33 | — | — | C57BL/6 | 18 | 8 | 8000 |
| Comparative example 34 | PADRE | 1 | C57BL/6 | 153 | 30 | 6500 |
| Comparative example 35 | PADRE | 1 | C57BL/6 | 1500 | 85 | 4200 |
| Example 296 | PADRE | 1 | C57BL/6 | 268 | 37 | 3800 |
| Comparative example 36 | — | — | C57BL/6 | 30 | | 8000 |

TABLE 24

| additive | added amount |
|---|---|
| white vaseline | 60.7 wt % |
| sorbitan monostearate | 0.7 wt % |
| isostearic acid | 12.0 wt % |
| benzyl alcohol | 2.4 wt % |
| cetanol | 2.4 wt % |
| stearyl alcohol | 3.5 wt % |
| polysorbate 60 | 3.5 wt % |
| concentrated glycerin | 2.4 wt % |
| purified water | 12.4 wt % |

White vaseline, sorbitan monostearate, isostearic acid, benzyl alcohol, stearyl alcohol, polysorbate 60, concentrated glycerin, and dimethyl sulfoxide (DMSO) were purchased from Wako Pure Chemical Industries, Ltd.

(Method for Measuring TSLP Level)

When the application of the sample was completed, the skin of the back of the mouse was removed, and the skin was ground using a homogenizer (Physcotron, Microtec Co., Ltd.) in an extraction solvent (PBS solution containing a protease inhibitor (Protease Inhibitor Cocktail for general use, SIGMA-ALDRICH) and 10 µM indomethacin (Wako Pure Chemical Industries, Ltd.)). The ground skin was centrifuged at 4° C., 9,000×g for 10 minutes, and then the supernatant was collected. The amount of TSLP in the supernatant was measured by ELISA (Mouse TSLP Quantikine ELISA Kit, R&D Systems). Further, the total protein amount in the supernatant was measured by BCA method (Pierce BOA protein Assay Kit, Thermo SCIENTIFIC). The amount of TSLP was divided by the total protein amount for standardization.

(Measurement of Transepidermal Water Loss)

A portable machine for measuring the water loss in closed chamber method (manufactured by AsahiBioMed. Co., Ltd., VAPO SCAN AS-VT100RS) was used. The machine was contacted with the skin of mice for 5-15 seconds for measurement. Transepidermal water loss (TEWL) (g/h·m²) was measured 10 minutes after applying the pre-treatment.

Preparation of Tape Preparation for Transdermal Administration

Adhesives (acrylic adhesives) for tape preparations were prepared as follows. At inert gas atmosphere, 75 parts by weight of 2-ethylhexyl acrylate, 22 parts by weight of N-vinyl-2-pyrolidone, 3 parts by weight of acrylic acid, and 0.2 parts by weight of azobisisobutyronitrile were subjected to solution polymerization in ethyl acetate at 60° C. to obtain an acrylic adhesive solution.

The tape preparations for transdermal administration having compositions as shown in Tables 25 and 26 were prepared by using the acrylic adhesives. Specifically, an antigen peptide or an antigen protein, a Th2 cell differentiation inhibitor, a Th1 adjuvant, a helper peptide, and 34 parts by weight of isopropylmyristic acid, the adhesive solution, and an organic solvent (for example, ethyl acetate, ethanol, or toluene) in an amount as shown in Tables 25 and 26 to form a mixture, and spreaded on a release liner so that the thickness of the layer after drying was about 80 µm. The mixture was then dried to remove any organic solvent, and attached to a support to form a tape preparation. The adhesive solution was blended so that total amount of each components and the adhesive was 100 parts by weight after drying. The tape preparation was cut into a piece having an area of 0.7 cm². The piece was used as a sample for the immunization test. The release liner was peeled just before the application of the tape preparation.

Polyethylene terephthalate (PET) film (thickness 25 µm) was used as the support. Polyethylene terephthalate (PET) sheet (thickness 75 µm) treated with silicone was used as the release liner.

Mouse Immunization Test 2 with Tape Preparation for Transdermal Administration (Tape Preparation)

The tape preparations prepared as described above were used in a mouse immunization test using a model animal for immunological evaluation. The immunity induction level was evaluated by ELISPOT method. Specifically, the hair of the back of the mouse was cut, and the mouse was kept until it recovered from the skin damage. After that, 0.7 cm² of the each tape preparation was applied to the skin of the back of the mouse for 24 hours, and then removed. After 6 days, the level of the cellular immunity induction specific for the antigen was evaluated. Six days after the administration, the spleen of the mouse was removed to prepare a suspension of spleen cells. Spleen cells (3×10⁶ cells/well) and an antigen peptide (100 µM) were added with a culture solution to a well of ELISPOT plate containing a fixed anti-mouse IFN-γ antigen, and co-cultured at 37° C. in 5% CO₂ for 20 hours. The number of the spot which representing IFN-γ producing cells (spot number/3×10⁶ cells) was evaluated by ELISPOT method. The results of the immunization test and the mouse used are shown in Tables 25 and 26. In Tables 25 and 26, "genetically modified mouse" is a genetically modified mouse which can be used to evaluate the cellular immunity inducing ability of a HLA-A*0201 type MHC restricted peptide. In the formulations shown as Examples, Th2 cell differentiation inhibitor enhances the level of immunity induction. In Examples for which the results of evaluation were shown, Th2 cell differentiation inhibitor enhanced the level of immunity induction.

In addition, a combination of Th2 cell differentiation inhibitor and Th1 adjuvant exerted a synergistic effect.

TABLE 25

| No. | administration route | dosage form | antigen name | antigen amount [%] | Th2 cell differentiation inhibitor name | Th2 cell differentiation inhibitor amount [%] | Th1 adjuvant name | Th1 adjuvant amount [%] | helper peptide name | helper peptide amount [%] | Mouse for immunological evaluation | Results of immunization (ELISPOT) |
|---|---|---|---|---|---|---|---|---|---|---|---|---|
| Comparative example 37 | trans-dermal | tape | HER2/neu E75 | 10 | — | | — | | PEP | 1 | genetically modified | 14 |
| Comparative example 38 | trans-dermal | tape | HER2/neu E75 | 10 | — | | — | | PADRE | 1 | genetically modified | 17 |
| Comparative example 39 | trans-dermal | tape | HER2/neu E75 | 10 | — | | imiquimod | 3 | PEP | 1 | genetically modified | 78 |
| Example 297 | trans-dermal | tape | HER2/neu E75 | 10 | etodolac (COX inhibitor) | 1 | — | | PEP | 1 | genetically modified | 87 |
| Example 298 | trans-dermal | tape | HER2/neu E75 | 10 | etodolac (COX inhibitor) | 1 | — | | PADRE | 1 | genetically modified | 95 |
| Example 299 | trans-dermal | tape | HER2/neu E75 | 10 | loxoprofen (COX inhibitor) | 3 | — | | PEP | 1 | genetically modified | 64 |
| Example 300 | trans-dermal | tape | HER2/neu E75 | 10 | loxoprofen (COX inhibitor) | 3 | — | | PADRE | 1 | genetically modified | 86 |
| Example 301 | trans-dermal | tape | HER2/neu E75 | 10 | loxoprofen (COX inhibitor) | 1.5 | imiquimod | 1.5 | PEP | 1 | genetically modified | 101 |
| Example 302 | trans-dermal | tape | HER2/neu E75 | 10 | quercetin (TSLP production inhibitor) | 3 | — | | PEP | 1 | genetically modified | 47 |
| Example 303 | trans-dermal | tape | HER2/neu E75 | 10 | quercetin (TSLP production inhibitor) | 3 | — | | PADRE | 1 | genetically modified | 49 |
| Example 304 | trans-dermal | tape | HER2/neu E75 | 10 | quercetin (TSLP production inhibitor) | 1.5 | imiquimod | 1.5 | PEP | 1 | genetically modified | 127 |

PEP: Peptide-25 (SEQ ID NO: 13) (helper peptide)
PADRE: PADRE (SEQ ID NO: 15) (helper peptide)

TABLE 26

| No. | administration route | dosage form | antigen name | antigen amount [%] | Th2 cell differentiation inhibitor name | Th2 cell differentiation inhibitor amount [%] | Th1 adjuvant name | Th1 adjuvant amount [%] | Mouse for immunological evaluation | Results of immunization (ELISPOT) |
|---|---|---|---|---|---|---|---|---|---|---|
| Comparative example 40 | transdermal | tape | HER2/neu E75 | 10 | — | | — | | genetically modified | 5 |
| Comparative example 41 | transdermal | tape | HER2/neu E75 | 10 | — | | imiquimod | 3 | genetically modified | 55 |
| Example 305 | transdermal | tape | HER2/neu E75 | 10 | etodolac(COX inhibitor) | 1 | — | | genetically modified | 29 |
| Example 306 | transdermal | tape | HER2/neu E75 | 10 | loxoprofen(COX inhibitor) | 3 | — | | genetically modified | 21 |
| Example 307 | transdermal | tape | HER2/neu E75 | 10 | loxoprofen(COX inhibitor) | 1.5 | imiquimod | 1.5 | genetically modified | 85 |
| Example 308 | transdermal | tape | HER2/neu E75 | 10 | quercetin(TSLP production inhibitor) | 3 | — | | genetically modified | 18 |
| Example 309 | transdermal | tape | HER2/neu E75 | 10 | quercetin(TSLP production inhibitor) | 1.5 | imiquimod | 1.5 | genetically modified | 112 |

Preparation of Injectable Formulation for Subcutaneous Administration

The injectable formulations for subcutaneous administration having the ingredients as shown in Tables 27 to 35 were prepared to obtain samples for an immunization test. Specifically, saline as the base was added to an antigen (a peptide or a protein), a Th2 cell differentiation inhibitor and a helper peptide in an amount as shown in Tables 27 to 35, Montanide ISA51VG (manufactured by SEPPIC) as a sustained release agent, and 10 parts by weight of an additive (dimethyl sulfoxide), to the total of 100 parts by weight, and then blended to prepare the injectable formulation.

Mouse Immunization Test with Injectable Formulations for Subcutaneous Administration The injectable formulations as prepared above were used in a mouse immunization test using a model animal for immunological evaluation. The immunity induction level was evaluated by ELISPOT method. Specifically, the hair of the back of a mouse was cut, and the mouse was kept until it recovered from the skin damage. After that, 200 μL of each injectable formulation was administered subcutaneously to the back of the mouse. After 6 days, the level of the cellular immunity induction specific for the antigen was evaluated. Six days after the administration, the spleen of the mouse was removed to prepare a suspension of spleen cells. Spleen cells ($3\times10^6$ cells/well) and an antigen peptide (100 μM) were added with a culture solution to a well of ELISPOT plate containing a fixed anti-mouse IFN-γ antigen, and co-cultured at 37° C. in 5% $CO_2$ for 20 hours. The number of the spot representing IFN-γ producing cells (spot number/$3\times10^6$ cells) was evaluated by ELISPOT method. The effects of Th2 cell differentiation inhibitors were studied using a variety of injections containing different antigens and helper peptides. Examples and Comparative examples and the mouse used are shown in Tables 27 to 35. In each of the formulations shown as Examples, the level of immunity induction is enhanced by Th2 cell differentiation inhibitor. For each of Examples in which the results of evaluation are shown, the level of immunity induction was enhanced by Th2 cell differentiation inhibitor.

TABLE 27

| No. | administration route | dosage form | antigen name | amount [%] | Th2 cell differentiation inhibitor name | amount[%] | helper peptide name | amount [%] | Mouse for immunological evaluation | Results of immunization (ELISPOT) |
|---|---|---|---|---|---|---|---|---|---|---|
| Comparative example 42 | subcutaneous injection | injection | OVAp | 0.04 | — | — | PEP | 0.1 | C57BL/6 | 3 |
| Comparative example 43 | subcutaneous injection | injection | OVAp | 0.04 | — | — | PADRE | 0.1 | C57BL/6 | 5 |
| Example 310 | subcutaneous injection | injection | OVAp | 0.04 | loxoprofen(COX inhibitor) | 0.5 | PEP | 0.1 | C57BL/6 | 78 |
| Example 311 | subcutaneous injection | injection | OVAp | 0.04 | loxoprofen(COX inhibitor) | 0.5 | PADRE | 0.1 | C57BL/6 | 83 |
| Example 312 | subcutaneous injection | injection | OVAp | 0.04 | GW627368X(prostaglandin receptor antagonist) | 0.5 | PEP | 0.1 | C57BL/6 | 83 |
| Example 313 | subcutaneous injection | injection | OVAp | 0.04 | sulprostone(prostaglandin receptor agonist) | 0.5 | PEP | 0.1 | C57BL/6 | 76 |
| Example 314 | subcutaneous injection | injection | OVAp | 0.04 | quercetin(TSLP production inhibitor) | 0.5 | PEP | 0.1 | C57BL/6 | 105 |
| Example 315 | subcutaneous injection | injection | OVAp | 0.04 | quercetin(TSLP production inhibitor) | 0.5 | PADRE | 0.1 | C57BL/6 | 110 |
| Example 316 | subcutaneous injection | injection | OVAp | 0.04 | 2',5'-dideoxyadenosine (adenylate cyclase inhibitor) | 0.5 | PEP | 0.1 | C57BL/6 | 31 |
| Example 317 | subcutaneous injection | injection | OVAp | 0.04 | clofibrate(PPAR agonist) | 0.5 | PEP | 0.1 | C57BL/6 | 81 |
| Example 318 | subcutaneous injection | injection | OVAp | 0.04 | ropinirole(dopamine receptor agonist) | 0.5 | PEP | 0.1 | C57BL/6 | 37 |
| Example 319 | subcutaneous injection | injection | OVAp | 0.04 | proxyfan(histamine receptor agonist) | 0.5 | PEP | 0.1 | C57BL/6 | 61 |
| Example 320 | subcutaneous injection | injection | OVAp | 0.04 | diphenhydramine(histamine receptor antagonist) | 0.5 | PEP | 0.1 | C57BL/6 | 89 |
| Example 321 | subcutaneous injection | injection | OVAp | 0.04 | azelastine(histamine receptor antagonist) | 0.5 | PEP | 0.1 | C57BL/6 | 82 |
| Example 322 | subcutaneous injection | injection | OVAp | 0.04 | famotidine(histamine receptor antagonist) | 0.5 | PEP | 0.1 | C57BL/6 | 83 |
| Example 323 | subcutaneous injection | injection | OVAp | 0.04 | sumatriptan(serotonin receptor agonist) | 0.5 | PEP | 0.1 | C57BL/6 | 138 |
| Example 324 | subcutaneous injection | injection | OVAp | 0.04 | olanzapine(serotonin receptor antagonist) | 0.5 | PEP | 0.1 | C57BL/6 | 61 |
| Example 325 | subcutaneous injection | injection | OVAp | 0.04 | oxybutynin(muscarine receptor antagonist) | 0.5 | PEP | 0.1 | C57BL/6 | 62 |
| Example 326 | subcutaneous injection | injection | OVAp | 0.04 | tamsulosin(adrenalin receptor antagonist) | 0.5 | PEP | 0.1 | C57BL/6 | 62 |
| Example 327 | subcutaneous injection | injection | OVAp | 0.04 | propranolol(adrenalin receptor antagonist) | 0.5 | PEP | 0.1 | C57BL/6 | 53 |
| Example 328 | subcutaneous injection | injection | OVAp | 0.04 | xylazine(adrenalin receptor agonist) | 0.5 | PEP | 0.1 | C57BL/6 | 37 |
| Example 329 | subcutaneous injection | injection | OVAp | 0.04 | baclofen(GABA receptor agonist) | 0.5 | PEP | 0.1 | C57BL/6 | 36 |
| Example 330 | subcutaneous injection | injection | OVAp | 0.04 | loperamide(opioid receptor agonist) | 0.5 | PEP | 0.1 | C57BL/6 | 135 |

TABLE 27-continued

| No. | administration route | dosage form | antigen name | amount [%] | Th2 cell differentiation inhibitor name | amount[%] | helper peptide name | amount [%] | Mouse for immunological evaluation | Results of immunization (ELISPOT) |
|---|---|---|---|---|---|---|---|---|---|---|
| Example 331 | subcutaneous injection | injection | OVAp | 0.04 | adenosine diphosphate (ADP receptor agonist) | 0.5 | PEP | 0.1 | C57BL/6 | 38 |
| Example 332 | subcutaneous injection | injection | OVAp | 0.04 | montelukast(leukotriene receptor antagonist) | 0.5 | PEP | 0.1 | C57BL/6 | 42 |
| Example 333 | subcutaneous injection | injection | OVAp | 0.04 | melatonin(melatonin receptor agonist) | 0.5 | PEP | 0.1 | C57BL/6 | 111 |
| Example 334 | subcutaneous injection | injection | OVAp | 0.04 | L-AP4(metabotropic glutamate receptor agonist) | 0.5 | PEP | 0.1 | C57BL/6 | 52 |
| Example 335 | subcutaneous injection | injection | OVAp | 0.04 | tranilast(TGF-beta production inhibitor) | 0.5 | PEP | 0.1 | C57BL/6 | 54 |

OVAp: OVA peptide (SEQ ID NO: 16)
PEP: Peptide-25 (SEQ ID NO: 13) (helper peptide)
PADRE: PADRE (SEQ ID NO: 15) (helper peptide)

TABLE 28

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 44 | subcutaneous injection | injection | OVAp | 0.04 | — | — | C57BL/6 | 1 |
| Example 336 | subcutaneous injection | injection | OVAp | 0.04 | etodolac(COX inhibitor) | 0.5 | C57BL/6 | |
| Example 337 | subcutaneous injection | injection | OVAp | 0.04 | loxoprofen(COX inhibitor) | 0.5 | C57BL/6 | 56 |
| Example 338 | subcutaneous injection | injection | OVAp | 0.04 | indomethacin(COX inhibitor) | 0.5 | C57BL/6 | |
| Example 339 | subcutaneous injection | injection | OVAp | 0.04 | aspirin(COX inhibitor) | 0.5 | C57BL/6 | |
| Example 340 | subcutaneous injection | injection | OVAp | 0.04 | diclofenac(COX inhibitor) | 0.5 | C57BL/6 | |
| Example 341 | subcutaneous injection | injection | OVAp | 0.04 | ketoprofen(COX inhibitor) | 0.5 | C57BL/6 | |
| Example 342 | subcutaneous injection | injection | OVAp | 0.04 | celecoxib(COX inhibitor) | 0.5 | C57BL/6 | |
| Example 343 | subcutaneous injection | injection | OVAp | 0.04 | valdecoxib(COX inhibitor) | 0.5 | C57BL/6 | |
| Example 344 | subcutaneous injection | injection | OVAp | 0.04 | GW627368X(prostaglandin receptor antagonist) | 0.5 | C57BL/6 | 70 |
| Example 345 | subcutaneous injection | injection | OVAp | 0.04 | RO1138452(prostaglandin receptor antagonist) | 0.5 | C57BL/6 | |
| Example 346 | subcutaneous injection | injection | OVAp | 0.04 | BWA868C(prostaglandin receptor antagonist) | 0.5 | C57BL/6 | |
| Example 347 | subcutaneous injection | injection | OVAp | 0.04 | sulprostone(prostaglandin receptor agonist) | 0.5 | C57BL/6 | 53 |
| Example 348 | subcutaneous injection | injection | OVAp | 0.04 | cloprostenol(prostaglandin receptor agonist) | 0.5 | C57BL/6 | |
| Example 349 | subcutaneous injection | injection | OVAp | 0.04 | quercetin(TSLP production inhibitor) | 0.5 | C57BL/6 | 80 |
| Example 350 | subcutaneous injection | injection | OVAp | 0.04 | berberine(TSLP production inhibitor) | 0.5 | C57BL/6 | |
| Example 351 | subcutaneous injection | injection | OVAp | 0.04 | noscapine(TSLP production inhibitor) | 0.5 | C57BL/6 | |
| Example 352 | subcutaneous injection | injection | OVAp | 0.04 | 3,3'-diindolylmethane(TSLP production inhibitor) | 0.5 | C57BL/6 | |
| Example 353 | subcutaneous injection | injection | OVAp | 0.04 | xanthone(TSLP production inhibitor) | 0.5 | C57BL/6 | |
| Example 354 | subcutaneous injection | injection | OVAp | 0.04 | parthenolide(TSLP production inhibitor) | 0.5 | C57BL/6 | |
| Example 355 | subcutaneous injection | injection | OVAp | 0.04 | resveratrol(TSLP production inhibitor) | 0.5 | C57BL/6 | |
| Example 356 | subcutaneous injection | injection | OVAp | 0.04 | 2',5'-dideoxyadenosine(adenylate cyclase inhibitor) | 0.5 | C57BL/6 | 23 |
| Example 357 | subcutaneous injection | injection | OVAp | 0.04 | nicotinic acid(niacin)(adenylate cyclase inhibitor) | 0.5 | C57BL/6 | |
| Example 358 | subcutaneous injection | injection | OVAp | 0.04 | docosahexaenoic acid (omega-3 fatty acid) | 0.5 | C57BL/6 | |

TABLE 28-continued

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Example 359 | subcutaneous injection | injection | OVAp | 0.04 | clofibrate(PPAR agonist) | 0.5 | C57BL/6 | 65 |
| Example 360 | subcutaneous injection | injection | OVAp | 0.04 | fenofibrate(PPAR agonist) | 0.5 | C57BL/6 | |
| Example 361 | subcutaneous injection | injection | OVAp | 0.04 | SCH23390(dopamine receptor antagonist) | 0.5 | C57BL/6 | |
| Example 362 | subcutaneous injection | injection | OVAp | 0.04 | ropinirole(dopamine receptor agonist) | 0.5 | C57BL/6 | 28 |
| Example 363 | subcutaneous injection | injection | OVAp | 0.04 | rotigotine(dopamine receptor agonist) | 0.5 | C57BL/6 | |
| Example 364 | subcutaneous injection | injection | OVAp | 0.04 | Immepip(histamine receptor agonist) | 0.5 | C57BL/6 | |
| Example 365 | subcutaneous injection | injection | OVAp | 0.04 | proxyfan(histamine receptor agonist) | 0.5 | C57BL/6 | |
| Example 366 | subcutaneous injection | injection | OVAp | 0.04 | 4-methylhistamine(histamine receptor agonist) | 0.5 | C57BL/6 | |
| Example 367 | subcutaneous injection | injection | OVAp | 0.04 | diphenhydramine(histamine receptor antagonist) | 0.5 | C57BL/6 | 72 |
| Example 368 | subcutaneous injection | injection | OVAp | 0.04 | azelastine(histamine receptor antagonist) | 0.5 | C57BL/6 | 54 |
| Example 369 | subcutaneous injection | injection | OVAp | 0.04 | cimetidine(histamine receptor antagonist) | 0.5 | C57BL/6 | |
| Example 370 | subcutaneous injection | injection | OVAp | 0.04 | famotidine(histamine receptor antagonist) | 0.5 | C57BL/6 | 57 |
| Example 371 | subcutaneous injection | injection | OVAp | 0.04 | sumatriptan(serotonin receptor agonist) | 0.5 | C57BL/6 | 102 |
| Example 372 | subcutaneous injection | injection | OVAp | 0.04 | zolmitriptan(serotonin receptor agonist) | 0.5 | C57BL/6 | |
| Example 373 | subcutaneous injection | injection | OVAp | 0.04 | metergoline(serotonin receptor antagonist) | 0.5 | C57BL/6 | |
| Example 374 | subcutaneous injection | injection | OVAp | 0.04 | clozapine(serotonin receptor antagonist) | 0.5 | C57BL/6 | |
| Example 375 | subcutaneous injection | injection | OVAp | 0.04 | olanzapine(serotonin receptor antagonist) | 0.5 | C57BL/6 | |
| Example 376 | subcutaneous injection | injection | OVAp | 0.04 | yohimbine(serotonin receptor antagonist) | 0.5 | C57BL/6 | |
| Example 377 | subcutaneous injection | injection | OVAp | 0.04 | tolvaptan(vasopressin receptor antagonist) | 0.5 | C57BL/6 | |
| Example 378 | subcutaneous injection | injection | OVAp | 0.04 | desmopressin(vasopressin receptor agonist) | 0.5 | C57BL/6 | |
| Example 379 | subcutaneous injection | injection | OVAp | 0.04 | oxybutynin(muscarine receptor antagonist) | 0.5 | C57BL/6 | |
| Example 380 | subcutaneous injection | injection | OVAp | 0.04 | acetylcholine(muscarine receptor antagonist) | 0.5 | C57BL/6 | |
| Example 381 | subcutaneous injection | injection | OVAp | 0.04 | trimebutine(muscarine receptor antagonist) | 0.5 | C57BL/6 | |
| Example 382 | subcutaneous injection | injection | OVAp | 0.04 | pilocarpine(muscarine receptor agonist) | 0.5 | C57BL/6 | |
| Example 383 | subcutaneous injection | injection | OVAp | 0.04 | tamsulosin(adrenalin receptor antagonist) | 0.5 | C57BL/6 | 48 |
| Example 384 | subcutaneous injection | injection | OVAp | 0.04 | propranolol(adrenalin receptor antagonist) | 0.5 | C57BL/6 | 43 |
| Example 385 | subcutaneous injection | injection | OVAp | 0.04 | xylazine(adrenalin receptor agonist) | 0.5 | C57BL/6 | 26 |
| Example 386 | subcutaneous injection | injection | OVAp | 0.04 | novokinin(angiotensin receptor agonist) | 0.5 | C57BL/6 | |
| Example 387 | subcutaneous injection | injection | OVAp | 0.04 | baclofen(GABA receptor agonist) | 0.5 | C57BL/6 | 26 |
| Example 388 | subcutaneous injection | injection | OVAp | 0.04 | TRAP-6(thrombin receptor agonist) | 0.5 | C57BL/6 | |
| Example 389 | subcutaneous injection | injection | OVAp | 0.04 | loperamide(opioid receptor agonist) | 0.5 | C57BL/6 | |
| Example 390 | subcutaneous injection | injection | OVAp | 0.04 | adenosine diphosphate(ADP receptor agonist) | 0.5 | C57BL/6 | 28 |
| Example 391 | subcutaneous injection | injection | OVAp | 0.04 | montelukast(leukotriene receptor antagonist) | 0.5 | C57BL/6 | 33 |
| Example 392 | subcutaneous injection | injection | OVAp | 0.04 | zileuton(leukotriene receptor antagonist) | 0.5 | C57BL/6 | |
| Example 393 | subcutaneous injection | injection | OVAp | 0.04 | leukotriene B4(leukotriene receptor agonist) | 0.5 | C57BL/6 | |
| Example 394 | subcutaneous injection | injection | OVAp | 0.04 | melatonin(melatonin receptor agonist) | 0.5 | C57BL/6 | 95 |
| Example 395 | subcutaneous injection | injection | OVAp | 0.04 | somatostatin-14(somatostatin receptor agonist) | 0.5 | C57BL/6 | |

TABLE 28-continued

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Example 396 | subcutaneous injection | injection | OVAp | 0.04 | GW405833(cannabinoid receptor agonist) | 0.5 | C57BL/6 | |
| Example 397 | subcutaneous injection | injection | OVAp | 0.04 | SEW2871(sphingosine-1 phosphate receptor agonist) | 0.5 | C57BL/6 | |
| Example 398 | subcutaneous injection | injection | OVAp | 0.04 | biphenylindanone A(metabotropic glutamate receptor agonist) | 0.5 | C57BL/6 | |
| Example 399 | subcutaneous injection | injection | OVAp | 0.04 | L-AP4(metabotropic glutamate receptor agonist) | 0.5 | C57BL/6 | |
| Example 400 | subcutaneous injection | injection | OVAp | 0.04 | glycyrrhizic acid(phospholipase A2 inhibitor) | 0.5 | C57BL/6 | |
| Example 401 | subcutaneous injection | injection | OVAp | 0.04 | pirfenidone(TGF-beta production inhibitor) | 0.5 | C57BL/6 | |
| Example 402 | subcutaneous injection | injection | OVAp | 0.04 | tranilast(TGF-beta production inhibitor) | 0.5 | C57BL/6 | |
| Example 403 | subcutaneous injection | injection | OVAp | 0.04 | suplatast tosylate(Th2 cytokine inhibitor) | 0.5 | C57BL/6 | |

OVAp: OVA peptide(SEQ ID NO: 16)

TABLE 29

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 45 | subcutaneous injection | injection | HER2/neu_A24 | 0.04 | — | — | BALB/c | |
| Example 404 | subcutaneous injection | injection | HER2/neu_A24 | 0.04 | loxoprofen(COX inhibitor) | 0.5 | BALB/c | |
| Example 405 | subcutaneous injection | injection | HER2/neu A24 | 0.04 | GW627368X(prostaglandin receptor antagonist) | 0.5 | BALB/c | |
| Example 406 | subcutaneous injection | injection | HER2/neu A24 | 0.04 | sulprostone(prostaglandin receptor agonist) | 0.5 | BALB/c | |
| Example 407 | subcutaneous injection | injection | HER2/neu A24 | 0.04 | quercetin(TSLP production inhibitor) | 0.5 | BALB/c | |
| Example 408 | subcutaneous injection | injection | HER2/neu A24 | 0.04 | clofibrate(PPAR agonist) | 0.5 | BALB/c | |
| Example 409 | subcutaneous injection | injection | HER2/neu_A24 | 0.04 | famotidine(histamine receptor antagonist) | 0.5 | BALB/c | |
| Example 410 | subcutaneous injection | injection | HER2/neu_A24 | 0.04 | sumatriptan(serotonin receptor agonist) | 0.5 | BALB/c | |
| Example 411 | subcutaneous injection | injection | HER2/neu_A24 | 0.04 | loperamide(opioid receptor agonist) | 0.5 | BALB/c | |
| Example 412 | subcutaneous injection | injection | HER2/neu_A24 | 0.04 | melatonin(melatonin receptor agonist) | 0.5 | BALB/c | |

TABLE 30

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 46 | subcutaneous injection | injection | IPEP87 | 0.04 | — | — | genetically modified | |
| Example 413 | subcutaneous injection | injection | IPEP87 | 0.04 | loxoprofen(COX inhibitor) | 0.5 | genetically modified | |
| Example 414 | subcutaneous injection | injection | IPEP87 | 0.04 | GW627368X(prostaglandin receptor antagonist) | 0.5 | genetically modified | |
| Example 415 | subcutaneous injection | injection | IPEP87 | 0.04 | sulprostone(prostaglandin receptor agonist) | 0.5 | genetically modified | |
| Example 416 | subcutaneous injection | injection | IPEP87 | 0.04 | quercetin(TSLP production inhibitor) | 0.5 | genetically modified | |
| Example 417 | subcutaneous injection | injection | IPEP87 | 0.04 | clofibrate(PPAR agonist) | 0.5 | genetically modified | |

TABLE 30-continued

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Example 418 | subcutaneous injection | injection | IPEP87 | 0.04 | famotidine(histamine receptor antagonist) | 0.5 | genetically modified | |
| Example 419 | subcutaneous injection | injection | IPEP87 | 0.04 | sumatriptan(serotonin receptor agonist) | 0.5 | genetically modified | |
| Example 420 | subcutaneous injection | injection | IPEP87 | 0.04 | loperamide(opioid receptor agonist) | 0.5 | genetically modified | |
| Example 421 | subcutaneous injection | injection | IPEP87 | 0.04 | melatonin(melatonin receptor agonist) | 0.5 | genetically modified | |

TABLE 31

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 47 | subcutaneous injection | injection | HER2/neu E75 | 0.04 | — | — | genetically modified | |
| Example 422 | subcutaneous injection | injection | HER2/neu E75 | 0.04 | loxoprofen(COX inhibitor) | 0.5 | genetically modified | |
| Example 423 | subcutaneous injection | injection | HER2/neu E75 | 0.04 | GW627368X(prostaglandin receptor antagonist) | 0.5 | genetically modified | |
| Example 424 | subcutaneous injection | injection | HER2/neu E75 | 0.04 | sulprostone(prostaglandin receptor agonist) | 0.5 | genetically modified | |
| Example 425 | subcutaneous injection | injection | HER2/neu E75 | 0.04 | quercetin(TSLP production inhibitor) | 0.5 | genetically modified | |
| Example 426 | subcutaneous injection | injection | HER2/neu E75 | 0.04 | clofibrate(PPAR agonist) | 0.5 | genetically modified | |
| Example 427 | subcutaneous injection | injection | HER2/neu E75 | 0.04 | famotidine(histamine receptor antagonist) | 0.5 | genetically modified | |
| Example 428 | subcutaneous injection | injection | HER2/neu E75 | 0.04 | sumatriptan(serotonin receptor agonist) | 0.5 | genetically modified | |
| Example 429 | subcutaneous injection | injection | HER2/neu E75 | 0.04 | loperamide(opioid receptor agonist) | 0.5 | genetically modified | |
| Example 430 | subcutaneous injection | injection | HER2/neu E75 | 0.04 | melatonin(melatonin receptor agonist) | 0.5 | genetically modified | |

TABLE 32

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 48 | subcutaneous injection | injection | HER2/neu_A02 | 0.04 | — | — | genetically modified | |
| Example 431 | subcutaneous injection | injection | HER2/neu_A02 | 0.04 | loxoprofen(COX inhibitor) | 0.5 | genetically modified | |
| Example 432 | subcutaneous injection | injection | HER2/neu_A02 | 0.04 | GW627368X(prostaglandin receptor antagonist) | 0.5 | genetically modified | |
| Example 433 | subcutaneous injection | injection | HER2/neu_A02 | 0.04 | sulprostone(prostaglandin receptor agonist) | 0.5 | genetically modified | |
| Example 434 | subcutaneous injection | injection | HER2/neu_A02 | 0.04 | quercetin(TSLP production inhibitor) | 0.5 | genetically modified | |
| Example 435 | subcutaneous injection | injection | HER2/neu_A02 | 0.04 | clofibrate(PPAR agonist) | 0.5 | genetically modified | |
| Example 436 | subcutaneous injection | injection | HER2/neu_A02 | 0.04 | famotidine(histamine receptor antagonist) | 0.5 | genetically modified | |
| Example 437 | subcutaneous injection | injection | HER2/neu_A02 | 0.04 | sumatriptan(serotonin receptor agonist) | 0.5 | genetically modified | |
| Example 438 | subcutaneous injection | injection | HER2/neu_A02 | 0.04 | loperamide(opioid receptor agonist) | 0.5 | genetically modified | |
| Example 439 | subcutaneous injection | injection | HER2/neu_A02 | 0.04 | melatonin(melatonin receptor agonist) | 0.5 | genetically modified | |

TABLE 33

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 49 | subcutaneous injection | injection | MAGE3_A02 | 0.04 | — | — | genetically modified | 1 |
| Example 440 | subcutaneous injection | injection | MAGE3_A02 | 0.04 | loxoprofen(COX inhibitor) | 0.5 | genetically modified | 53 |
| Example 441 | subcutaneous injection | injection | MAGE3_A02 | 0.04 | GW627368X(prostaglandin receptor antagonist) | 0.5 | genetically modified | |
| Example 442 | subcutaneous injection | injection | MAGE3_A02 | 0.04 | sulprostone(prostaglandin receptor agonist) | 0.5 | genetically modified | |
| Example 443 | subcutaneous injection | injection | MAGE3_A02 | 0.04 | quercetin(TSLP production inhibitor) | 0.5 | genetically modified | |
| Example 444 | subcutaneous injection | injection | MAGE3_A02 | 0.04 | clofibrate(PPAR agonist) | 0.5 | genetically modified | |
| Example 445 | subcutaneous injection | injection | MAGE3_A02 | 0.04 | famotidine(histamine receptor antagonist) | 0.5 | genetically modified | |
| Example 446 | subcutaneous injection | injection | MAGE3_A02 | 0.04 | sumatriptan(serotonin receptor agonist) | 0.5 | genetically modified | |
| Example 447 | subcutaneous injection | injection | MAGE3_A02 | 0.04 | loperamide(opioid receptor agonist) | 0.5 | genetically modified | |
| Example 448 | subcutaneous injection | injection | MAGE3_A02 | 0.04 | melatonin(melatonin receptor agonist) | 0.5 | genetically modified | |

TABLE 34

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 50 | subcutaneous injection | injection | HBVenv | 0.04 | — | — | genetically modified | |
| Example 449 | subcutaneous injection | injection | HBVenv | 0.04 | loxoprofen(COX inhibitor) | 0.5 | genetically modified | |
| Example 450 | subcutaneous injection | injection | HBVenv | 0.04 | GW627368X(prostaglandin receptor antagonist) | 0.5 | genetically modified | |
| Example 451 | subcutaneous injection | injection | HBVenv | 0.04 | sulprostone(prostaglandin receptor agonist) | 0.5 | genetically modified | |
| Example 452 | subcutaneous injection | injection | HBVenv | 0.04 | quercetin(TSLP production inhibitor) | 0.5 | genetically modified | |
| Example 453 | subcutaneous injection | injection | HBVenv | 0.04 | clofibrate(PPAR agonist) | 0.5 | genetically modified | |
| Example 454 | subcutaneous injection | injection | HBVenv | 0.04 | famotidine(histamine receptor antagonist) | 0.5 | genetically modified | |
| Example 455 | subcutaneous injection | injection | HBVenv | 0.04 | sumatriptan(serotonin receptor agonist) | 0.5 | genetically modified | |
| Example 456 | subcutaneous injection | injection | HBVenv | 0.04 | loperamide(opioid receptor agonist) | 0.5 | genetically modified | |
| Example 457 | subcutaneous injection | injection | HBVenv | 0.04 | melatonin(melatonin receptor agonist) | 0.5 | genetically modified | |

TABLE 35

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 51 | subcutaneous injection | injection | OVA protein | 0.04 | — | — | C57BL/6 | |
| Example 458 | subcutaneous injection | injection | OVA protein | 0.04 | loxoprofen(COX inhibitor) | 0.5 | C57BL/6 | |
| Example 459 | subcutaneous injection | injection | OVA protein | 0.04 | GW627368X(prostaglandin receptor antagonist) | 0.5 | C57BL/6 | |
| Example 460 | subcutaneous injection | injection | OVA protein | 0.04 | sulprostone(prostaglandin receptor agonist) | 0.5 | C57BL/6 | |
| Example 461 | subcutaneous injection | injection | OVA protein | 0.04 | quercetin(TSLP production inhibitor) | 0.5 | C57BL/6 | |

TABLE 35-continued

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Example 462 | subcutaneous injection | injection | OVA protein | 0.04 | clofibrate(PPAR agonist) | 0.5 | C57BL/6 | |
| Example 463 | subcutaneous injection | injection | OVA protein | 0.04 | famotidine(histamine receptor antagonist) | 0.5 | C57BL/6 | |
| Example 464 | subcutaneous injection | injection | OVA protein | 0.04 | sumatriptan(serotonin receptor agonist) | 0.5 | C57BL/6 | |
| Example 465 | subcutaneous injection | injection | OVA protein | 0.04 | loperamide(opioid receptor agonist) | 0.5 | C57BL/6 | |
| Example 466 | subcutaneous injection | injection | OVA protein | 0.04 | melatonin(melatonin receptor agonist) | 0.5 | C57BL/6 | |

Preparation Liquid Formulation for Nasal Administration

The liquid formulations for nasal administration having ingredients as shown in Tables 36 to 45 were prepared to obtain samples for an immunization test. Specifically, saline as the base was added to an antigen (a peptide or a protein), a Th2 cell differentiation inhibitor and a helper peptide in an amount as shown in Table 7, and 20 parts by weight of an additive (dimethyl sulfoxide), to the total of 100 parts by weight, and then blended to prepare the liquid formulations.

Mouse Immunization Test with Liquid Formulation for Nasal Administration

The liquid formulations for nasal administration prepared as described above were used in a mouse immunization test using a model animal for immunological evaluation. The immunity induction level was evaluated by ELISPOT method. Specifically, a mouse was anesthetized, and then 10 µL of each liquid formulation for nasal administration was administered through the nasal cavity of the mouse. After 1 week, 10 µL of each liquid formulation for nasal administration was again administered through the nasal cavity of the mouse. After 6 days, the level of the cellular immunity induction specific for the antigen was evaluated. Six days after the administration, the spleen of the mouse was removed to prepare a suspension of spleen cells. Spleen cells ($3 \times 10^6$ cells/well) and an antigen peptide (100 µM) were added with a culture solution to a well of ELISPOT plate containing a fixed anti-mouse IFN-γ antigen, and co-cultured at 37° C. in 5% $CO_2$ for 20 hours. The number of the spot representing IFN-γ producing cells (spot number/$3 \times 10^6$ cells) was evaluated. The effects of Th2 cell differentiation inhibitors were studied using a variety of liquid formulations for nasal administration containing different antigens and helper peptides. Examples and Comparative examples and the mouse used are shown in Tables 36 to 45. In each of the formulations shown as Examples, the level of immunity induction is enhanced by Th2 cell differentiation inhibitor. For each of Examples in which the results of evaluation are shown, the level of immunity induction was enhanced by Th2 cell differentiation inhibitor.

TABLE 36

| No. | administration route | dosage form | antigen name | amount [%] | Th2 cell differentiation inhibitor name | amount [%] | helper peptide name | amount [%] | Mouse for immunological evaluation | Results of immunization (ELISPOT) |
|---|---|---|---|---|---|---|---|---|---|---|
| Comparative example 52 | nasal | liquid formulation | OVAp | 0.2 | — | — | PEP | 0.1 | C57BL/6 | 15 |
| Comparative example 53 | nasal | liquid formulation | OVAp | 0.2 | — | — | PADRE | 0.1 | C57BL/6 | 18 |
| Example 467 | nasal | liquid formulation | OVAp | 0.2 | etodolac (COX inhibitor) | 0.5 | PEP | 0.1 | C57BL/6 | |
| Example 468 | nasal | liquid formulation | OVAp | 0.2 | loxoprofen (COX inhibitor) | 0.5 | PEP | 0.1 | C57BL/6 | 69 |
| Example 469 | nasal | liquid formulation | OVAp | 0.2 | loxoprofen (COX inhibitor) | 0.5 | PADRE | 0.1 | C57BL/6 | 73 |
| Example 470 | nasal | liquid formulation | OVAp | 0.2 | indomethacin(COX inhibitor) | 0.5 | PADRE | 0.1 | C57BL/6 | |
| Example 471 | nasal | liquid formulation | OVAp | 0.2 | aspirin(COX inhibitor) | 0.5 | PADRE | 0.1 | C57BL/6 | |
| Example 472 | nasal | liquid formulation | OVAp | 0.2 | diclofenac (COX inhibitor) | 0.5 | PEP | 0.1 | C57BL/6 | |
| Example 473 | nasal | liquid formulation | OVAp | 0.2 | ketoprofen(COX inhibitor) | 0.5 | PADRE | 0.1 | C57BL/6 | |
| Example 474 | nasal | liquid formulation | OVAp | 0.2 | celecoxib(COX inhibitor) | 0.5 | PADRE | 0.1 | C57BL/6 | |
| Example 475 | nasal | liquid formulation | OVAp | 0.2 | valdecoxib(COX inhibitor) | 0.5 | PADRE | 0.1 | C57BL/6 | |
| Example 476 | nasal | liquid formulation | OVAp | 0.2 | GW627368X(prostaglandin receptor antagonist) | 0.5 | PEP | 0.1 | C57BL/6 | 99 |
| Example 477 | nasal | liquid formulation | OVAp | 0.2 | BWA868C(prostaglandin receptor antagonist) | 0.5 | PEP | 0.1 | C57BL/6 | |
| Example 478 | nasal | liquid formulation | OVAp | 0.2 | RO1138452(prostaglandin receptor antagonist) | 0.5 | PEP | 0.1 | C57BL/6 | |

TABLE 36-continued

| No. | administration route | dosage form | antigen name | amount [%] | Th2 cell differentiation inhibitor name | amount [%] | helper peptide name | amount [%] | Mouse for immunological evaluation | Results of immunization (ELISPOT) |
|---|---|---|---|---|---|---|---|---|---|---|
| Example 479 | nasal | liquid formulation | OVAp | 0.2 | sulprostone(prostaglandin receptor agonist) | 0.5 | PEP | 0.1 | C57BL/6 | 89 |
| Example 480 | nasal | liquid formulation | OVAp | 0.2 | cloprostenol(prostaglandin receptor agonist) | 0.5 | PEP | 0.1 | C57BL/6 | 81 |
| Example 481 | nasal | liquid formulation | OVAp | 0.2 | quercetin(TSLP production inhibitor) | 0.5 | PEP | 0.1 | C57BL/6 | 51 |
| Example 482 | nasal | liquid formulation | OVAp | 0.2 | quercetin(TSLP production inhibitor) | 0.5 | PADRE | 0.1 | C57BL/6 | 58 |
| Example 483 | nasal | liquid formulation | OVAp | 0.2 | berberine(TSLP production inhibitor) | 0.5 | PEP | 0.1 | C57BL/6 | |
| Example 484 | nasal | liquid formulation | OVAp | 0.2 | noscapine(TSLP production inhibitor) | 0.5 | PEP | 0.1 | C57BL/6 | |
| Example 485 | nasal | liquid formulation | OVAp | 0.2 | 3,3'-diindolylmethane(TSLP production inhibitor) | 0.5 | PEP | 0.1 | C57BL/6 | |
| Example 486 | nasal | liquid formulation | OVAp | 0.2 | xanthone(TSLP production inhibitor) | 0.5 | PEP | 0.1 | C57BL/6 | |
| Example 487 | nasal | liquid formulation | OVAp | 0.2 | parthenolide(TSLP production inhibitor) | 0.5 | PEP | 0.1 | C57BL/6 | |
| Example 488 | nasal | liquid formulation | OVAp | 0.2 | resveratrol(TSLP production inhibitor) | 0.5 | PEP | 0.1 | C57BL/6 | 93 |
| Example 489 | nasal | liquid formulation | OVAp | 0.2 | 2',5'-dideoxyadenosine(adenylate cyclase inhibitor) | 0.5 | PEP | 0.1 | C57BL/6 | 34 |
| Example 490 | nasal | liquid formulation | OVAp | 0.2 | docosahexaenoic acid (omega-3 fatty acid) | 0.5 | PEP | 0.1 | C57BL/6 | |
| Example 491 | nasal | liquid formulation | OVAp | 0.2 | clofibrate (PPAR agonist) | 0.5 | PEP | 0.1 | C57BL/6 | 57 |
| Example 492 | nasal | liquid formulation | OVAp | 0.2 | fenofibrate (PPAR agonist) | 0.5 | PEP | 0.1 | C57BL/6 | |
| Example 493 | nasal | liquid formulation | OVAp | 0.2 | SCH23390(dopamine receptor antagonist) | 0.5 | PEP | 0.1 | C57BL/6 | |
| Example 494 | nasal | liquid formulation | OVAp | 0.2 | ropinirole(dopamine receptor agonist) | 0.5 | PEP | 0.1 | C57BL/6 | |
| Example 495 | nasal | liquid formulation | OVAp | 0.2 | rotigotine(dopamine receptor agonist) | 0.5 | PEP | 0.1 | C57BL/6 | |
| Example 496 | nasal | liquid formulation | OVAp | 0.2 | Immepip(histamine receptor agonist) | 0.5 | PEP | 0.1 | C57BL/6 | 41 |
| Example 497 | nasal | liquid formulation | OVAp | 0.2 | proxyfan(histamine receptor agonist) | 0.5 | PEP | 0.1 | C57BL/6 | |
| Example 498 | nasal | liquid formulation | OVAp | 0.2 | 4-methylhistamine(histamine receptor agonist) | 0.5 | PEP | 0.1 | C57BL/6 | |
| Example 499 | nasal | liquid formulation | OVAp | 0.2 | diphenhydramine(histamine receptor antagonist) | 0.5 | PEP | 0.1 | C57BL/6 | 54 |
| Example 500 | nasal | liquid formulation | OVAp | 0.2 | azelastine(histamine receptor antagonist) | 0.5 | PEP | 0.1 | C57BL/6 | |
| Example 501 | nasal | liquid formulation | OVAp | 0.2 | cimetidine(histamine receptor antagonist) | 0.5 | PEP | 0.1 | C57BL/6 | |
| Example 502 | nasal | liquid formulation | OVAp | 0.2 | famotidine(histamine receptor antagonist) | 0.5 | PEP | 0.1 | C57BL/6 | 51 |
| Example 503 | nasal | liquid formulation | OVAp | 0.2 | sumatriptan(serotonin receptor agonist) | 0.5 | PEP | 0.1 | C57BL/6 | 57 |
| Example 504 | nasal | liquid formulation | OVAp | 0.2 | zolmitriptan(serotonin receptor agonist) | 0.5 | PEP | 0.1 | C57BL/6 | |
| Example 505 | nasal | liquid formulation | OVAp | 0.2 | metergoline(serotonin receptor antagonist) | 0.5 | PEP | 0.1 | C57BL/6 | |
| Example 506 | nasal | liquid formulation | OVAp | 0.2 | clozapine(serotonin receptor antagonist) | 0.5 | PEP | 0.1 | C57BL/6 | |
| Example 507 | nasal | liquid formulation | OVAp | 0.2 | olanzapine(serotonin receptor antagonist) | 0.5 | PEP | 0.1 | C57BL/6 | 38 |
| Example 508 | nasal | liquid formulation | OVAp | 0.2 | yohimbine(serotonin receptor antagonist) | 0.5 | PEP | 0.1 | C57BL/6 | |
| Example 509 | nasal | liquid formulation | OVAp | 0.2 | tolvaptan(vasopressin receptor antagonist) | 0.5 | PEP | 0.1 | C57BL/6 | |
| Example 510 | nasal | liquid formulation | OVAp | 0.2 | desmopressin(vasopressin receptor agonist) | 0.5 | PEP | 0.1 | C57BL/6 | |
| Example 511 | nasal | liquid formulation | OVAp | 0.2 | oxybutynin(muscarine receptor antagonist) | 0.5 | PEP | 0.1 | C57BL/6 | 38 |
| Example 512 | nasal | liquid formulation | OVAp | 0.2 | acetylcholine(muscarine receptor antagonist) | 0.5 | PEP | 0.1 | C57BL/6 | |
| Example 513 | nasal | liquid formulation | OVAp | 0.2 | trimebutine(muscarine receptor antagonist) | 0.5 | PEP | 0.1 | C57BL/6 | |
| Example 514 | nasal | liquid formulation | OVAp | 0.2 | pilocarpine(muscarine receptor agonist) | 0.5 | PEP | 0.1 | C57BL/6 | |
| Example 515 | nasal | liquid formulation | OVAp | 0.2 | tamsulosin(adrenalin receptor antagonist) | 0.5 | PEP | 0.1 | C57BL/6 | 43 |

TABLE 36-continued

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Example 516 | nasal | liquid formulation | OVAp | 0.2 | propranolol(adrenalin receptor antagonist) | 0.5 | PEP | 0.1 | C57BL/6 | 39 |
| Example 517 | nasal | liquid formulation | OVAp | 0.2 | xylazine(adrenalin receptor agonist) | 0.5 | PEP | 0.1 | C57BL/6 | 27 |
| Example 518 | nasal | liquid formulation | OVAp | 0.2 | novokinin(angiotensin receptor agonist) | 0.5 | PEP | 0.1 | C57BL/6 | |
| Example 519 | nasal | liquid formulation | OVAp | 0.2 | baclofen(GABA receptor agonist) | 0.5 | PEP | 0.1 | C57BL/6 | |
| Example 520 | nasal | liquid formulation | OVAp | 0.2 | TRAP-6(thrombin receptor agonist) | 0.5 | PEP | 0.1 | C57BL/6 | |
| Example 521 | nasal | liquid formulation | OVAp | 0.2 | loperamide(opioid receptor agonist) | 0.5 | PEP | 0.1 | C57BL/6 | 55 |
| Example 522 | nasal | liquid formulation | OVAp | 0.2 | adenosine diphosphate(ADP receptor agonist) | 0.5 | PEP | 0.1 | C57BL/6 | 33 |
| Example 523 | nasal | liquid formulation | OVAp | 0.2 | montelukast(leukotriene receptor antagonist) | 0.5 | PEP | 0.1 | C57BL/6 | 31 |
| Example 524 | nasal | liquid formulation | OVAp | 0.2 | leukotriene B4(leukotriene receptor agonist) | 0.5 | PEP | 0.1 | C57BL/6 | |
| Example 525 | nasal | liquid formulation | OVAp | 0.2 | melatonin(melatonin receptor agonist) | 0.5 | PEP | 0.1 | C57BL/6 | 57 |
| Example 526 | nasal | liquid formulation | OVAp | 0.2 | somatostatin-14(somatostatin receptor agonist) | 0.5 | PEP | 0.1 | C57BL/6 | |
| Example 527 | nasal | liquid formulation | OVAp | 0.2 | GW405833(cannabinoid receptor agonist) | 0.5 | PEP | 0.1 | C57BL/6 | |
| Example 528 | nasal | liquid formulation | OVAp | 0.2 | SEW2871(sphingosine-1 phosphate receptor agonist) | 0.5 | PEP | 0.1 | C57BL/6 | |
| Example 529 | nasal | liquid formulation | OVAp | 0.2 | biphenylindanone A(metabotropic glutamate receptor agonist) | 0.5 | PEP | 0.1 | C57BL/6 | 41 |
| Example 530 | nasal | liquid formulation | OVAp | 0.2 | L-AP4(metabotropic glutamate receptor agonist) | 0.5 | PEP | 0.1 | C57BL/6 | |
| Example 531 | nasal | liquid formulation | OVAp | 0.2 | glycyrrhizic acid(phospholipase A2 inhibitor) | 0.5 | PEP | 0.1 | C57BL/6 | |
| Example 532 | nasal | liquid formulation | OVAp | 0.2 | pirfenidone(TGF-beta production inhibitor) | 0.5 | PEP | 0.1 | C57BL/6 | 40 |
| Example 533 | nasal | liquid formulation | OVAp | 0.2 | tranilast(TGF-beta production inhibitor) | 0.5 | PEP | 0.1 | C57BL/6 | |
| Example 534 | nasal | liquid formulation | OVAp | 0.2 | suplatast tosylate(Th2 cytokine inhibitor) | 0.5 | PEP | 0.1 | C57BL/6 | |

OVAp: OVA peptide (SEQ ID NO: 16)
PEP: Peptide-25 (SEQ ID NO: 13) (helper peptide)
PADRE: PADRE (SEQ ID NO: 15) (helper peptide)

TABLE 37

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Comparative example 54 | nasal | liquid formulation | HER2/neu E75 | 1.25 | — | — | PEP | 0.3 | genetically modified | 11 |
| Comparative example 55 | nasal | liquid formulation | HER2/neu E75 | 1.25 | — | — | PADRE | 0.3 | genetically modified | |
| Example 535 | nasal | liquid formulation | HER2/neu E75 | 1.25 | loxoprofen(COX inhibitor) | 0.1 | PEP | 0.3 | genetically modified | 125 |
| Example 536 | nasal | liquid formulation | HER2/neu E75 | 1.25 | loxoprofen(COX inhibitor) | 0.1 | PADRE | 0.3 | genetically modified | |
| Example 537 | nasal | liquid formulation | HER2/neu E75 | 1.25 | GW627368X (prostaglandin receptor antagonist) | 0.1 | PEP | 0.3 | genetically modified | 93 |
| Example 538 | nasal | liquid formulation | HER2/neu E75 | 1.25 | sulprostone (prostaglandin receptor agonist) | 0.1 | PEP | 0.3 | genetically modified | 114 |
| Example 539 | nasal | liquid formulation | HER2/neu E75 | 1.25 | cloprostenol (prostaglandin receptor agonist) | 0.1 | PEP | 0.3 | genetically modified | |
| Example 540 | nasal | liquid formulation | HER2/neu E75 | 1.25 | quercetin (TSLP production inhibitor) | 0.1 | PEP | 0.3 | genetically modified | |
| Example 541 | nasal | liquid formulation | HER2/neu E75 | 1.25 | quercetin (TSLP production inhibitor) | 0.1 | PADRE | 0.3 | genetically modified | |

TABLE 37-continued

| No. | administration route | dosage form | antigen name | amount [%] | Th2 cell differentiation inhibitor name | amount [%] | helper peptide name | amount [%] | Mouse for immunological evaluation | Results of immunization (ELISPOT) |
|---|---|---|---|---|---|---|---|---|---|---|
| Example 542 | nasal | liquid formulation | HER2/neu E75 | 1.25 | resveratrol (TSLP production inhibitor) | 0.1 | PEP | 0.3 | genetically modified | 132 |
| Example 543 | nasal | liquid formulation | HER2/neu E75 | 1.25 | 2',5'-dideoxyadenosine (adenylate cyclase inhibitor) | 0.1 | PEP | 0.3 | genetically modified | |
| Example 544 | nasal | liquid formulation | HER2/neu E75 | 1.25 | docosahexaenoic acid(omega-3 fatty acid) | 0.1 | PEP | 0.3 | genetically modified | |
| Example 545 | nasal | liquid formulation | HER2/neu E75 | 1.25 | clofibrate(PPAR agonist) | 0.1 | PEP | 0.3 | genetically modified | 87 |
| Example 546 | nasal | liquid formulation | HER2/neu E75 | 1.25 | SCH23390(dopamine receptor antagonist) | 0.1 | PEP | 0.3 | genetically modified | |
| Example 547 | nasal | liquid formulation | HER2/neu E75 | 1.25 | rotigotine(dopamine receptor agonist) | 0.1 | PEP | 0.3 | genetically modified | |
| Example 548 | nasal | liquid formulation | HER2/neu E75 | 1.25 | proxyfan(histamine receptor agonist) | 0.1 | PEP | 0.3 | genetically modified | |
| Example 549 | nasal | liquid formulation | HER2/neu E75 | 1.25 | diphenhydramine(histamine receptor antagonist) | 0.1 | PEP | 0.3 | genetically modified | |
| Example 550 | nasal | liquid formulation | HER2/neu E75 | 1.25 | famotidine(histamine receptor antagonist) | 0.1 | PEP | 0.3 | genetically modified | 84 |
| Example 551 | nasal | liquid formulation | HER2/neu E75 | 1.25 | zolmitriptan(serotonin receptor agonist) | 0.1 | PEP | 0.3 | genetically modified | 65 |
| Example 552 | nasal | liquid formulation | HER2/neu E75 | 1.25 | olanzapine(serotonin receptor antagonist) | 0.1 | PEP | 0.3 | genetically modified | |
| Example 553 | nasal | liquid formulation | HER2/neu E75 | 1.25 | tolvaptan(vasopressin receptor antagonist) | 0.1 | PEP | 0.3 | genetically modified | |
| Example 554 | nasal | liquid formulation | HER2/neu E75 | 1.25 | desmopressin(vasopressin receptor agonist) | 0.1 | PEP | 0.3 | genetically modified | |
| Example 555 | nasal | liquid formulation | HER2/neu E75 | 1.25 | trimebutine(muscarine receptor antagonist) | 0.1 | PEP | 0.3 | genetically modified | |
| Example 556 | nasal | liquid formulation | HER2/neu E75 | 1.25 | pilocarpine(muscarine receptor agonist) | 0.1 | PEP | 0.3 | genetically modified | |
| Example 557 | nasal | liquid formulation | HER2/neu E75 | 1.25 | tamsulosin(adrenalin receptor antagonist) | 0.1 | PEP | 0.3 | genetically modified | |
| Example 558 | nasal | liquid formulation | HER2/neu E75 | 1.25 | propranolol(adrenalin receptor antagonist) | 0.1 | PEP | 0.3 | genetically modified | |
| Example 559 | nasal | liquid formulation | HER2/neu E75 | 1.25 | xylazine(adrenalin receptor agonist) | 0.1 | PEP | 0.3 | genetically modified | |
| Example 560 | nasal | liquid formulation | HER2/neu E75 | 1.25 | novokinin(angiotensin receptor agonist) | 0.1 | PEP | 0.3 | genetically modified | |
| Example 561 | nasal | liquid formulation | HER2/neu E75 | 1.25 | baclofen(GABA receptor agonist) | 0.1 | PEP | 0.3 | genetically modified | |
| Example 562 | nasal | liquid formulation | HER2/neu E75 | 1.25 | TRAP-6(thrombin receptor agonist) | 0.1 | PEP | 0.3 | genetically modified | |
| Example 563 | nasal | liquid formulation | HER2/neu E75 | 1.25 | loperamide(opioid receptor agonist) | 0.1 | PEP | 0.3 | genetically modified | 67 |
| Example 564 | nasal | liquid formulation | HER2/neu E75 | 1.25 | adenosine diphosphate(ADP receptor agonist) | 0.1 | PEP | 0.3 | genetically modified | |
| Example 565 | nasal | liquid formulation | HER2/neu E75 | 1.25 | montelukast(leukotriene receptor antagonist) | 0.1 | PEP | 0.3 | genetically modified | |
| Example 566 | nasal | liquid formulation | HER2/neu E75 | 1.25 | leukotriene B4(leukotriene receptor agonist) | 0.1 | PEP | 0.3 | genetically modified | |
| Example 567 | nasal | liquid formulation | HER2/neu E75 | 1.25 | melatonin(melatonin receptor agonist) | 0.1 | PEP | 0.3 | genetically modified | 76 |
| Example 568 | nasal | liquid formulation | HER2/neu E75 | 1.25 | somatostatin-14(somatostatin receptor agonist) | 0.1 | PEP | 0.3 | genetically modified | |
| Example 569 | nasal | liquid formulation | HER2/neu E75 | 1.25 | GW405833 (cannabinoid receptor agonist) | 0.1 | PEP | 0.3 | genetically modified | |
| Example 570 | nasal | liquid formulation | HER2/neu E75 | 1.25 | SEW2871(sphingosine-1 phosphate receptor agonist) | 0.1 | PEP | 0.3 | genetically modified | |
| Example 571 | nasal | liquid formulation | HER2/neu E75 | 1.25 | L-AP4(metabotropic glutamate receptor agonist) | 0.1 | PEP | 0.3 | genetically modified | 56 |
| Example 572 | nasal | liquid formulation | HER2/neu E75 | 1.25 | dipotassium glycyrrhizinate(phospholipase A2 inhibitor) | 0.1 | PEP | 0.3 | genetically modified | |
| Example 573 | nasal | liquid formulation | HER2/neu E75 | 1.25 | pirfenidone(TGF-beta production inhibitor) | 0.1 | PEP | 0.3 | genetically modified | |

TABLE 37-continued

| No. | administration route | dosage form | antigen name | amount [%] | Th2 cell differentiation inhibitor name | amount [%] | helper peptide name | amount [%] | Mouse for immunological evaluation | Results of immunization (ELISPOT) |
|---|---|---|---|---|---|---|---|---|---|---|
| Example 574 | nasal | liquid formulation | HER2/neu E75 | 1.25 | suplatast tosylate(Th2 cytokine inhibitor) | 0.1 | PEP | 0.3 | genetically modified | |

PEP: Peptide-25 (SEQ ID NO: 13) (helper peptide)
PADRE: PADRE (SEQ ID NO: 15) (helper peptide)

TABLE 38

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 56 | nasal | liquid formulation | OVAp | 0.2 | — | — | C57BL/6 | 6 |
| Example 575 | nasal | liquid formulation | OVAp | 0.2 | etodolac(COX inhibitor) | 0.5 | C57BL/6 | |
| Example 576 | nasal | liquid formulation | OVAp | 0.2 | loxoprofen(COX inhibitor) | 0.5 | C57BL/6 | 52 |
| Example 577 | nasal | liquid formulation | OVAp | 0.2 | indomethacin(COX inhibitor) | 0.5 | C57BL/6 | |
| Example 578 | nasal | liquid formulation | OVAp | 0.2 | aspirin(COX inhibitor) | 0.5 | C57BL/6 | |
| Example 579 | nasal | liquid formulation | OVAp | 0.2 | diclofenac(COX inhibitor) | 0.5 | C57BL/6 | |
| Example 580 | nasal | liquid formulation | OVAp | 0.2 | ketoprofen(COX inhibitor) | 0.5 | C57BL/6 | |
| Example 581 | nasal | liquid formulation | OVAp | 0.2 | celecoxib(COX inhibitor) | 0.5 | C57BL/6 | |
| Example 582 | nasal | liquid formulation | OVAp | 0.2 | valdecoxib(COX inhibitor) | 0.5 | C57BL/6 | |
| Example 583 | nasal | liquid formulation | OVAp | 0.2 | GW627368X(prostaglandin receptor antagonist) | 0.5 | C57BL/6 | 80 |
| Example 584 | nasal | liquid formulation | OVAp | 0.2 | RO1138452(prostaglandin receptor antagonist) | 0.5 | C57BL/6 | |
| Example 585 | nasal | liquid formulation | OVAp | 0.2 | BWA868C(prostaglandin receptor antagonist) | 0.5 | C57BL/6 | |
| Example 586 | nasal | liquid formulation | OVAp | 0.2 | sulprostone(prostaglandin receptor agonist) | 0.5 | C57BL/6 | 71 |
| Example 587 | nasal | liquid formulation | OVAp | 0.2 | cloprostenol(prostaglandin receptor agonist) | 0.5 | C57BL/6 | 66 |
| Example 588 | nasal | liquid formulation | OVAp | 0.2 | quercetin(TSLP production inhibitor) | 0.5 | C57BL/6 | 43 |
| Example 589 | nasal | liquid formulation | OVAp | 0.2 | berberine(TSLP production inhibitor) | 0.5 | C57BL/6 | |
| Example 590 | nasal | liquid formulation | OVAp | 0.2 | noscapine(TSLP production inhibitor) | 0.5 | C57BL/6 | |
| Example 591 | nasal | liquid formulation | OVAp | 0.2 | 3,3'-diindolylmethane(TSLP production inhibitor) | 0.5 | C57BL/6 | |
| Example 592 | nasal | liquid formulation | OVAp | 0.2 | xanthone(TSLP production inhibitor) | 0.5 | C57BL/6 | |
| Example 593 | nasal | liquid formulation | OVAp | 0.2 | parthenolide(TSLP production inhibitor) | 0.5 | C57BL/6 | |
| Example 594 | nasal | liquid formulation | OVAp | 0.2 | resveratrol(TSLP production inhibitor) | 0.5 | C57BL/6 | 75 |
| Example 595 | nasal | liquid formulation | OVAp | 0.2 | 2',5'-dideoxyadenosine(adenylate cyclase inhibitor) | 0.5 | C57BL/6 | 23 |
| Example 596 | nasal | liquid formulation | OVAp | 0.2 | docosahexaenoic acid(omega-3 fatty acid) | 0.5 | C57BL/6 | |
| Example 597 | nasal | liquid formulation | OVAp | 0.2 | clofibrate(PPAR agonist) | 0.5 | C57BL/6 | 40 |
| Example 598 | nasal | liquid formulation | OVAp | 0.2 | fenofibrate(PPAR agonist) | 0.5 | C57BL/6 | |
| Example 599 | nasal | liquid formulation | OVAp | 0.2 | SCH23390(dopamine receptor antagonist) | 0.5 | C57BL/6 | |
| Example 600 | nasal | liquid formulation | OVAp | 0.2 | ropinirole(dopamine receptor agonist) | 0.5 | C57BL/6 | |
| Example 601 | nasal | liquid formulation | OVAp | 0.2 | rotigotine(dopamine receptor agonist) | 0.5 | C57BL/6 | |
| Example 602 | nasal | liquid formulation | OVAp | 0.2 | Immepip(histamine receptor agonist) | 0.5 | C57BL/6 | |

TABLE 38-continued

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Example 603 | nasal | liquid formulation | OVAp | 0.2 | proxyfan(histamine receptor agonist) | 0.5 | C57BL/6 | |
| Example 604 | nasal | liquid formulation | OVAp | 0.2 | 4-methylhistamine(histamine receptor agonist) | 0.5 | C57BL/6 | |
| Example 605 | nasal | liquid formulation | OVAp | 0.2 | diphenhydramine(histamine receptor antagonist) | 0.5 | C57BL/6 | 40 |
| Example 606 | nasal | liquid formulation | OVAp | 0.2 | azelastine(histamine receptor antagonist) | 0.5 | C57BL/6 | |
| Example 607 | nasal | liquid formulation | OVAp | 0.2 | cimetidine(histamine receptor antagonist) | 0.5 | C57BL/6 | |
| Example 608 | nasal | liquid formulation | OVAp | 0.2 | famotidine(histamine receptor antagonist) | 0.5 | C57BL/6 | 43 |
| Example 609 | nasal | liquid formulation | OVAp | 0.2 | sumatriptan(serotonin receptor agonist) | 0.5 | C57BL/6 | 47 |
| Example 610 | nasal | liquid formulation | OVAp | 0.2 | zolmitriptan(serotonin receptor agonist) | 0.5 | C57BL/6 | |
| Example 611 | nasal | liquid formulation | OVAp | 0.2 | metergoline(serotonin receptor antagonist) | 0.5 | C57BL/6 | |
| Example 612 | nasal | liquid formulation | OVAp | 0.2 | clozapine(serotonin receptor antagonist) | 0.5 | C57BL/6 | |
| Example 613 | nasal | liquid formulation | OVAp | 0.2 | olanzapine(serotonin receptor antagonist) | 0.5 | C57BL/6 | |
| Example 614 | nasal | liquid formulation | OVAp | 0.2 | yohimbine(serotonin receptor antagonist) | 0.5 | C57BL/6 | |
| Example 615 | nasal | liquid formulation | OVAp | 0.2 | tolvaptan(vasopressin receptor antagonist) | 0.5 | C57BL/6 | |
| Example 616 | nasal | liquid formulation | OVAp | 0.2 | desmopressin(vasopressin receptor agonist) | 0.5 | C57BL/6 | |
| Example 617 | nasal | liquid formulation | OVAp | 0.2 | oxybutynin(muscarine receptor antagonist) | 0.5 | C57BL/6 | |
| Example 618 | nasal | liquid formulation | OVAp | 0.2 | acetylcholine(muscarine receptor antagonist) | 0.5 | C57BL/6 | |
| Example 619 | nasal | liquid formulation | OVAp | 0.2 | trimebutine(muscarine receptor antagonist) | 0.5 | C57BL/6 | |
| Example 620 | nasal | liquid formulation | OVAp | 0.2 | pilocarpine(muscarine receptor agonist) | 0.5 | C57BL/6 | |
| Example 621 | nasal | liquid formulation | OVAp | 0.2 | tamsulosin(adrenalin receptor antagonist) | 0.5 | C57BL/6 | 36 |
| Example 622 | nasal | liquid formulation | OVAp | 0.2 | propranolol(adrenalin receptor antagonist) | 0.5 | C57BL/6 | 27 |
| Example 623 | nasal | liquid formulation | OVAp | 0.2 | xylazine(adrenalin receptor agonist) | 0.5 | C57BL/6 | 17 |
| Example 624 | nasal | liquid formulation | OVAp | 0.2 | novokinin(angiotensin receptor agonist) | 0.5 | C57BL/6 | |
| Example 625 | nasal | liquid formulation | OVAp | 0.2 | baclofen(GABA receptor agonist) | 0.5 | C57BL/6 | |
| Example 626 | nasal | liquid formulation | OVAp | 0.2 | TRAP-6(thrombin receptor agonist) | 0.5 | C57BL/6 | |
| Example 627 | nasal | liquid formulation | OVAp | 0.2 | loperamide(opioid receptor agonist) | 0.5 | C57BL/6 | 43 |
| Example 628 | nasal | liquid formulation | OVAp | 0.2 | adenosine diphosphate(ADP receptor agonist) | 0.5 | C57BL/6 | 23 |
| Example 629 | nasal | liquid formulation | OVAp | 0.2 | montelukast(leukotriene receptor antagonist) | 0.5 | C57BL/6 | 23 |
| Example 630 | nasal | liquid formulation | OVAp | 0.2 | leukotriene B4(leukotriene receptor agonist) | 0.5 | C57BL/6 | |
| Example 631 | nasal | liquid formulation | OVAp | 0.2 | melatonin(melatonin receptor agonist) | 0.5 | C57BL/6 | 43 |
| Example 632 | nasal | liquid formulation | OVAp | 0.2 | somatostatin-14(somatostatin receptor agonist) | 0.5 | C57BL/6 | |
| Example 633 | nasal | liquid formulation | OVAp | 0.2 | GW405833(cannabinoid receptor agonist) | 0.5 | C57BL/6 | |
| Example 634 | nasal | liquid formulation | OVAp | 0.2 | SEW2871(sphingosine-1 phosphate receptor agonist) | 0.5 | C57BL/6 | |
| Example 635 | nasal | liquid formulation | OVAp | 0.2 | biphenylindanone A(metabotropic glutamate receptor agonist) | 0.5 | C57BL/6 | |
| Example 636 | nasal | liquid formulation | OVAp | 0.2 | L-AP4(metabotropic glutamate receptor agonist) | 0.5 | C57BL/6 | |
| Example 637 | nasal | liquid formulation | OVAp | 0.2 | glycyrrhizic acid(phospholipase A2 inhibitor) | 0.5 | C57BL/6 | |
| Example 638 | nasal | liquid formulation | OVAp | 0.2 | pirfenidone(TGF-beta production inhibitor) | 0.5 | C57BL/6 | |
| Example 639 | nasal | liquid formulation | OVAp | 0.2 | tranilast(TGF-beta production inhibitor) | 0.5 | C57BL/6 | |

TABLE 38-continued

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Example 640 | nasal | liquid formulation | OVAp | 0.2 | suplatast tosylate(Th2 cytokine inhibitor) | 0.5 | C57BL/6 | |

OVAp: OVA peptide (SEQ ID NO: 16)

TABLE 39

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 57 | nasal | liquid formulation | HER2/neu_A24 | 1.25 | — | — | BALB/c | |
| Example 641 | nasal | liquid formulation | HER2/neu_A24 | 1.25 | loxoprofen(COX inhibitor) | 0.5 | BALB/c | |
| Example 642 | nasal | liquid formulation | HER2/neu_A24 | 1.25 | GW627368X(prostaglandin receptor antagonist) | 0.5 | BALB/c | |
| Example 643 | nasal | liquid formulation | HER2/neu_A24 | 1.25 | sulprostone(prostaglandin receptor agonist) | 0.5 | BALB/c | |
| Example 644 | nasal | liquid formulation | HER2/neu_A24 | 1.25 | quercetin(TSLP production inhibitor) | 0.5 | BALB/c | |
| Example 645 | nasal | liquid formulation | HER2/neu_A24 | 1.25 | clofibrate(PPAR agonist) | 0.5 | BALB/c | |
| Example 646 | nasal | liquid formulation | HER2/neu_A24 | 1.25 | famotidine(histamine receptor antagonist) | 0.5 | BALB/c | |
| Example 647 | nasal | liquid formulation | HER2/neu A24 | 1.25 | sumatriptan(serotonin receptor agonist) | 0.5 | BALB/c | |
| Example 648 | nasal | liquid formulation | HER2/neu_A24 | 1.25 | loperamide(opioid receptor agonist) | 0.5 | BALB/c | |
| Example 649 | nasal | liquid formulation | HER2/neu_A24 | 1.25 | melatonin(melatonin receptor agonist) | 0.5 | BALB/c | |

TABLE 40

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 58 | nasal | liquid formulation | IPEP87 | 1.25 | — | — | genetically modified | |
| Example 650 | nasal | liquid formulation | IPEP87 | 1.25 | loxoprofen(COX inhibitor) | 0.5 | genetically modified | |
| Example 651 | nasal | liquid formulation | IPEP87 | 1.25 | GW627368X(prostaglandin receptor antagonist) | 0.5 | genetically modified | |
| Example 652 | nasal | liquid formulation | IPEP87 | 1.25 | sulprostone(prostaglandin receptor agonist) | 0.5 | genetically modified | |
| Example 653 | nasal | liquid formulation | IPEP87 | 1.25 | quercetin(TSLP production inhibitor) | 0.5 | genetically modified | |
| Example 654 | nasal | liquid formulation | IPEP87 | 1.25 | clofibrate(PPAR agonist) | 0.5 | genetically modified | |
| Example 655 | nasal | liquid formulation | IPEP87 | 1.25 | famotidine(histamine receptor antagonist) | 0.5 | genetically modified | |
| Example 656 | nasal | liquid formulation | IPEP87 | 1.25 | sumatriptan(serotonin receptor agonist) | 0.5 | genetically modified | |
| Example 657 | nasal | liquid formulation | IPEP87 | 1.25 | loperamide(opioid receptor agonist) | 0.5 | genetically modified | |
| Example 658 | nasal | liquid formulation | IPEP87 | 1.25 | melatonin(melatonin receptor agonist) | 0.5 | genetically modified | |

TABLE 41

| No. | administration route | dosage form | antigen name | antigen amount [%] | Th2 cell differentiation inhibitor name | Th2 cell differentiation inhibitor amount [%] | Mouse for immunological evaluation | Results of immunization (ELISPOT) |
|---|---|---|---|---|---|---|---|---|
| Comparative example 59 | nasal | liquid formulation | HER2/neu E75 | 1.25 | — | — | genetically modified | 3 |
| Example 659 | nasal | liquid formulation | HER2/neu E75 | 1.25 | loxoprofen(COX inhibitor) | 0.5 | genetically modified | 89 |
| Example 660 | nasal | liquid formulation | HER2/neu E75 | 1.25 | GW627368X(prostaglandin receptor antagonist) | 0.5 | genetically modified | |
| Example 661 | nasal | liquid formulation | HER2/neu E75 | 1.25 | sulprostone(prostaglandin receptor agonist) | 0.5 | genetically modified | |
| Example 662 | nasal | liquid formulation | HER2/neu E75 | 1.25 | quercetin(TSLP production inhibitor) | 0.5 | genetically modified | |
| Example 663 | nasal | liquid formulation | HER2/neu E75 | 1.25 | clofibrate(PPAR agonist) | 0.5 | genetically modified | |
| Example 664 | nasal | liquid formulation | HER2/neu E75 | 1.25 | famotidine(histamine receptor antagonist) | 0.5 | genetically modified | |
| Example 665 | nasal | liquid formulation | HER2/neu E75 | 1.25 | sumatriptan(serotonin receptor agonist) | 0.5 | genetically modified | |
| Example 666 | nasal | liquid formulation | HER2/neu E75 | 1.25 | loperamide(opioid receptor agonist) | 0.5 | genetically modified | |
| Example 667 | nasal | liquid formulation | HER2/neu E75 | 1.25 | melatonin(melatonin receptor agonist) | 0.5 | genetically modified | |

TABLE 42

| No. | administration route | dosage form | antigen name | antigen amount [%] | Th2 cell differentiation inhibitor name | Th2 cell differentiation inhibitor amount [%] | Mouse for immunological evaluation | Results of immunization (ELISPOT) |
|---|---|---|---|---|---|---|---|---|
| Comparative example 60 | nasal | liquid formulation | HER2/neu__A02 | 1.25 | — | — | genetically modified | |
| Example 668 | nasal | liquid formulation | HER2/neu__A02 | 1.25 | loxoprofen(COX inhibitor) | 0.5 | genetically modified | |
| Example 669 | nasal | liquid formulation | HER2/neu__A02 | 1.25 | GW627368X(prostaglandin receptor antagonist) | 0.5 | genetically modified | |
| Example 670 | nasal | liquid formulation | HER2/neu__A02 | 1.25 | sulprostone(prostaglandin receptor agonist) | 0.5 | genetically modified | |
| Example 671 | nasal | liquid formulation | HER2/neu__A02 | 1.25 | quercetin(TSLP production inhibitor) | 0.5 | genetically modified | |
| Example 672 | nasal | liquid formulation | HER2/neu__A02 | 1.25 | clofibrate(PPAR agonist) | 0.5 | genetically modified | |
| Example 673 | nasal | liquid formulation | HER2/neu__A02 | 1.25 | famotidine(histamine receptor antagonist) | 0.5 | genetically modified | |
| Example 674 | nasal | liquid formulation | HER2/neuA02 | 1.25 | sumatriptan(serotonin receptor agonist) | 0.5 | genetically modified | |
| Example 675 | nasal | liquid formulation | HER2/neu__A02 | 1.25 | loperamide(opioid receptor agonist) | 0.5 | genetically modified | |
| Example 676 | nasal | liquid formulation | HER2/neu__A02 | 1.25 | melatonin(melatonin receptor agonist) | 0.5 | genetically modified | |

TABLE 43

| No. | administration route | dosage form | antigen name | antigen amount [%] | Th2 cell differentiation inhibitor name | Th2 cell differentiation inhibitor amount [%] | Mouse for immunological evaluation | Results of immunization (ELISPOT) |
|---|---|---|---|---|---|---|---|---|
| Comparative example 61 | nasal | liquid formulation | MAGE3__A02 | 1.25 | — | — | genetically modified | |
| Example 677 | nasal | liquid formulation | MAGE3__A02 | 1.25 | loxoprofen(COX inhibitor) | 0.5 | genetically modified | |
| Example 678 | nasal | liquid formulation | MAGE3__A02 | 1.25 | GW627368X(prostaglandin receptor antagonist) | 0.5 | genetically modified | |
| Example 679 | nasal | liquid formulation | MAGE3__A02 | 1.25 | sulprostone(prostaglandin receptor agonist) | 0.5 | genetically modified | |
| Example 680 | nasal | liquid formulation | MAGE3__A02 | 1.25 | quercetin(TSLP production inhibitor) | 0.5 | genetically modified | |

TABLE 43-continued

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Example 681 | nasal | liquid formulation | MAGE3_A02 | 1.25 | clofibrate(PPAR agonist) | 0.5 | genetically modified | |
| Example 682 | nasal | liquid formulation | MAGE3_A02 | 1.25 | famotidine(histamine receptor antagonist) | 0.5 | genetically modified | |
| Example 683 | nasal | liquid formulation | MAGE3_A02 | 1.25 | sumatriptan(serotonin receptor agonist) | 0.5 | genetically modified | |
| Example 684 | nasal | liquid formulation | MAGE3_A02 | 1.25 | loperamide(opioid receptor agonist) | 0.5 | genetically modified | |
| Example 685 | nasal | liquid formulation | MAGE3_A02 | 1.25 | melatonin(melatonin receptor agonist) | 0.5 | genetically modified | |

TABLE 44

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 62 | nasal | liquid formulation | HBVenv | 1.25 | — | — | genetically modified | |
| Example 686 | nasal | liquid formulation | HBVenv | 1.25 | loxoprofen(COX inhibitor) | 0.5 | genetically modified | |
| Example 687 | nasal | liquid formulation | HBVenv | 1.25 | GW627368X(prostaglandin receptor antagonist) | 0.5 | genetically modified | |
| Example 688 | nasal | liquid formulation | HBVenv | 1.25 | sulprostone(prostaglandin receptor agonist) | 0.5 | genetically modified | |
| Example 689 | nasal | liquid formulation | HBVenv | 1.25 | quercetin(TSLP production inhibitor) | 0.5 | genetically modified | |
| Example 690 | nasal | liquid formulation | HBVenv | 1.25 | clofibrate(PPAR agonist) | 0.5 | genetically modified | |
| Example 691 | nasal | liquid formulation | HBVenv | 1.25 | famotidine(histamine receptor antagonist) | 0.5 | genetically modified | |
| Example 692 | nasal | liquid formulation | HBVenv | 1.25 | sumatriptan(serotonin receptor agonist) | 0.5 | genetically modified | |
| Example 693 | nasal | liquid formulation | HBVenv | 1.25 | loperamide(opioid receptor agonist) | 0.5 | genetically modified | |
| Example 694 | nasal | liquid formulation | HBVenv | 1.25 | melatonin(melatonin receptor agonist) | 0.5 | genetically modified | |

TABLE 45

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 63 | nasal | liquid formulation | OVA protein | 0.2 | — | — | C57BL/6 | |
| Example 695 | nasal | liquid formulation | OVA protein | 0.2 | loxoprofen(COX inhibitor) | 0.5 | C57BL/6 | |
| Example 696 | nasal | liquid formulation | OVA protein | 0.2 | GW627368X(prostaglandin receptor antagonist) | 0.5 | C57BL/6 | |
| Example 697 | nasal | liquid formulation | OVA protein | 0.2 | sulprostone(prostaglandin receptor agonist) | 0.5 | C57BL/6 | |
| Example 698 | nasal | liquid formulation | OVA protein | 0.2 | quercetin(TSLP production inhibitor) | 0.5 | C57BL/6 | |
| Example 699 | nasal | liquid formulation | OVA protein | 0.2 | clofibrate(PPAR agonist) | 0.5 | C57BL/6 | |
| Example 700 | nasal | liquid formulation | OVA protein | 0.2 | famotidine(histamine receptor antagonist) | 0.5 | C57BL/6 | |
| Example 701 | nasal | liquid formulation | OVA protein | 0.2 | sumatriptan(serotonin receptor agonist) | 0.5 | C57BL/6 | |
| Example 702 | nasal | liquid formulation | OVA protein | 0.2 | loperamide(opioid receptor agonist) | 0.5 | C57BL/6 | |
| Example 703 | nasal | liquid formulation | OVA protein | 0.2 | melatonin(melatonin receptor agonist) | 0.5 | C57BL/6 | |

Preparation of Liquid Formulation for Sublingual Administration

The liquid formulations for sublingual administration having ingredients as shown in Tables 46 to 55 were prepared to obtain samples for an immunization test. Specifically, saline as the based was added to an antigen (a peptide or a protein), a Th2 cell differentiation inhibitor and a helper peptide in an amount as shown in Tables 46 to 55, and 20 parts by weight of an additive (dimethyl sulfoxide), to the total of 100 parts by weight, and then blended to prepare the liquid formulations.

Mouse Immunization Test with Liquid Formulation for Sublingual Administration

The liquid formulations for sublingual administration prepared as described above were used in a mouse immunization test using a model animal for immunological evaluation. The immunity induction level was evaluated by ELISPOT method. Specifically, a mouse was anesthetized, and then 20 μL of each liquid formulation for sublingual administration was administered at sublingual region and then kept for 2 minutes. After 1 week, 20 μL of each liquid formulation for sublingual administration was again administered at sublingual region and then kept for 2 minutes. After 6 days, the level of the cellular immunity induction specific for the antigen was evaluated. Six days after the administration, the spleen of the mouse was removed to prepare a suspension of spleen cells. Spleen cells ($3\times10^6$ cells/well) and an antigen peptide (100 μM) were added with a culture solution to a well of ELISPOT plate containing a fixed anti-mouse IFN-γ antigen, and co-cultured at 37° C. in 5% $CO_2$ for 20 hours. The number of the spot representing IFN-γ producing cells (spot number/$3\times10^6$ cells) was evaluated by ELISPOT method. The effects of Th2 cell differentiation inhibitors were studied using a variety of liquid formulations for sublingual administration containing different antigens and helper peptides. Examples and Comparative examples and the mouse used are shown in Tables 46 to 55. In each of the formulations shown as Examples, the level of immunity induction is enhanced by Th2 cell differentiation inhibitor. For each of Examples in which the results of evaluation are shown, the level of immunity induction was enhanced by Th2 cell differentiation inhibitor.

TABLE 46

| No. | administration route | dosage form | antigen name | amount [%] | Th2 cell differentiation inhibitor name | amount [%] | helper peptide name | amount [%] | Mouse for immunological evaluation | Results of immunization (ELISPOT) |
|---|---|---|---|---|---|---|---|---|---|---|
| Comparative example 64 | sublingual | liquid formulation | OVAp | 1 | — | — | PEP | 0.5 | C57BL/6 | 0 |
| Comparative example 65 | sublingual | liquid formulation | OVAp | 1 | — | — | PADRE | 0.5 | C57BL/6 | 1 |
| Example 704 | sublingual | liquid formulation | OVAp | 1 | etodolac (COX inhibitor) | 1 | PEP | 0.5 | C57BL/6 | 52 |
| Example 705 | sublingual | liquid formulation | OVAp | 1 | loxoprofen (COX inhibitor) | 1 | PEP | 0.5 | C57BL/6 | 60 |
| Example 706 | sublingual | liquid formulation | OVAp | 1 | loxoprofen (COX inhibitor) | 1 | PADRE | 0.5 | C57BL/6 | 64 |
| Example 707 | sublingual | liquid formulation | OVAp | 1 | indomethacin (COX inhibitor) | 1 | PADRE | 0.5 | C57BL/6 | |
| Example 708 | sublingual | liquid formulation | OVAp | 1 | aspirin (COX inhibitor) | 1 | PADRE | 0.5 | C57BL/6 | |
| Example 709 | sublingual | liquid formulation | OVAp | 1 | diclofenac (COX inhibitor) | 1 | PEP | 0.5 | C57BL/6 | 58 |
| Example 710 | sublingual | liquid formulation | OVAp | 1 | ketoprofen (COX inhibitor) | 1 | PEP | 0.5 | C57BL/6 | 51 |
| Example 711 | sublingual | liquid formulation | OVAp | 1 | celecoxib (COX inhibitor) | 1 | PEP | 0.5 | C57BL/6 | 62 |
| Example 712 | sublingual | liquid formulation | OVAp | 1 | valdecoxib (COX inhibitor) | 1 | PADRE | 0.5 | C57BL/6 | |
| Example 713 | sublingual | liquid formulation | OVAp | 1 | GW627368X(prostaglandin receptor antagonist) | 1 | PEP | 0.5 | C57BL/6 | 53 |
| Example 714 | sublingual | liquid formulation | OVAp | 1 | RO1138452(prostaglandin receptor antagonist) | 1 | PEP | 0.5 | C57BL/6 | 50 |
| Example 715 | sublingual | liquid formulation | OVAp | 1 | BWA868C(prostaglandin receptor antagonist) | 1 | PEP | 0.5 | C57BL/6 | 55 |
| Example 716 | sublingual | liquid formulation | OVAp | 1 | sulprostone(prostaglandin receptor agonist) | 1 | PEP | 0.5 | C57BL/6 | 56 |
| Example 717 | sublingual | liquid formulation | OVAp | 1 | cloprostenol(prostaglandin receptor agonist) | 1 | PEP | 0.5 | C57BL/6 | |
| Example 718 | sublingual | liquid formulation | OVAp | 1 | quercetin(TSLP production inhibitor) | 1 | PEP | 0.5 | C57BL/6 | 58 |
| Example 719 | sublingual | liquid formulation | OVAp | 1 | quercetin(TSLP production inhibitor) | 1 | PADRE | 0.5 | C57BL/6 | |
| Example 720 | sublingual | liquid formulation | OVAp | 1 | berberine(TSLP production inhibitor) | 1 | PEP | 0.5 | C57BL/6 | |
| Example 721 | sublingual | liquid formulation | OVAp | 1 | noscapine(TSLP production inhibitor) | 1 | PEP | 0.5 | C57BL/6 | 56 |
| Example 722 | sublingual | liquid formulation | OVAp | 1 | 3,3'-diindolylmethane(TSLP production inhibitor) | 1 | PEP | 0.5 | C57BL/6 | 59 |
| Example 723 | sublingual | liquid formulation | OVAp | 1 | xanthone (TSLP production inhibitor) | 1 | PEP | 0.5 | C57BL/6 | 61 |
| Example 724 | sublingual | liquid formulation | OVAp | 1 | parthenolide (TSLP production inhibitor) | 1 | PEP | 0.5 | C57BL/6 | 68 |

TABLE 46-continued

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Example 725 | sublingual | liquid formulation | OVAp | 1 | resveratrol(TSLP production inhibitor) | 1 | PEP | 0.5 | C57BL/6 | |
| Example 726 | sublingual | liquid formulation | OVAp | 1 | 2',5'-dideoxyadenosine (adenylate cyclase inhibitor) | 1 | PEP | 0.5 | C57BL/6 | 23 |
| Example 727 | sublingual | liquid formulation | OVAp | 1 | docosahexaenoic acid (omega-3 fatty acid) | 1 | PEP | 0.5 | C57BL/6 | 12 |
| Example 728 | sublingual | liquid formulation | OVAp | 1 | clofibrate(PPAR agonist) | 1 | PEP | 0.5 | C57BL/6 | 51 |
| Example 729 | sublingual | liquid formulation | OVAp | 1 | fenofibrate (PPAR agonist) | 1 | PEP | 0.5 | C57BL/6 | |
| Example 730 | sublingual | liquid formulation | OVAp | 1 | SCH23390(dopamine receptor antagonist) | 1 | PEP | 0.5 | C57BL/6 | 23 |
| Example 731 | sublingual | liquid formulation | OVAp | 1 | ropinirole(dopamine receptor agonist) | 1 | PEP | 0.5 | C57BL/6 | |
| Example 732 | sublingual | liquid formulation | OVAp | 1 | rotigotine(dopamine receptor agonist) | 1 | PEP | 0.5 | C57BL/6 | 25 |
| Example 733 | sublingual | liquid formulation | OVAp | 1 | Immepip(histamine receptor agonist) | 1 | PEP | 0.5 | C57BL/6 | |
| Example 734 | sublingual | liquid formulation | OVAp | 1 | proxyfan(histamine receptor agonist) | 1 | PEP | 0.5 | C57BL/6 | 35 |
| Example 735 | sublingual | liquid formulation | OVAp | 1 | 4-methylhistamine(histamine receptor agonist) | 1 | PEP | 0.5 | C57BL/6 | 45 |
| Example 736 | sublingual | liquid formulation | OVAp | 1 | diphenhydramine(histamine receptor antagonist) | 1 | PEP | 0.5 | C57BL/6 | 53 |
| Example 737 | sublingual | liquid formulation | OVAp | 1 | azelastine(histamine receptor antagonist) | 1 | PEP | 0.5 | C57BL/6 | |
| Example 738 | sublingual | liquid formulation | OVAp | 1 | cimetidine(histamine receptor antagonist) | 1 | PEP | 0.5 | C57BL/6 | |
| Example 739 | sublingual | liquid formulation | OVAp | 1 | famotidine(histamine receptor antagonist) | 1 | PEP | 0.5 | C57BL/6 | 56 |
| Example 740 | sublingual | liquid formulation | OVAp | 1 | sumatriptan(serotonin receptor agonist) | 1 | PEP | 0.5 | C57BL/6 | |
| Example 741 | sublingual | liquid formulation | OVAp | 1 | zolmitriptan(serotonin receptor agonist) | 1 | PEP | 0.5 | C57BL/6 | 54 |
| Example 742 | sublingual | liquid formulation | OVAp | 1 | metergoline(serotonin receptor antagonist) | 1 | PEP | 0.5 | C57BL/6 | |
| Example 743 | sublingual | liquid formulation | OVAp | 1 | clozapine(serotonin receptor antagonist) | 1 | PEP | 0.5 | C57BL/6 | |
| Example 744 | sublingual | liquid formulation | OVAp | 1 | olanzapine(serotonin receptor antagonist) | 1 | PEP | 0.5 | C57BL/6 | 39 |
| Example 745 | sublingual | liquid formulation | OVAp | 1 | yohimbine(serotonin receptor antagonist) | 1 | PEP | 0.5 | C57BL/6 | |
| Example 746 | sublingual | liquid formulation | OVAp | 1 | tolvaptan(vasopressin receptor antagonist) | 1 | PEP | 0.5 | C57BL/6 | 18 |
| Example 747 | sublingual | liquid formulation | OVAp | 1 | desmopressin(vasopressin receptor agonist) | 1 | PEP | 0.5 | C57BL/6 | 21 |
| Example 748 | sublingual | liquid formulation | OVAp | 1 | oxybutynin(muscarine receptor antagonist) | 1 | PEP | 0.5 | C57BL/6 | 36 |
| Example 749 | sublingual | liquid formulation | OVAp | 1 | acetylcholine(muscarine receptor agonist) | 1 | PEP | 0.5 | C57BL/6 | |
| Example 750 | sublingual | liquid formulation | OVAp | 1 | trimebutine(muscarine receptor antagonist) | 1 | PEP | 0.5 | C57BL/6 | 43 |
| Example 751 | sublingual | liquid formulation | OVAp | 1 | pilocarpine(muscarine receptor agonist) | 1 | PEP | 0.5 | C57BL/6 | 18 |
| Example 752 | sublingual | liquid formulation | OVAp | 1 | tamsulosin(adrenalin receptor antagonist) | 1 | PEP | 0.5 | C57BL/6 | 39 |
| Example 753 | sublingual | liquid formulation | OVAp | 1 | propranolol(adrenalin receptor antagonist) | 1 | PEP | 0.5 | C57BL/6 | 37 |
| Example 754 | sublingual | liquid formulation | OVAp | 1 | xylazine(adrenalin receptor agonist) | 1 | PEP | 0.5 | C57BL/6 | 16 |
| Example 755 | sublingual | liquid formulation | OVAp | 1 | novokinin(angiotensin receptor agonist) | 1 | PEP | 0.5 | C57BL/6 | 17 |
| Example 756 | sublingual | liquid formulation | OVAp | 1 | baclofen(GABA receptor agonist) | 1 | PEP | 0.5 | C57BL/6 | 21 |
| Example 757 | sublingual | liquid formulation | OVAp | 1 | TRAP-6(thrombin receptor agonist) | 1 | PEP | 0.5 | C57BL/6 | |
| Example 758 | sublingual | liquid formulation | OVAp | 1 | loperamide(opioid receptor agonist) | 1 | PEP | 0.5 | C57BL/6 | 55 |
| Example 759 | sublingual | liquid formulation | OVAp | 1 | adenosine diphosphate(ADP receptor agonist) | 1 | PEP | 0.5 | C57BL/6 | 19 |
| Example 760 | sublingual | liquid formulation | OVAp | 1 | montelukast(leukotriene receptor antagonist) | 1 | PEP | 0.5 | C57BL/6 | 25 |
| Example 761 | sublingual | liquid formulation | OVAp | 1 | zileuton(leukotriene receptor antagonist) | 1 | PEP | 0.5 | C57BL/6 | 13 |

TABLE 46-continued

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Example 762 | sublingual | liquid formulation | OVAp | 1 | leukotriene B4(leukotriene receptor agonist) | 1 | PEP | 0.5 | C57BL/6 | |
| Example 763 | sublingual | liquid formulation | OVAp | 1 | melatonin(melatonin receptor agonist) | 1 | PEP | 0.5 | C57BL/6 | 53 |
| Example 764 | sublingual | liquid formulation | OVAp | 1 | somatostatin-14(somatostatin receptor agonist) | 1 | PEP | 0.5 | C57BL/6 | |
| Example 765 | sublingual | liquid formulation | OVAp | 1 | GW405833(cannabinoid receptor agonist) | 1 | PEP | 0.5 | C57BL/6 | |
| Example 766 | sublingual | liquid formulation | OVAp | 1 | SEW2871(sphingosine-1 phosphate receptor agonist) | 1 | PEP | 0.5 | C57BL/6 | |
| Example 767 | sublingual | liquid formulation | OVAp | 1 | biphenylindanone A(metabotropic glutamate receptor agonist) | 1 | PEP | 0.5 | C57BL/6 | |
| Example 768 | sublingual | liquid formulation | OVAp | 1 | L-AP4(metabotropic glutamate receptor agonist) | 1 | PEP | 0.5 | C57BL/6 | 43 |
| Example 769 | sublingual | liquid formulation | OVAp | 1 | dipotassium glycyrrhizinate (phospholipase A2 inhibitor) | 1 | PEP | 0.5 | C57BL/6 | 18 |
| Example 770 | sublingual | liquid formulation | OVAp | 1 | pirfenidone(TGF-beta production inhibitor) | 1 | PEP | 0.5 | C57BL/6 | 41 |
| Example 771 | sublingual | liquid formulation | OVAp | 1 | tranilast(TGF-beta production inhibitor) | 1 | PEP | 0.5 | C57BL/6 | |
| Example 772 | sublingual | liquid formulation | OVAp | 1 | suplatast tosylate(Th2 cytokine inhibitor) | 1 | PEP | 0.5 | C57BL/6 | |

OVAp: OVA peptide (SEQ ID NO: 16)
PEP: Peptide-25(SEQ ID NO: 13) (helper peptide)
PADRE: PADRE (SEQ ID NO: 15) (helper peptide)

TABLE 47

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Comparative example 66 | sublingual | liquid formulation | HER2/neu E75 | 1.25 | — | — | PEP | 0.3 | genetically modified | 11 |
| Comparative example 67 | sublingual | liquid formulation | HER2/neu E75 | 1.25 | — | — | PADRE | 0.3 | genetically modified | |
| Example 773 | sublingual | liquid formulation | HER2/neu E75 | 1.25 | etodolac(COX inhibitor) | 0.1 | PEP | 0.3 | genetically modified | 78 |
| Example 774 | sublingual | liquid formulation | HER2/neu E75 | 1.25 | loxoprofen(COX inhibitor) | 0.1 | PEP | 0.3 | genetically modified | 89 |
| Example 775 | sublingual | liquid formulation | HER2/neu E75 | 1.25 | loxoprofen(COX inhibitor) | 0.1 | PADRE | 0.3 | genetically modified | |
| Example 776 | sublingual | liquid formulation | HER2/neu E75 | 1.25 | indomethacin(COX inhibitor) | 0.1 | PADRE | 0.3 | genetically modified | |
| Example 777 | sublingual | liquid formulation | HER2/neu E75 | 1.25 | aspirin(COX inhibitor) | 0.1 | PADRE | 0.3 | genetically modified | |
| Example 778 | sublingual | liquid formulation | HER2/neu E75 | 1.25 | diclofenac(COX inhibitor) | 0.1 | PEP | 0.3 | genetically modified | |
| Example 779 | sublingual | liquid formulation | HER2/neu E75 | 1.25 | ketoprofen(COX inhibitor) | 0.1 | PEP | 0.3 | genetically modified | |
| Example 780 | sublingual | liquid formulation | HER2/neu E75 | 1.25 | celecoxib(COX inhibitor) | 0.1 | PEP | 0.3 | genetically modified | 123 |
| Example 781 | sublingual | liquid formulation | HER2/neu E75 | 1.25 | valdecoxib(COX inhibitor) | 0.1 | PADRE | 0.3 | genetically modified | |
| Example 782 | sublingual | liquid formulation | HER2/neu E75 | 1.25 | GW627368X(prostaglandin receptor antagonist) | 0.1 | PEP | 0.3 | genetically modified | 85 |
| Example 783 | sublingual | liquid formulation | HER2/neu E75 | 1.25 | RO1138452(prostaglandin receptor antagonist) | 0.1 | PEP | 0.3 | genetically modified | 87 |
| Example 784 | sublingual | liquid formulation | HER2/neu E75 | 1.25 | BWA868C(prostaglandin receptor antagonist) | 0.1 | PEP | 0.3 | genetically modified | 76 |
| Example 785 | sublingual | liquid formulation | HER2/neu E75 | 1.25 | sulprostone (prostaglandin receptor agonist) | 0.1 | PEP | 0.3 | genetically modified | 89 |
| Example 786 | sublingual | liquid formulation | HER2/neu E75 | 1.25 | cloprostenol (prostaglandin receptor agonist) | 0.1 | PEP | 0.3 | genetically modified | |
| Example 787 | sublingual | liquid formulation | HER2/neu E75 | 1.25 | quercetin(TSLP production inhibitor) | 0.1 | PEP | 0.3 | genetically modified | 94 |

TABLE 47-continued

| No. | administration route | dosage form | antigen name | amount [%] | Th2 cell differentiation inhibitor name | amount [%] | helper peptide name | amount [%] | Mouse for immunological evaluation | Results of immunization (ELISPOT) |
|---|---|---|---|---|---|---|---|---|---|---|
| Example 788 | sublingual | liquid formulation | HER2/neu E75 | 1.25 | quercetin(TSLP production inhibitor) | 0.1 | PADRE | 0.3 | genetically modified | |
| Example 789 | sublingual | liquid formulation | HER2/neu E75 | 1.25 | berberine(TSLP production inhibitor) | 0.1 | PADRE | 0.3 | genetically modified | |
| Example 790 | sublingual | liquid formulation | HER2/neu E75 | 1.25 | noscapine(TSLP production inhibitor) | 0.1 | PEP | 0.3 | genetically modified | 78 |
| Example 791 | sublingual | liquid formulation | HER2/neu E75 | 1.25 | 3,3'-diindolyl-methane(TSLP production inhibitor) | 0.1 | PEP | 0.3 | genetically modified | |
| Example 792 | sublingual | liquid formulation | HER2/neu E75 | 1.25 | xanthone(TSLP production inhibitor) | 0.1 | PEP | 0.3 | genetically modified | 110 |
| Example 793 | sublingual | liquid formulation | HER2/neu E75 | 1.25 | parthenolide(TSLP production inhibitor) | 0.1 | PEP | 0.3 | genetically modified | 105 |
| Example 794 | sublingual | liquid formulation | HER2/neu E75 | 1.25 | resveratrol(TSLP production inhibitor) | 0.1 | PEP | 0.3 | genetically modified | |
| Example 795 | sublingual | liquid formulation | HER2/neu E75 | 1.25 | 2',5'-dideoxy-adenosine(adenylate cyclase inhibitor) | 0.1 | PEP | 0.3 | genetically modified | |
| Example 796 | sublingual | liquid formulation | HER2/neu E75 | 1.25 | docosahexaenoic acid (omega-3 fatty acid) | 0.1 | PEP | 0.3 | genetically modified | |
| Example 797 | sublingual | liquid formulation | HER2/neu E75 | 1.25 | clofibrate(PPAR agonist) | 0.1 | PEP | 0.3 | genetically modified | 85 |
| Example 798 | sublingual | liquid formulation | HER2/neu E75 | 1.25 | fenofibrate(PPAR agonist) | 0.1 | PEP | 0.3 | genetically modified | |
| Example 799 | sublingual | liquid formulation | HER2/neu E75 | 1.25 | SCH23390(dopamine receptor antagonist) | 0.1 | PEP | 0.3 | genetically modified | |
| Example 800 | sublingual | liquid formulation | HER2/neu E75 | 1.25 | rotigotine(dopamine receptor agonist) | 0.1 | PEP | 0.3 | genetically modified | |
| Example 801 | sublingual | liquid formulation | HER2/neu E75 | 1.25 | Immepip(histamine receptor agonist) | 0.1 | PEP | 0.3 | genetically modified | |
| Example 802 | sublingual | liquid formulation | HER2/neu E75 | 1.25 | proxyfan(histamine receptor agonist) | 0.1 | PEP | 0.3 | genetically modified | 65 |
| Example 803 | sublingual | liquid formulation | HER2/neu E75 | 1.25 | 4-methylhistamine (histamine receptor agonist) | 0.1 | PEP | 0.3 | genetically modified | |
| Example 804 | sublingual | liquid formulation | HER2/neu E75 | 1.25 | diphenhydramine (histamine receptor antagonist) | 0.1 | PEP | 0.3 | genetically modified | 76 |
| Example 805 | sublingual | liquid formulation | HER2/neu E75 | 1.25 | azelastine(histamine receptor antagonist) | 0.1 | PEP | 0.3 | genetically modified | |
| Example 806 | sublingual | liquid formulation | HER2/neu E75 | 1.25 | cimetidine(histamine receptor antagonist) | 0.1 | PEP | 0.3 | genetically modified | |
| Example 807 | sublingual | liquid formulation | HER2/neu E75 | 1.25 | famotidine(histamine receptor antagonist) | 0.1 | PEP | 0.3 | genetically modified | 86 |
| Example 808 | sublingual | liquid formulation | HER2/neu E75 | 1.25 | sumatriptan(serotonin receptor agonist) | 0.1 | PEP | 0.3 | genetically modified | |
| Example 809 | sublingual | liquid formulation | HER2/neu E75 | 1.25 | zolmitriptan(serotonin receptor agonist) | 0.1 | PEP | 0.3 | genetically modified | 95 |
| Example 810 | sublingual | liquid formulation | HER2/neu E75 | 1.25 | metergoline(serotonin receptor antagonist) | 0.1 | PEP | 0.3 | genetically modified | |
| Example 811 | sublingual | liquid formulation | HER2/neu E75 | 1.25 | clozapine(serotonin receptor antagonist) | 0.1 | PEP | 0.3 | genetically modified | |
| Example 812 | sublingual | liquid formulation | HER2/neu E75 | 1.25 | olanzapine(serotonin receptor antagonist) | 0.1 | PEP | 0.3 | genetically modified | 55 |
| Example 813 | sublingual | liquid formulation | HER2/neu E75 | 1.25 | yohimbine(serotonin receptor antagonist) | 0.1 | PEP | 0.3 | genetically modified | |
| Example 814 | sublingual | liquid formulation | HER2/neu E75 | 1.25 | tolvaptan(vasopressin receptor antagonist) | 0.1 | PEP | 0.3 | genetically modified | |
| Example 815 | sublingual | liquid formulation | HER2/neu E75 | 1.25 | desmopressin (vasopressin receptor agonist) | 0.1 | PEP | 0.3 | genetically modified | |
| Example 816 | sublingual | liquid formulation | HER2/neu E75 | 1.25 | oxybutynin(muscarine receptor antagonist) | 0.1 | PEP | 0.3 | genetically modified | 56 |
| Example 817 | sublingual | liquid formulation | HER2/neu E75 | 1.25 | acetylcholine(muscarine receptor antagonist) | 0.1 | PEP | 0.3 | genetically modified | |
| Example 818 | sublingual | liquid formulation | HER2/neu E75 | 1.25 | trimebutine(muscarine receptor antagonist) | 0.1 | PEP | 0.3 | genetically modified | |
| Example 819 | sublingual | liquid formulation | HER2/neu E75 | 1.25 | pilocarpine(muscarine receptor agonist) | 0.1 | PEP | 0.3 | genetically modified | |
| Example 820 | sublingual | liquid formulation | HER2/neu E75 | 1.25 | tamsulosin(adrenalin receptor antagonist) | 0.1 | PEP | 0.3 | genetically modified | 67 |
| Example 821 | sublingual | liquid formulation | HER2/neu E75 | 1.25 | propranolol(adrenalin receptor antagonist) | 0.1 | PEP | 0.3 | genetically modified | 67 |

TABLE 47-continued

| No. | administration route | dosage form | antigen name | amount [%] | Th2 cell differentiation inhibitor name | amount [%] | helper peptide name | amount [%] | Mouse for immunological evaluation | Results of immunization (ELISPOT) |
|---|---|---|---|---|---|---|---|---|---|---|
| Example 822 | sublingual | liquid formulation | HER2/neu E75 | 1.25 | xylazine(adrenalin receptor agonist) | 0.1 | PEP | 0.3 | genetically modified | |
| Example 823 | sublingual | liquid formulation | HER2/neu E75 | 1.25 | novokinin(angiotensin receptor agonist) | 0.1 | PEP | 0.3 | genetically modified | |
| Example 824 | sublingual | liquid formulation | HER2/neu E75 | 1.25 | baclofen(GABA receptor agonist) | 0.1 | PEP | 0.3 | genetically modified | |
| Example 825 | sublingual | liquid formulation | HER2/neu E75 | 1.25 | TRAP-6(thrombin receptor agonist) | 0.1 | PEP | 0.3 | genetically modified | |
| Example 826 | sublingual | liquid formulation | HER2/neu E75 | 1.25 | loperamide(opioid receptor agonist) | 0.1 | PEP | 0.3 | genetically modified | 76 |
| Example 827 | sublingual | liquid formulation | HER2/neu E75 | 1.25 | adenosine diphosphate (ADP receptor agonist) | 0.1 | PEP | 0.3 | genetically modified | |
| Example 828 | sublingual | liquid formulation | HER2/neu E75 | 1.25 | montelukast(leukotriene receptor antagonist) | 0.1 | PEP | 0.3 | genetically modified | |
| Example 829 | sublingual | liquid formulation | HER2/neu E75 | 1.25 | zileuton(leukotriene receptor antagonist) | 0.1 | PEP | 0.3 | genetically modified | |
| Example 830 | sublingual | liquid formulation | HER2/neu E75 | 1.25 | leukotriene B4 (leukotriene receptor agonist) | 0.1 | PEP | 0.3 | genetically modified | |
| Example 831 | sublingual | liquid formulation | HER2/neu E75 | 1.25 | melatonin(melatonin receptor agonist) | 0.1 | PEP | 0.3 | genetically modified | 76 |
| Example 832 | sublingual | liquid formulation | HER2/neu E75 | 1.25 | somatostatin-14 (somatostatin receptor agonist) | 0.1 | PEP | 0.3 | genetically modified | |
| Example 833 | sublingual | liquid formulation | HER2/neu E75 | 1.25 | GW405833 (cannabinoid receptor agonist) | 0.1 | PEP | 0.3 | genetically modified | |
| Example 834 | sublingual | liquid formulation | HER2/neu E75 | 1.25 | SEW2871(sphingosine-1 phosphate receptor agonist) | 0.1 | PEP | 0.3 | genetically modified | |
| Example 835 | sublingual | liquid formulation | HER2/neu E75 | 1.25 | biphenylindanone A (metabotropic glutamate receptor agonist) | 0.1 | PEP | 0.3 | genetically modified | |
| Example 836 | sublingual | liquid formulation | HER2/neu E75 | 1.25 | L-AP4(metabotropic glutamate receptor agonist) | 0.1 | PEP | 0.3 | genetically modified | 67 |
| Example 837 | sublingual | liquid formulation | HER2/neu E75 | 1.25 | dipotassium glycyrrhizinate (phospholipase A2 inhibitor) | 0.1 | PEP | 0.3 | genetically modified | |
| Example 838 | sublingual | liquid formulation | HER2/neu E75 | 1.25 | pirfenidone(TGF-beta production inhibitor) | 0.1 | PEP | 0.3 | genetically modified | |
| Example 839 | sublingual | liquid formulation | HER2/neu E75 | 1.25 | tranilast(TGF-beta production inhibitor) | 0.1 | PEP | 0.3 | genetically modified | |
| Example 840 | sublingual | liquid formulation | HER2/neu E75 | 1.25 | suplatast tosylate(Th2 cytokine inhibitor) | 0.1 | PEP | 0.3 | genetically modified | |

PEP: Peptide-25 (SEQ ID NO: 13) (helper peptide)
PADRE: PADRE (SEQ ID NO: 15) (helper peptide)

TABLE 48

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 68 | sublingual | liquid formulation | OVAp | 1 | — | — | C57BL/6 | 0 |
| Example 841 | sublingual | liquid formulation | OVAp | 0.2 | loxoprofen (COX inhibitor) | 0.5 | C57BL/6 | 54 |
| Example 842 | sublingual | liquid formulation | OVAp | 0.2 | etodolac (COX inhibitor) | 0.5 | C57BL/6 | |
| Example 843 | sublingual | liquid formulation | OVAp | 0.2 | indomethacin(COX inhibitor) | 0.5 | C57BL/6 | |
| Example 844 | sublingual | liquid formulation | OVAp | 0.2 | aspirin(COX inhibitor) | 0.5 | C57BL/6 | |
| Example 845 | sublingual | liquid formulation | OVAp | 0.2 | diclofenac (COX inhibitor) | 0.5 | C57BL/6 | |
| Example 846 | sublingual | liquid formulation | OVAp | 0.2 | ketoprofen(COX inhibitor) | 0.5 | C57BL/6 | |
| Example 847 | sublingual | liquid formulation | OVAp | 0.2 | celecoxib(COX inhibitor) | 0.5 | C57BL/6 | |

TABLE 48-continued

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Example 848 | sublingual | liquid formulation | OVAp | 0.2 | valdecoxib(COX inhibitor) | 0.5 | C57BL/6 | |
| Example 849 | sublingual | liquid formulation | OVAp | 0.2 | GW627368X(prostaglandin receptor antagonist) | 0.5 | C57BL/6 | 42 |
| Example 850 | sublingual | liquid formulation | OVAp | 0.2 | RO1138452(prostaglandin receptor antagonist) | 0.5 | C57BL/6 | |
| Example 851 | sublingual | liquid formulation | OVAp | 0.2 | BWA868C(prostaglandin receptor antagonist) | 0.5 | C57BL/6 | |
| Example 852 | sublingual | liquid formulation | OVAp | 0.2 | sulprostone(prostaglandin receptor agonist) | 0.5 | C57BL/6 | 47 |
| Example 853 | sublingual | liquid formulation | OVAp | 0.2 | cloprostenol(prostaglandin receptor agonist) | 0.5 | C57BL/6 | |
| Example 854 | sublingual | liquid formulation | OVAp | 0.2 | quercetin(TSLP production inhibitor) | 0.5 | C57BL/6 | 49 |
| Example 855 | sublingual | liquid formulation | OVAp | 0.2 | berberine(TSLP production inhibitor) | 0.5 | C57BL/6 | |
| Example 856 | sublingual | liquid formulation | OVAp | 0.2 | noscapine(TSLP production inhibitor) | 0.5 | C57BL/6 | |
| Example 857 | sublingual | liquid formulation | OVAp | 0.2 | 3,3'-diindolylmethane(TSLP production inhibitor) | 0.5 | C57BL/6 | |
| Example 858 | sublingual | liquid formulation | OVAp | 0.2 | xanthone(TSLP production inhibitor) | 0.5 | C57BL/6 | |
| Example 859 | sublingual | liquid formulation | OVAp | 0.2 | parthenolide(TSLP production inhibitor) | 0.5 | C57BL/6 | |
| Example 860 | sublingual | liquid formulation | OVAp | 0.2 | resveratrol(TSLP production inhibitor) | 0.5 | C57BL/6 | |
| Example 861 | sublingual | liquid formulation | OVAp | 0.2 | 2',5'-dideoxyadenosine (adenylate cyclase inhibitor) | 0.5 | C57BL/6 | |
| Example 862 | sublingual | liquid formulation | OVAp | 0.2 | docosahexaenoic acid(omega-3 fatty acid) | 0.5 | C57BL/6 | |
| Example 863 | sublingual | liquid formulation | OVAp | 0.2 | clofibrate(PPAR agonist) | 0.5 | C57BL/6 | 40 |
| Example 864 | sublingual | liquid formulation | OVAp | 0.2 | fenofibrate(PPAR agonist) | 0.5 | C57BL/6 | |
| Example 865 | sublingual | liquid formulation | OVAp | 0.2 | SCH23390(dopamine receptor antagonist) | 0.5 | C57BL/6 | |
| Example 866 | sublingual | liquid formulation | OVAp | 0.2 | ropinirole(dopamine receptor agonist) | 0.5 | C57BL/6 | |
| Example 867 | sublingual | liquid formulation | OVAp | 0.2 | rotigotine(dopamine receptor agonist) | 0.5 | C57BL/6 | |
| Example 868 | sublingual | liquid formulation | OVAp | 0.2 | Immepip(histamine receptor agonist) | 0.5 | C57BL/6 | |
| Example 869 | sublingual | liquid formulation | OVAp | 0.2 | proxyfan(histamine receptor agonist) | 0.5 | C57BL/6 | |
| Example 870 | sublingual | liquid formulation | OVAp | 0.2 | 4-methylhistamine(histamine receptor agonist) | 0.5 | C57BL/6 | |
| Example 871 | sublingual | liquid formulation | OVAp | 0.2 | diphenhydramine(histamine receptor antagonist) | 0.5 | C57BL/6 | 41 |
| Example 872 | sublingual | liquid formulation | OVAp | 0.2 | azelastine(histamine receptor antagonist) | 0.5 | C57BL/6 | |
| Example 873 | sublingual | liquid formulation | OVAp | 0.2 | cimetidine(histamine receptor antagonist) | 0.5 | C57BL/6 | |
| Example 874 | sublingual | liquid formulation | OVAp | 0.2 | famotidine(histamine receptor antagonist) | 0.5 | C57BL/6 | |
| Example 875 | sublingual | liquid formulation | OVAp | 0.2 | sumatriptan(serotonin receptor agonist) | 0.5 | C57BL/6 | |
| Example 876 | sublingual | liquid formulation | OVAp | 0.2 | zolmitriptan(serotonin receptor agonist) | 0.5 | C57BL/6 | 44 |
| Example 877 | sublingual | liquid formulation | OVAp | 0.2 | metergoline(serotonin receptor antagonist) | 0.5 | C57BL/6 | |
| Example 878 | sublingual | liquid formulation | OVAp | 0.2 | clozapine(serotonin receptor antagonist) | 0.5 | C57BL/6 | |
| Example 879 | sublingual | liquid formulation | OVAp | 0.2 | olanzapine(serotonin receptor antagonist) | 0.5 | C57BL/6 | |
| Example 880 | sublingual | liquid formulation | OVAp | 0.2 | yohimbine(serotonin receptor antagonist) | 0.5 | C57BL/6 | |
| Example 881 | sublingual | liquid formulation | OVAp | 0.2 | tolvaptan(vasopressin receptor antagonist) | 0.5 | C57BL/6 | |
| Example 882 | sublingual | liquid formulation | OVAp | 0.2 | desmopressin(vasopressin receptor agonist) | 0.5 | C57BL/6 | |
| Example 883 | sublingual | liquid formulation | OVAp | 0.2 | oxybutynin(muscarine receptor antagonist) | 0.5 | C57BL/6 | |
| Example 884 | sublingual | liquid formulation | OVAp | 0.2 | acetylcholine(muscarine receptor antagonist) | 0.5 | C57BL/6 | |

TABLE 48-continued

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Example 885 | sublingual | liquid formulation | OVAp | 0.2 | trimebutine(muscarine receptor antagonist) | 0.5 | C57BL/6 | |
| Example 886 | sublingual | liquid formulation | OVAp | 0.2 | pilocarpine(muscarine receptor agonist) | 0.5 | C57BL/6 | |
| Example 887 | sublingual | liquid formulation | OVAp | 0.2 | tamsulosin(adrenalin receptor antagonist) | 0.5 | C57BL/6 | |
| Example 888 | sublingual | liquid formulation | OVAp | 0.2 | propranolol(adrenalin receptor antagonist) | 0.5 | C57BL/6 | |
| Example 889 | sublingual | liquid formulation | OVAp | 0.2 | xylazine(adrenalin receptor agonist) | 0.5 | C57BL/6 | |
| Example 890 | sublingual | liquid formulation | OVAp | 0.2 | novokinin(angiotensin receptor agonist) | 0.5 | C57BL/6 | |
| Example 891 | sublingual | liquid formulation | OVAp | 0.2 | baclofen(GABA receptor agonist) | 0.5 | C57BL/6 | |
| Example 892 | sublingual | liquid formulation | OVAp | 0.2 | TRAP-6(thrombin receptor agonist) | 0.5 | C57BL/6 | |
| Example 893 | sublingual | liquid formulation | OVAp | 0.2 | loperamide(opioid receptor agonist) | 0.5 | C57BL/6 | 46 |
| Example 894 | sublingual | liquid formulation | OVAp | 0.2 | adenosine diphosphate(ADP receptor agonist) | 0.5 | C57BL/6 | |
| Example 895 | sublingual | liquid formulation | OVAp | 0.2 | montelukast(leukotriene receptor antagonist) | 0.5 | C57BL/6 | |
| Example 896 | sublingual | liquid formulation | OVAp | 0.2 | leukotriene B4(leukotriene receptor agonist) | 0.5 | C57BL/6 | |
| Example 897 | sublingual | liquid formulation | OVAp | 0.2 | melatonin(melatonin receptor agonist) | 0.5 | C57BL/6 | 44 |
| Example 898 | sublingual | liquid formulation | OVAp | 0.2 | somatostatin-14 (somatostatin receptor agonist) | 0.5 | C57BL/6 | |
| Example 899 | sublingual | liquid formulation | OVAp | 0.2 | GW405833(cannabinoid receptor agonist) | 0.5 | C57BL/6 | |
| Example 900 | sublingual | liquid formulation | OVAp | 0.2 | SEW2871(sphingosine-1 phosphate receptor agonist) | 0.5 | C57BL/6 | |
| Example 901 | sublingual | liquid formulation | OVAp | 0.2 | biphenylindanone A (metabotropic glutamate receptor agonist) | 0.5 | C57BL/6 | |
| Example 902 | sublingual | liquid formulation | OVAp | 0.2 | L-AP4(metabotropic glutamate receptor agonist) | 0.5 | C57BL/6 | |
| Example 903 | sublingual | liquid formulation | OVAp | 0.2 | glycyrrhizic acid (phospholipase A2 inhibitor) | 0.5 | C57BL/6 | |
| Example 904 | sublingual | liquid formulation | OVAp | 0.2 | pirfenidone(TGF-beta production inhibitor) | 0.5 | C57BL/6 | |
| Example 905 | sublingual | liquid formulation | OVAp | 0.2 | tranilast(TGF-beta production inhibitor) | 0.5 | C57BL/6 | |
| Example 906 | sublingual | liquid formulation | OVAp | 0.2 | suplatast tosylate (Th2 cytokine inhibitor) | 0.5 | C57BL/6 | |

OVAp: OVA peptide (SEQ ID NO: 16)

TABLE 49

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 69 | sublingual | liquid formulation | HER2/neu_A24 | 1.25 | — | — | BALB/c | |
| Example 907 | sublingual | liquid formulation | HER2/neu_A24 | 1.25 | loxoprofen(COX inhibitor) | 0.5 | BALB/c | |
| Example 908 | sublingual | liquid formulation | HER2/neu_A24 | 1.25 | GW627368X(prostaglandin receptor antagonist) | 0.5 | BALB/c | |
| Example 909 | sublingual | liquid formulation | HER2/neu_A24 | 1.25 | sulprostone(prostaglandin receptor agonist) | 0.5 | BALB/c | |
| Example 910 | sublingual | liquid formulation | HER2/neu_A24 | 1.25 | quercetin(TSLP production inhibitor) | 0.5 | BALB/c | |
| Example 911 | sublingual | liquid formulation | HER2/neu_A24 | 1.25 | clofibrate(PPAR agonist) | 0.5 | BALB/c | |
| Example 912 | sublingual | liquid formulation | HER2/neu_A24 | 1.25 | famotidine(histamine receptor antagonist) | 0.5 | BALB/c | |

TABLE 49-continued

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Example 913 | sublingual | liquid formulation | HER2/neu_A24 | 1.25 | sumatriptan(serotonin receptor agonist) | 0.5 | BALB/c | |
| Example 914 | sublingual | liquid formulation | HER2/neu_A24 | 1.25 | loperamide(opioid receptor agonist) | 0.5 | BALB/c | |
| Example 915 | sublingual | liquid formulation | HER2/neu_A24 | 1.25 | melatonin(melatonin receptor agonist) | 0.5 | BALB/c | |

TABLE 50

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 70 | sublingual | liquid formulation | IPEP87 | 1.25 | — | — | genetically modified | |
| Example 916 | sublingual | liquid formulation | IPEP87 | 1.25 | loxoprofen(COX inhibitor) | 0.5 | genetically modified | |
| Example 917 | sublingual | liquid formulation | IPEP87 | 1.25 | GW627368X(prostaglandin receptor antagonist) | 0.5 | genetically modified | |
| Example 918 | sublingual | liquid formulation | IPEP87 | 1.25 | sulprostone(prostaglandin receptor agonist) | 0.5 | genetically modified | |
| Example 919 | sublingual | liquid formulation | IPEP87 | 1.25 | quercetin(TSLP production inhibitor) | 0.5 | genetically modified | |
| Example 920 | sublingual | liquid formulation | IPEP87 | 1.25 | clofibrate(PPAR agonist) | 0.5 | genetically modified | |
| Example 921 | sublingual | liquid formulation | IPEP87 | 1.25 | famotidine(histamine receptor antagonist) | 0.5 | genetically modified | |
| Example 922 | sublingual | liquid formulation | IPEP87 | 1.25 | sumatriptan(serotonin receptor agonist) | 0.5 | genetically modified | |
| Example 923 | sublingual | liquid formulation | IPEP87 | 1.25 | loperamide(opioid receptor agonist) | 0.5 | genetically modified | |
| Example 924 | sublingual | liquid formulation | IPEP87 | 1.25 | melatonin(melatonin receptor agonist) | 0.5 | genetically modified | |

TABLE 51

| No. | administration route | dosage form | antigen name | amount [%] | Th2 cell differentiation inhibitor name | amount [%] | Mouse for immunological evaluation | Results of immunization (ELISPOT) |
|---|---|---|---|---|---|---|---|---|
| Comparative example 71 | sublingual | liquid formulation | HER2/neu E75 | 1.25 | — | — | genetically modified | 3 |
| Example 925 | sublingual | liquid formulation | HER2/neu E75 | 1.25 | loxoprofen(COX inhibitor) | 0.1 | genetically modified | 56 |
| Example 926 | sublingual | liquid formulation | HER2/neu E75 | 1.25 | GW627368X(prostaglandin receptor antagonist) | 0.1 | genetically modified | |
| Example 927 | sublingual | liquid formulation | HER2/neu E75 | 1.25 | sulprostone(prostaglandin receptor agonist) | 0.5 | genetically modified | |
| Example 928 | sublingual | liquid formulation | HER2/neu E75 | 1.25 | quercetin(TSLP production inhibitor) | 0.1 | genetically modified | 67 |
| Example 929 | sublingual | liquid formulation | HER2/neu E75 | 1.25 | clofibrate(PPAR agonist) | 0.5 | genetically modified | |
| Example 930 | sublingual | liquid formulation | HER2/neu E75 | 1.25 | famotidine(histamine receptor antagonist) | 0.5 | genetically modified | |
| Example 931 | sublingual | liquid formulation | HER2/neu E75 | 1.25 | sumatriptan(serotonin receptor agonist) | 0.5 | genetically modified | |
| Example 932 | sublingual | liquid formulation | HER2/neu E75 | 1.25 | loperamide(opioid receptor agonist) | 0.5 | genetically modified | |
| Example 933 | sublingual | liquid formulation | HER2/neu E75 | 1.25 | melatonin(melatonin receptor agonist) | 0.5 | genetically modified | |

TABLE 52

| No. | administration route | dosage form | antigen name | antigen amount [%] | Th2 cell differentiation inhibitor name | Th2 cell differentiation inhibitor amount [%] | Mouse for immunological evaluation | Results of immunization (ELISPOT) |
|---|---|---|---|---|---|---|---|---|
| Comparative example 72 | sublingual | liquid formulation | HER2/neu_A02 | 1.25 | — | — | genetically modified | |
| Example 934 | sublingual | liquid formulation | HER2/neu_A02 | 1.25 | loxoprofen(COX inhibitor) | 0.5 | genetically modified | |
| Example 935 | sublingual | liquid formulation | HER2/neu_A02 | 1.25 | GW627368X(prostaglandin receptor antagonist) | 0.5 | genetically modified | |
| Example 936 | sublingual | liquid formulation | HER2/neu_A02 | 1.25 | sulprostone(prostaglandin receptor agonist) | 0.5 | genetically modified | |
| Example 937 | sublingual | liquid formulation | HER2/neu_A02 | 1.25 | quercetin(TSLP production inhibitor) | 0.5 | genetically modified | |
| Example 938 | sublingual | liquid formulation | HER2/neu_A02 | 1.25 | clofibrate(PPAR agonist) | 0.5 | genetically modified | |
| Example 939 | sublingual | liquid formulation | HER2/neu_A02 | 1.25 | famotidine(histamine receptor antagonist) | 0.5 | genetically modified | |
| Example 940 | sublingual | liquid formulation | HER2/neu_A02 | 1.25 | sumatriptan(serotonin receptor agonist) | 0.5 | genetically modified | |
| Example 941 | sublingual | liquid formulation | HER2/neu_A02 | 1.25 | loperamide(opioid receptor agonist) | 0.5 | genetically modified | |
| Example 942 | sublingual | liquid formulation | HER2/neu_A02 | 1.25 | melatonin(melatonin receptor agonist) | 0.5 | genetically modified | |

TABLE 53

| No. | administration route | dosage form | antigen name | antigen amount [%] | Th2 cell differentiation inhibitor name | Th2 cell differentiation inhibitor amount [%] | Mouse for immunological evaluation | Results of immunization (ELISPOT) |
|---|---|---|---|---|---|---|---|---|
| Comparative example 73 | sublingual | liquid formulation | MAGE3_A02 | 1.25 | — | — | genetically modified | |
| Example 943 | sublingual | liquid formulation | MAGE3_A02 | 1.25 | loxoprofen(COX inhibitor) | 0.5 | genetically modified | |
| Example 944 | sublingual | liquid formulation | MAGE3_A02 | 1.25 | GW627368X(prostaglandin receptor antagonist) | 0.5 | genetically modified | |
| Example 945 | sublingual | liquid formulation | MAGE3_A02 | 1.25 | sulprostone(prostaglandin receptor agonist) | 0.5 | genetically modified | |
| Example 946 | sublingual | liquid formulation | MAGE3_A02 | 1.25 | quercetin(TSLP production inhibitor) | 0.5 | genetically modified | |
| Example 947 | sublingual | liquid formulation | MAGE3_A02 | 1.25 | clofibrate(PPAR agonist) | 0.5 | genetically modified | |
| Example 948 | sublingual | liquid formulation | MAGE3_A02 | 1.25 | famotidine(histamine receptor antagonist) | 0.5 | genetically modified | |
| Example 949 | sublingual | liquid formulation | MAGE3_A02 | 1.25 | sumatriptan(serotonin receptor agonist) | 0.5 | genetically modified | |
| Example 950 | sublingual | liquid formulation | MAGE3_A02 | 1.25 | loperamide(opioid receptor agonist) | 0.5 | genetically modified | |
| Example 951 | sublingual | liquid formulation | MAGE3_A02 | 1.25 | melatonin(melatonin receptor agonist) | 0.5 | genetically modified | |

TABLE 54

| No. | administration route | dosage form | antigen name | antigen amount [%] | Th2 cell differentiation inhibitor name | Th2 cell differentiation inhibitor amount [%] | Mouse for immunological evaluation | Results of immunization (ELISPOT) |
|---|---|---|---|---|---|---|---|---|
| Comparative example 74 | sublingual | liquid formulation | HBVenv | 1.25 | — | — | genetically modified | |
| Example 952 | sublingual | liquid formulation | HBVenv | 1.25 | loxoprofen(COX inhibitor) | 0.5 | genetically modified | |
| Example 953 | sublingual | liquid formulation | HBVenv | 1.25 | GW627368X(prostaglandin receptor antagonist) | 0.5 | genetically modified | |
| Example 954 | sublingual | liquid formulation | HBVenv | 1.25 | sulprostone(prostaglandin receptor agonist) | 0.5 | genetically modified | |
| Example 955 | sublingual | liquid formulation | HBVenv | 1.25 | quercetin(TSLP production inhibitor) | 0.5 | genetically modified | |

TABLE 54-continued

|  |  |  | antigen | | Th2 cell differentiation inhibitor | | Mouse for | Results of |
|---|---|---|---|---|---|---|---|---|
| No. | administration route | dosage form | name | amount [%] | name | amount [%] | immunological evaluation | immunization (ELISPOT) |
| Example 956 | sublingual | liquid formulation | HBVenv | 1.25 | clofibrate(PPAR agonist) | 0.5 | genetically modified | |
| Example 957 | sublingual | liquid formulation | HBVenv | 1.25 | famotidine(histamine receptor antagonist) | 0.5 | genetically modified | |
| Example 958 | sublingual | liquid formulation | HBVenv | 1.25 | sumatriptan(serotonin receptor agonist) | 0.5 | genetically modified | |
| Example 959 | sublingual | liquid formulation | HBVenv | 1.25 | loperamide(opioid receptor agonist) | 0.5 | genetically modified | |
| Example 960 | sublingual | liquid formulation | HBVenv | 1.25 | melatonin(melatonin receptor agonist) | 0.5 | genetically modified | |

TABLE 55

|  |  |  | antigen | | Th2 cell differentiation inhibitor | | Mouse for | Results of |
|---|---|---|---|---|---|---|---|---|
| No. | administration route | dosage form | name | amount [%] | name | amount [%] | immunological evaluation | immunization (ELISPOT) |
| Comparative example 75 | sublingual | liquid formulation | OVA protein | 0.2 | — | — | C57BL/6 | |
| Example 961 | sublingual | liquid formulation | OVA protein | 0.2 | loxoprofen(COX inhibitor) | 0.5 | C57BL/6 | |
| Example 962 | sublingual | liquid formulation | OVA protein | 0.2 | GW627368X(prostaglandin receptor antagonist) | 0.5 | C57BL/6 | |
| Example 963 | sublingual | liquid formulation | OVA protein | 0.2 | sulprostone(prostaglandin receptor agonist) | 0.5 | C57BL/6 | |
| Example 964 | sublingual | liquid formulation | OVA protein | 0.2 | quercetin(TSLP production inhibitor) | 0.5 | C57BL/6 | |
| Example 965 | sublingual | liquid formulation | OVA protein | 0.2 | clofibrate(PPAR agonist) | 0.5 | C57BL/6 | |
| Example 966 | sublingual | liquid formulation | OVA protein | 0.2 | famotidine(histamine receptor antagonist) | 0.5 | C57BL/6 | |
| Example 967 | sublingual | liquid formulation | OVA protein | 0.2 | sumatriptan(serotonin receptor agonist) | 0.5 | C57BL/6 | |
| Example 968 | sublingual | liquid formulation | OVA protein | 0.2 | loperamide(opioid receptor agonist) | 0.5 | C57BL/6 | |
| Example 969 | sublingual | liquid formulation | OVA protein | 0.2 | melatonin(melatonin receptor agonist) | 0.5 | C57BL/6 | |

Preparation of Film Formulation for Sublingual Administration

To 46 parts by weight of D-mannitol (manufactured by Roquette) and 2.6 parts by weight of polyethylene glycol 400 (manufactured by Wako Pure Chemical Industries, Ltd.), 150 parts by weight of a purified water was added, and then mixed with ultrasonic waves. Then, 46 parts by weight of hydroxypropylcellulose (manufactured by NIPPON SODA CO., LTD, HPC-SSL), and an antigen peptide, Peptide-25 and a Th2 cell differentiation inhibitor in such an amount that the concentrations of these substances after drying are the concentrations as shown in Table 56, were added thereto, and mixed thoroughly. One hundredth of the solution (2.5 parts by weight) was dropped on a release film made by polyethylene terephthalate, dried with air and then dried under vacuum to obtain 1 parts by weight of a film formulation. The antigen peptide, and the Th2 cell differentiation inhibitor were available from the same supplier as described in the cream formulations for transdermal administration.

Preparation Orally-Disintegrating Tablet for Sublingual Administration

To 20 parts by weight of a gelatin (water soluble gelatin CSF, manufactured by Nippi, Incorporated) and 74.6 parts by weight of D-mannitol, 500 parts by weight of a purified water was added, and then mixed to form a solution. To the solution, an antigen peptide, Peptide-25 and a Th2 cell differentiation inhibitor were added in such an amount that the concentrations of these substances after drying are the concentrations as shown in Table 56 to form a solution. The solution was dispensed into molded aluminum containers, and freeze-dried whole day and night to obtain an orally-disintegrating tablet. For a mouse immunization test, the orally-disintegrating tablet was crushed, and 10 mg of the crushed tablet was weighed and used. The antigen peptide, and the Th2 cell differentiation inhibitor were available from the same supplier as described in the cream formulations for transdermal administration.

Mouse Immunization Test with Film Formulation for Sublingual Administration and Orally-Disintegrating Tablet for Sublingual Administration The film formulation for sublingual administration and orally-disintegrating tablet for sublingual administration prepared as described above were used in a mouse immunization test using a model animal for immunological evaluation. The immunity induction level was evaluated by ELISPOT method. Specifically, a mouse was anesthetized, and then administered the film formulation for sublingual administration or the orally-disintegrating tablet for sublingual administration at sublingual region, and then kept for 2 minutes. After 1 week, the mouse was again administered the film formulation for sublingual administration or the orally-disintegrating tablet for sublingual administration at sublingual region and then kept for 2 minutes. After 6 days, the level of the cellular immunity induction specific for the antigen was evaluated. Six days after the administration, the spleen of the mouse was removed to prepare a suspension of spleen cells. Spleen cells ($3 \times 10^6$ cells/well) and an antigen peptide (100 μM) were added with a culture solution to a well of ELISPOT plate containing a fixed anti-mouse IFN-γ antigen, and co-cultured at 37° C. in 5% $CO_2$ for 20 hours. The number of the spot representing IFN-γ producing cells (spot number/$3 \times 10^6$ cells) was evaluated by ELISPOT method. The results of the immunization test and the mouse used are shown in Table 56. In the film formulations and the orally-disintegrating tablets of Examples, the level of immunity induction was enhanced by Th2 cell differentiation inhibitor.

More specifically, one or more first cellular immunity induction promoters selected from the group consisting of cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glu-

TABLE 56

| No. | administration route | dosage form | antigen name | antigen amount [%] | Th2 cell differentiation inhibitor name | Th2 cell differentiation inhibitor amount [%] | helper peptide name | helper peptide amount [%] | Mouse for immunological evaluation | Results of immunization (ELISPOT) |
|---|---|---|---|---|---|---|---|---|---|---|
| Comparative example 76 | sublingual | film | OVAp | 1 | — | — | PEP | 0.5 | C57BL/6 | 2 |
| Example 970 | sublingual | film | OVAp | 1 | loxoprofen(COX inhibitor) | 1 | PEP | 0.5 | C57BL/6 | 64 |
| Example 971 | sublingual | film | OVAp | 1 | quercetin(TSLP production inhibitor) | 1 | PEP | 0.5 | C57BL/6 | 57 |
| Comparative example 77 | sublingual | orally disintegrating tablet | OVAp | 1 | — | — | PEP | 0.5 | C57BL/6 | 3 |
| Example 972 | sublingual | orally disintegrating tablet | OVAp | 1 | loxoprofen(COX inhibitor) | 1 | PEP | 0.5 | C57BL/6 | 59 |
| Example 973 | sublingual | orally disintegrating tablet | OVAp | 1 | quercetin(TSLP production inhibitor) | 1 | PEP | 0.5 | C57BL/6 | 51 |

OVAp: OVA peptide (SEQ ID NO: 16)
PEP: Peptide-25 (SEQ ID NO: 13) (helper peptide)

A first cellular immunity induction promoter effective to promote the induction of cellular immunity was evaluated using vaccine compositions containing an antigen for transdermal administration, mucosal administration and injection.

It was found that one or more first cellular immunity induction promoters selected from the group consisting of cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor and Th2 cytokine inhibitor were effective.

In preferred embodiments, one or more first cellular immunity induction promoters selected from the group consisting of cyclooxygenase inhibitor, prostaglandin receptor antagonist, prostaglandin receptor agonist, TSLP production inhibitor, PPAR agonist, histamine receptor agonist, histamine receptor antagonist, serotonin receptor agonist, serotonin receptor antagonist, muscarine receptor antagonist, adrenalin receptor antagonist, opioid receptor agonist, melatonin receptor agonist, metabotropic glutamate receptor agonist and TGF-beta production inhibitor were effective.

In more preferred embodiments, one or more first cellular immunity induction promoters selected from the group consisting of cyclooxygenase inhibitor, prostaglandin receptor antagonist, prostaglandin receptor agonist, TSLP production inhibitor, PPAR agonist, histamine receptor antagonist, serotonin receptor agonist, opioid receptor agonist and melatonin receptor agonist were effective.

In most preferred embodiments, cyclooxygenase inhibitor, TSLP production inhibitor, prostaglandin receptor antagonist, prostaglandin receptor agonist, PPAR agonist, TGF-beta production inhibitor, histamine receptor agonist, histamine receptor antagonist, serotonin receptor agonist, serotonin receptor antagonist, muscarine receptor antagonist, adrenalin receptor antagonist, opioid receptor agonist, melatonin receptor agonist, metabotropic glutamate receptor agonist and a combination of two or more of them were effective as a first cellular immunity induction promoter.

In more preferred embodiments, cyclooxygenase inhibitor, TSLP production inhibitor, prostaglandin receptor antagonist, prostaglandin receptor agonist, PPAR agonist, histamine receptor antagonist, serotonin receptor agonist, opioid receptor agonist, melatonin receptor agonist, and a combination of two or more of them were particularly effective as a first cellular immunity induction promoter.

It was also found that cellular immunity induction was further promoted by the addition of one or more second cellular immunity induction promoters selected from the group consisting of TLR ligand, cyclic dinucleotide and immunomodulatory small molecule drug and/or helper peptide.

With respect to transdermal administration, effect of cream formulation was confirmed, and a strong immunity induction was also confirmed using tape formulation. The tape formulation is a preferable form in view of convenient administration and storage stability.

With respect to mucosal administration, sublingual route is preferable rather than nasal route in view of safety. An effect of liquid formulation was confirmed. A strong immunity induction was also confirmed using film formulation and orally-disintegrating tablet. The film formulation and orally-disintegrating tablet are a preferable form in view of convenient administration and storage stability.

A strong immunity induction was also confirmed using injections.

What is claimed is:

1. A method for inducing cellular immunity in a subject, comprising transdermally administering, to intact skin or under mildly irritating conditions, an immunogenic composition comprising:
   an antigen,
   at least one first cellular immunity induction promoter selected from the group consisting of a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenergic receptor antagonist, an adrenergic receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor, and
   a TLR ligand other than a TLR9 ligand.

2. The method according to claim 1, wherein the composition is administered to the skin under a mildly irritating condition.

3. The method according to claim 2, wherein the mildly irritating condition is a condition under which transepidermal water loss (TEWL) in a model animal for skin irritation evaluation before the administration of the composition is 50 g/hm² or less.

4. The method according to claim 2, wherein the mildly irritating condition is a condition under which the cutaneous TSLP level in a model animal for skin irritation evaluation at completion of the administration of the composition is 10000 pg/mg protein or less.

5. The method according to claim 1, wherein the method is for the treatment of a cancer.

6. The method according to claim 1, wherein the method is for the treatment of a viral disease.

7. The method according to claim 1, wherein the TLR ligand is a TLR4 ligand.

8. The method according to claim 7, wherein the TLR4 ligand is a lipopolysaccharide (LPS) derived from bacteria or plants.

9. The method according to claim 8, wherein the TLR4 ligand is a lipopolysaccharide (LPS) derived from *Pantoea* genus.

10. The method according to claim 1, wherein the TLR ligand is a TLR7 and/or TLR8 ligand.

11. The method according to claim 10, wherein the TLR7 and/or TLR8 ligand is imiquimod.

12. The method according to claim 1, wherein the first cellular immunity induction promoter is a cyclooxygenase inhibitor.

13. The method according to claim 12, wherein the cyclooxygenase inhibitor is selected from etodolac, loxoprofen, indomethacin, aspirin, diclofenac, ketoprofen, celecoxib, valdecoxib, and derivatives thereof, and pharmacologically acceptable salts thereof.

14. The method according to claim 12, wherein the cyclooxygenase inhibitor is loxoprofen.

15. The method according to claim 11, wherein the cyclooxygenase inhibitor is loxoprofen.

* * * * *